(12) United States Patent
Heck et al.

(10) Patent No.: US 10,181,018 B2
(45) Date of Patent: Jan. 15, 2019

(54) ANALOGS OF PROXISOME PROLIFERATOR ACTIVATED RECEPTOR (PPAR) AGONISTS AND METHODS OF USING THE SAME

(71) Applicant: The University of Toledo, Toledo, OH (US)

(72) Inventors: Bruce E. Heck, Toledo, OH (US); Dong Hyun Kim, Toledo, OH (US); Paul W. Erhardt, Toledo, OH (US); Brian J. Kress, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 15/699,054

(22) Filed: Sep. 8, 2017

(65) Prior Publication Data
US 2018/0012002 A1  Jan. 11, 2018

Related U.S. Application Data

(60) Continuation-in-part of application No. 15/593,750, filed on May 12, 2017, which is a division of application No. 14/773,022, filed as application No. PCT/US2014/027817 on Mar. 14, 2014, now Pat. No. 9,695,137.

(60) Provisional application No. 61/786,030, filed on Mar. 14, 2013.

(51) Int. Cl.
| | | |
|---|---|---|
| C07D 277/20 | (2006.01) |
| C07D 277/46 | (2006.01) |
| C07D 277/48 | (2006.01) |
| G06F 21/31 | (2013.01) |
| H04W 12/06 | (2009.01) |
| A61K 45/06 | (2006.01) |
| A61K 31/426 | (2006.01) |
| A61K 31/5575 | (2006.01) |
| C07D 277/22 | (2006.01) |
| C07D 277/24 | (2006.01) |
| H04W 12/04 | (2009.01) |
| H04W 12/08 | (2009.01) |

(52) U.S. Cl.
CPC ............ *G06F 21/31* (2013.01); *A61K 31/426* (2013.01); *A61K 31/5575* (2013.01); *A61K 45/06* (2013.01); *C07D 277/22* (2013.01); *C07D 277/24* (2013.01); *H04W 12/06* (2013.01); *H04W 12/04* (2013.01); *H04W 12/08* (2013.01)

(58) Field of Classification Search
CPC ... C07D 277/20; C07D 277/46; C07D 277/48
See application file for complete search history.

*Primary Examiner* — Samira J Jean-Louis
(74) *Attorney, Agent, or Firm* — MacMillan, Sobanski & Todd, LLC

(57) ABSTRACT

Peroxisome proliferator activated receptor (PPAR) compounds, and methods of using the same for treating bone fractures, treating osteoporosis and/or metabolic bone diseases, and inducing osteogenesis and/or chondrogenesis, are disclosed.

8 Claims, 10 Drawing Sheets
(3 of 10 Drawing Sheet(s) Filed in Color)

Scheme 1 – Eastern half synthesis

Scheme 2 – O-series synthesis

Scheme 3 – S-series synthesis

Scheme 4 – NH-series synthesis

Scheme 5 – N-Methyl synthesis

Scheme 6 – N-Alkyl synthesis

Scheme 7 – $R_1$ & $R_2$ Western Ring Analogs Group #1

Scheme 8 – $R_1$ & $R_2$ Western Ring Analogs Group #2

Scheme 9 – Central Heterocycle "Thiazole-flip"

Scheme 10 – Central Heterocycle Triazole Synthesis

Scheme 11 – Carboxylic Acid Bioisostere 44

Scheme 12 – Carboxylic Acid Bioisosteres 49 and 51

Scheme 13 – Carboxylic Acid Bioisosteres 53, 56, and 57 Synthesis

Scheme 14 – Naphthalene Sulfonic Acid 61 and Amide 62 Syntheses

ANALOGS OF PROXISOME PROLIFERATOR ACTIVATED RECEPTOR (PPAR) AGONISTS AND METHODS OF USING THE SAME

RELATED APPLICATIONS

The present application is continuation-in-part of U.S. Ser. No. 15/593,750 filed May 12, 2017, which is a divisional application of U.S. Ser. No. 14/773,022 filed Sep. 4, 2015, now U.S. Pat. No. 9,695,137 issued Jul. 4, 2017, which is a national stage application filed under 35 USC § 371 of international application PCT/US2014/027817 filed Mar. 14, 2014, which claims priority to U.S. Provisional Application Ser. No. 61/786,030, filed under 35 U.S.C. § 111(b) on Mar. 14, 2013, the disclosures of which are expressly incorporated herein by reference in their entireties.

STATEMENT REGARDING FEDERALLY SPONSORED RESEARCH

The invention was made with no government support. The government has no rights in the invention.

TECHNICAL FIELD

The present disclosure relates to the field of compounds, compositions, and methods useful for the treatment or prevention of osteoporosis, osteoarthritis, metabolic bone disorders, fracture management, and other musculoskeletal disorders.

BACKGROUND OF THE INVENTION

Osteoporosis is a silent disease of bones that affects tens of millions of people over the age of 50. The disease results in decreased bone mineral density and ultimately bone fracture. Osteoporosis can lead to acute and chronic fractures, causing significant morbidity and mortality to patients. Other metabolic bone diseases can similarly result in weakened bones and fractures. Currently, the best medications available can reduce recurrent fracture risk only 65% of the time, and are associated with significant risks such as avascular necrosis of the temporomandibular joints, subtrochanteric femur fractures, and malignant bone tumors.

Osteoarthritis is the most common joint disorder in the world, and affects the majority of people over the age of 65. Osteoarthritis is a disease of cartilage and bone that results in the wearing away of the lining of the joint, and ultimately bone-on-bone changes. Osteoarthritis can lead to crippling joint pain and deformity, causing significant morbidity to patients. Currently, there are no medical treatments available to prevent or halt the progression of osteoarthritis. The standard of care for treating osteoarthritis dictates supportive pain management measures such as medications, physical therapy, braces, lifestyle changes, and activity modifications, until a patient can no longer tolerate the pain, at which point a joint fusion or replacement may be performed.

It would be advantageous to develop effective ways of preventing or treating osteoporosis, osteoarthritis, metabolic bone disorders, fracture management, and other musculoskeletal disorders.

SUMMARY OF THE INVENTION

Provided herein is a method of inducing osteogenesis or chondrogenesis, the method comprising treating mammalian stem cells with an effective amount of one or more of a PPARδ agonist and a 20-OH-PGE$_2$ antagonist, whereby the mammalian stem cells differentiate into a cell of osteoblast or chondroblast lineage.

In a first aspect, there is provided a method of inducing osteogenesis or chondrogenesis which includes: administering an effective amount of a pharmaceutical composition to a mammalian patient in need thereof, where the pharmaceutical composition comprises a peroxisome proliferator activated receptor (PPAR) compound in an amount sufficient to prompt stem cells in the patient to contribute toward bone formation, and a pharmaceutically acceptable carrier, excipient, diluent or adjuvant; wherein the PPAR compound has a chemical structure of Formula I:

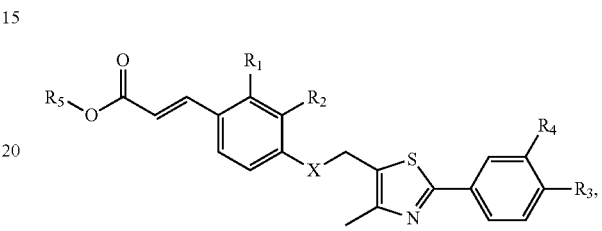

wherein: X is O, S, NH, or N CH$_3$; R$_1$ is H; R$_2$ is H; R$_3$ is H or CF$_3$; R$_4$ is H or CF$_3$; and R$_5$ is H or CH$_3$; and salts, isomers, solvates, hydrates, polymorphs, and prodrugs thereof.

In certain embodiments, the compound comprises BK-4-03, wherein X=NH, R$_1$=R$_2$=R$_4$=R$_5$=H and R$_3$=CF$_3$.

In certain embodiments, the compound comprises BK-4-04, wherein X=S, R$_1$=R$_2$=R$_4$=R$_5$=H and R$_3$=CF$_3$.

In certain embodiments, the compound comprises BK-4-15, wherein X=NCH$_3$, R$_1$=R$_2$=R$_4$=R$_5$=H and R$_3$=CF$_3$.

In certain embodiments, the administration is by surgical implantation including allograft bone, bone substitutes or bone scaffold matrices, or by localized injection of liquid or gel formulations or delivery systems to or near the bone.

In certain embodiments, the administration is by an intravenous, intramuscular or subcutaneous injection of liquid or gel formulations or delivery systems.

In another aspect, there is provided a method of inducing osteogenesis or chondrogenesis which includes administering induced stem cells to a mammalian patient in need thereof; wherein the induced stem cells are derived from incubating stem cells with a pharmaceutical composition comprising a peroxisome proliferator activated receptor (PPAR) compound having a chemical structure of Formula I.

In certain embodiments, the mammalian patient is a human and the stem cells are either harvested from the same patient or supplied from another mammalian donor.

In certain embodiments, the stem cells are present in a human patient in need of therapy for osteoarthritis, cartilage disorder, bone fracture, osteoporosis, metabolic bone disease, avascular necrosis, or concurrent with skeletal surgery.

In certain embodiments, the stem cells are present in a culture media after either being harvested from a human patient or another mammal; and wherein after treatment are administered to a human patient as a therapy for osteoarthritis, bone fracture, osteoporosis, metabolic bone disease, avascular necrosis or concurrent with skeletal surgery.

In certain embodiments, the patient has one or more of: injury to articular cartilage; osteoarthritis; costochondritis; herniation; achondroplasia; relapsing polychondritis; benign or non-cancerous chondroma; and, malignant or cancerous chondrosarcoma.

In another aspect, there is provided a compound comprising a structural of Formula I:

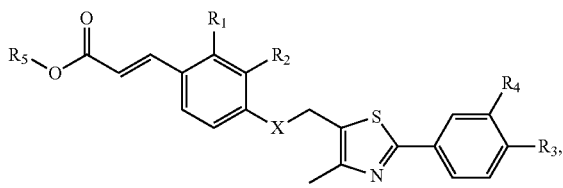

wherein: X is O, S, NH, or N CH$_3$; R$_1$ is H; R$_2$ is H; R$_3$ is H or CF$_3$; R$_4$ is H or CF$_3$; and R$_5$ is H or CH$_3$; and salts, isomers, stereoisomers, enantiomers, racemates, solvates, hydrates, polymorphs, and prodrugs thereof.

In certain embodiments, the compound comprises BK-4-03, wherein X=NH, R$_1$=R$_2$=R$_4$=R$_5$=H and R$_3$=CF$_3$.

In certain embodiments, the compound comprises BK-4-04, wherein X=S, R$_1$=R$_2$=R$_4$=R$_5$=H and R$_3$=CF$_3$.

In certain embodiments, the compound comprises BK-4-15, wherein X=NCH$_3$, R$_1$=R$_2$=R$_4$=R$_5$=H and R$_3$=CF$_3$.

In another aspect, there is provided a pharmaceutical composition comprising: a compound of Formula I; and one or more of a pharmaceutically acceptable carrier, excipient, diluent or adjuvant.

In another aspect, there is provided a method for making the compound of Formula I, wherein in X=S, comprising following scheme 3 synthesis.

In another aspect, there is provided a method for making the compound of Formula I, wherein in X=NH, comprising following scheme 4 synthesis.

In another aspect, there is provided a method for making the compound of Formula I, wherein in X=CH$_3$, comprising following scheme 5 synthesis.

In another aspect, there is provided a method for making the compound of Formula I, wherein in X=alkyl, comprising following scheme 6 synthesis.

In other aspects pertaining to chemical syntheses, further methods are provided in additional schemes 7 to 14 and their associated experimental examples.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

DETAILED DESCRIPTION OF THE INVENTION

Figure 1:
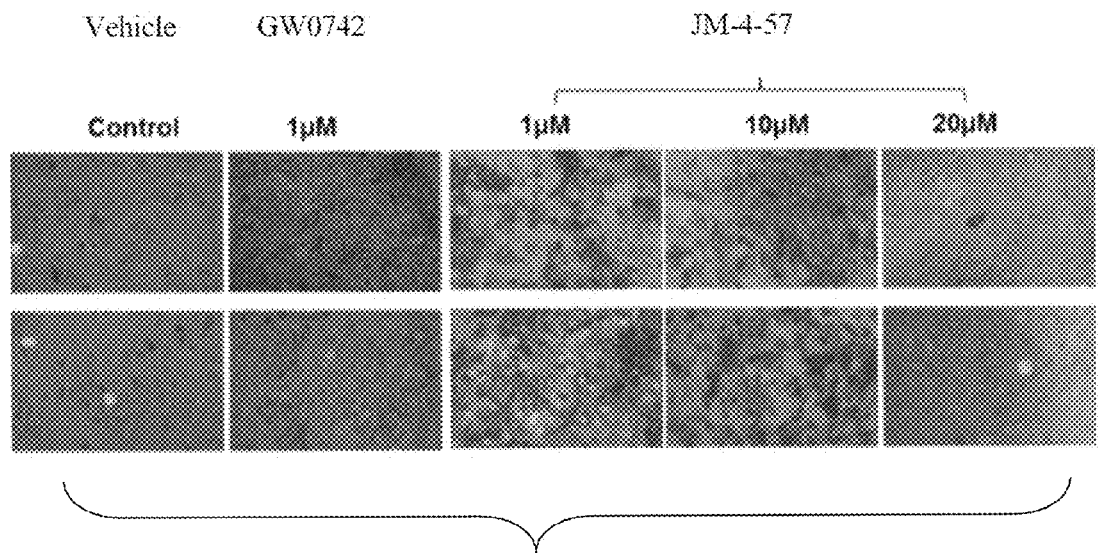
FIG. 1: Increased osteogenic formation from MSCs treated with JM-4-57 (X=O, R$_1$=R$_2$=R$_5$=H, R$_3$=CF$_3$, R$_4$=F). Note that activity peaks at 10 μM.
Figure 2:
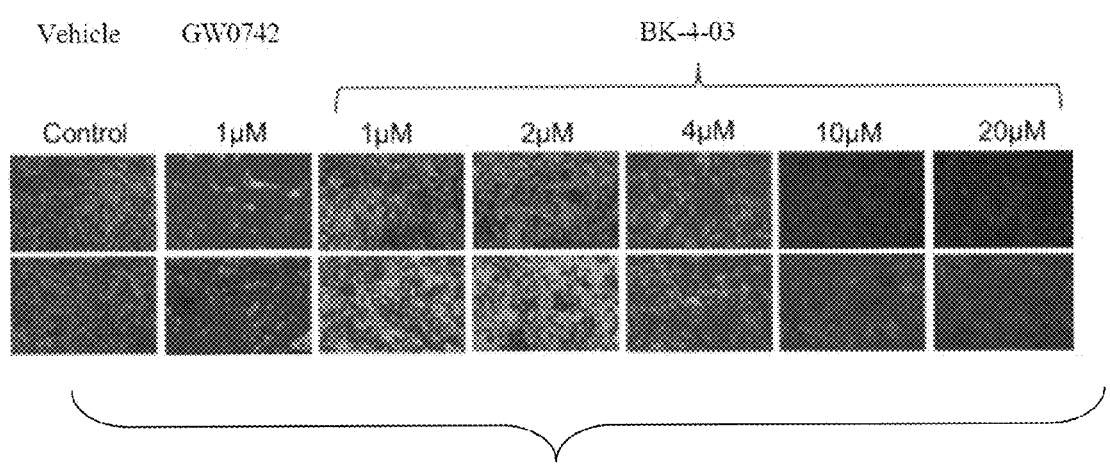
FIG. 2: Increased osteogenic formation from MSCs treated with BK-4-03 (X=NH, R$_1$=R$_2$=R$_4$=R$_5$=H and R$_3$=CF$_3$).
Figure 3:
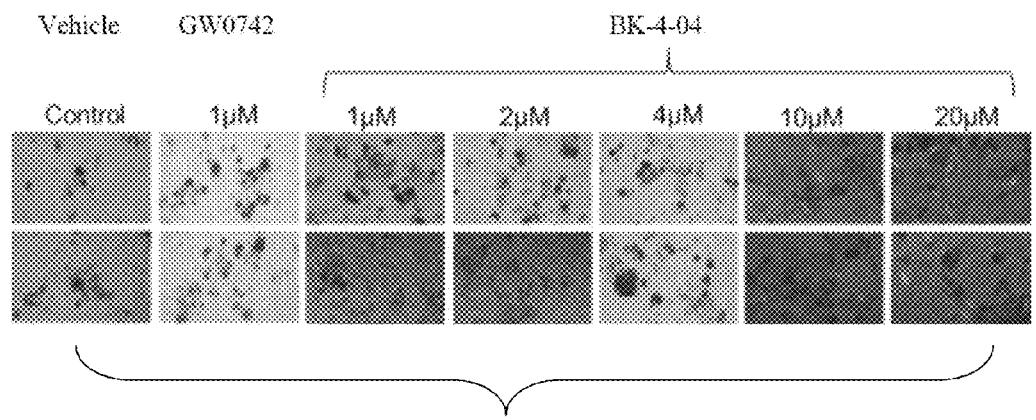
FIG. 3: Increased osteogenic formation from MSCs treated with BK-4-04 (X=S, R$_1$=R$_2$=R$_4$=R$_5$=H and R$_3$=CF$_3$).
Figure 4:
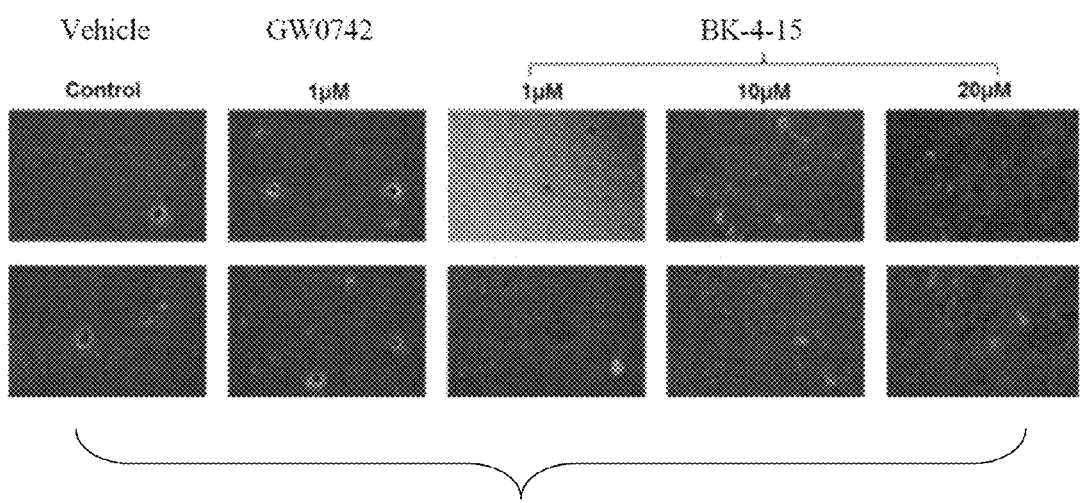
FIG. 4: Increased osteogenic formation from MSCs treated with BK-4-15 (X=NCH$_3$, R$_1$=R$_2$=R$_4$=R$_5$=H and R$_3$=CF$_3$).

Various embodiments are described herein in the context of PPARδ and 20-OH-PGE$_2$ analogues, and methods of using the same. Those of ordinary skill in the art will realize that the following detailed description of the embodiments is illustrative only and not intended to be in any way limiting. Other embodiments will readily suggest themselves to such skilled persons having the benefit of this disclosure. Reference to an "embodiment," "aspect," or "example" herein indicate that the embodiments of the invention so described may include a particular feature, structure, or characteristic, but not every embodiment necessarily includes the particular feature, structure, or characteristic. Further, repeated use of the phrase "in one embodiment" does not necessarily refer to the same embodiment, although it may.

In the interest of clarity, not all of the routine features of the implementations or processes described herein are shown and described. It will, of course, be appreciated that in the development of any such actual implementation, numerous implementation-specific decisions will be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking for those of ordinary skill in the art having the benefit of this disclosure.

Definitions

The term "PPAR" refers to Peroxisome Proliferator Activated Receptors, which are orphan receptors belonging to the steroid/retinoid receptor superfamily of ligand-activated transcription factors. Three mammalian PPARs have been identified, termed PPARα, PPARγ, and PPARδ. PPARs regulate expression of target genes by binding to DNA response elements as heterodimers with the retinoid X receptor.

The term "pharmacophoric mimic" refers to a compound or functional group having the steric and electronic features necessary for molecular recognition by a biological macromolecule similar to that of another compound or functional group.

The term "alkyl" as used herein refers to monovalent alkyl groups, which are saturated hydrocarbons, preferably having from 1 to 10 carbon atoms and more preferably 1 to 6 carbon atoms. This term is exemplified by groups such as methyl, ethyl, n-propyl, iso-propyl, n-butyl, iso-butyl, n-hexyl, and the like.

Unless stereochemistry is specifically indicated, all stereoisomers of the compounds herein are included, as pure compounds as well as mixtures thereof.

Some of the crystalline forms for the compounds may exist as polymorphs and as such are included. In addition, some of the compounds herein may form solvates with water (i.e., hydrates) or common organic solvents, which are also included.

Protected forms of the compounds herein are further included. A variety of protecting groups are possible.

Prodrugs of the compounds herein are included. In general, such prodrugs are functional derivatives of the compounds that are readily convertible in vivo into the required compound. Thus, in the methods of treatment, the term "administering" includes the treatment of the various disorders described with the compound specifically disclosed or with a compound which may not be specifically disclosed, but which converts to the specified compound in vivo after administration to a subject in need thereof. A simple example of a prodrug, not meant to be limiting in any manner, would be an alkyl ester of the acidic groups container at $R^3$ within Formula I or at R within Formula II.

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine. Solvates are sometimes termed "pseudopolymorphs." The term "hydrate" refers to a solvate with water.

The term "racemate" refers to a mixture that contains an equal amount of enantiomers.

It will be appreciated by one of ordinary skill in the art that asymmetric centers may exist in any of the compounds disclosed herein. Thus, the compounds may be in the form of an individual enantiomer, diastereomer, or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

It will also be appreciated that any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents. For purposes of explanation herein, heteroatoms such as nitrogen may have hydrogen substituents and/or any permissible substituents of organic compounds described herein which satisfy the valencies of the heteroatoms. Furthermore, there is not any intention to be limited in any manner by the permissible substituents.

General Description

Mesenchymal stem cells are stem cells that can develop into connective tissue throughout the body, such as bone, fat, and cartilage. The present disclosure is aimed at directing mesenchymal stem cells toward osteogenesis or chondrogenesis as opposed to adipogenesis, thereby inducing bone formation over fat formation. The compounds, compositions, and methods described herein are thus useful in the treatment and/or prevention of musculoskeletal disorders such as osteoporosis, osteoarthritis, metabolic and bone disease, as well as for fracture management and prosthetic integration.

Further provided herein is a method of inducing osteogenesis, the method comprising: contacting a mammalian cell with an effective amount of at least one pharmaceutical composition described herein, whereby the mammalian cell differentiates into a cell of an osteoblast lineage, or whereby the mammalian cell differentiates into a cell of a chondroblast lineage.

In certain embodiments, the mammalian cell is an in vivo mammalian cell.

In certain embodiments, the mammalian cell is a mesenchymal stem cell.

In certain embodiments, the stem cell is isolated from a primate.

In certain embodiments, the primate is a human.

In certain embodiments, the step of contacting is by oral administration of the compound to the mammal.

In certain embodiments, the step of contacting is by intravenous administration of the compound to the mammal.

In certain embodiments the step of contacting is by subcutaneous administration of the compound to the mammal.

In certain embodiments, the method further comprises detecting differentiation of the mammalian cell into an osteocyte cell of an osteoblast lineage.

In certain embodiments, the method further comprises detecting differentiation of the mammalian cell into a chondrocyte cell of a chondroblast lineage.

In certain embodiments, wherein the mammalian cell is attached to a solid support.

In certain embodiments, the solid support is a three dimensional matrix.

In certain embodiments, the solid support is a planar surface.

Further provided herein is a method of treating a bone disorder, comprising: contacting a mammalian cell with a pharmaceutical composition as described herein, whereby the mammalian cell differentiates into a cell of an osteoblast lineage, wherein the bone disorder is associated with defective osteoblasts.

In certain embodiments, the bone disorder is osteoporosis.

In certain embodiments, the method further comprises administering the cell of an osteoblast lineage to an individual with the disorder, thereby treating the disorder.

In certain embodiments, the administration is by surgical implantation.

Further provided herein is a method of treating a cartilage disorder, comprising: contacting a mammalian cell with a pharmaceutical composition as described herein, whereby the mammalian cell differentiates into a cell of a chondroblast lineage, wherein the bone disorder is associated with defective chondroblasts.

In certain embodiments, the cartilage disorder is one or more of: injury to articular cartilage; osteoarthritis; costochondritis; herniation; achondroplasia; relapsing polychondritis; benign or non-cancerous chondroma; and, malignant or cancerous chondrosarcoma.

Further provided herein is a method for inducing chondrogenesis leading to cartilage formation or chondrogenesis leading to cartilage formation that further mediates formation of new bone tissue in a vertebrate, the method comprising administering a therapeutically effective amount of a pharmaceutical composition as described herein to the vertebrate.

In certain embodiments, the administration is local or systemic.

Further provided herein is a method for promoting chondrogenesis at a site of skeletal surgery in a vertebrate, the method comprising delivering a pharmaceutical composition as described herein at the site of skeletal surgery wherein such delivery induces chondrogenesis leading to cartilage formation at the site or chondrogenesis leading to cartilage formation that further mediates formation of new bone tissue at the site.

In accordance with the present disclosure, there are provided herein compounds that are analogs of PPARδ and 20-OH-PGE$_2$. The analog compounds serve as either agonists to compounds that promote bone formation or antagonists to compounds that induce adipogenesis.

Example

Osteogenesis

Human bone marrow-derived mesenchymal stem cells (MSCs) were taken through 2-3 passages and distributed across a 24 well plate at a density of $1 \times 10^5$ cells/cm$^2$. The plates were cultured in α-MEM with 20% FBS for 1 day at 37° C. On day 2 the medium was switched to osteogenic media (Stem X-Vivo, R&D System, Minneapolis, Minn.) containing 10% FBS plus 50 µg/ml ascorbic acid and 3 mM β-glycerol-phosphate. MSCs were cultured in the osteogenic medium without (vehicle negative control) or with test agents at 1, 2, 4, 10 or 20 µM supplied every 2nd day for 21 days. GW 0427 (standard PPAR ligand as positive control) was delivered by the same regimen on every plate to account for experimental variation.

Quantification of Osteoblast Mineralization

Plates were washed twice with ice-cold PBS and incubated in 50 mM Tris-HCl (pH 7.6). The cells were treated with 2% Alizarin Red S (pH 4.2) for 10 min and then washed with distilled water. Stained cells were visualized by phase-contrast microscopy to determine cell morphology and to verify the presence of mineralized nodules (red images). The intensities of the images were assessed by Image-Pro Analyzer (Media Cybernetics, Inc., Bethesda, Md.).

Results

Representative results for test agents having O, NH, S and N(CH$_3$) X-linkages are respectively displayed in FIGS. 1-4.

Figure 5:
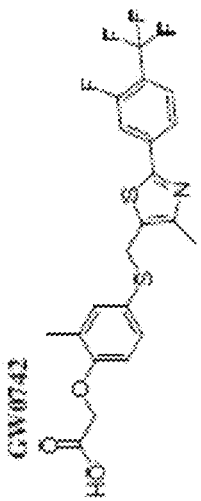
FIG. 5: Table I—Structure of GW0742, chemical template for test agents, and summary of results for several compounds tested in the MSC assay with concomitant assessment of fat cell formation.
Figure 5:
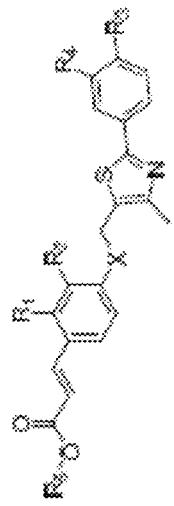
Figure 6:
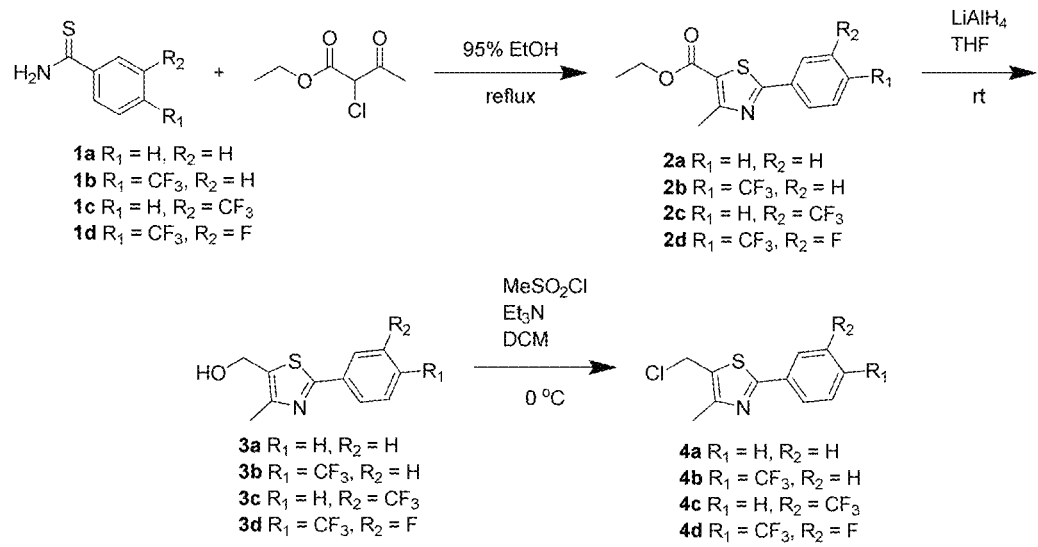
FIG. 6: Scheme 1—Eastern half synthesis.
Figure 7:
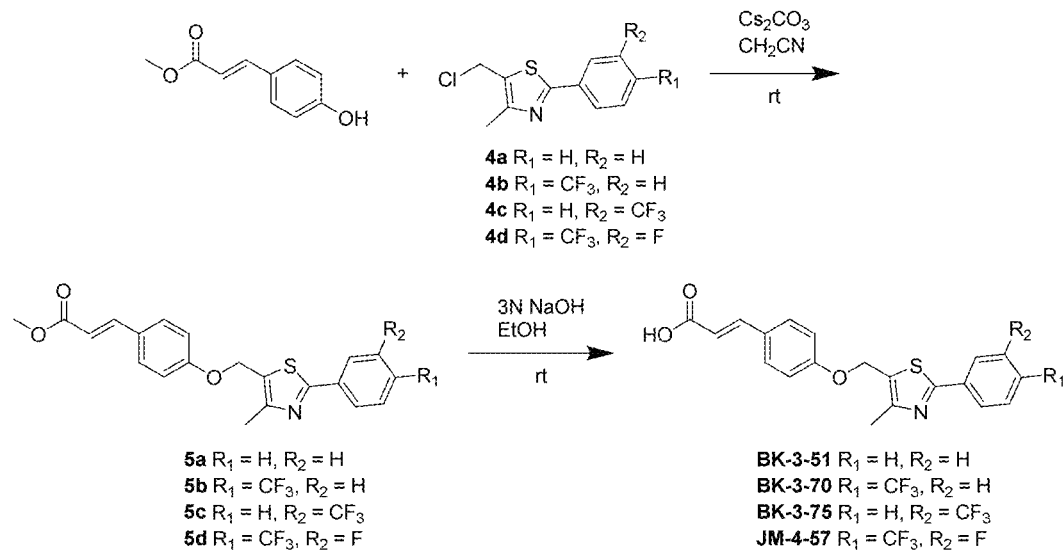
FIG. 7: Scheme 2—O-series synthesis.
Figure 8:
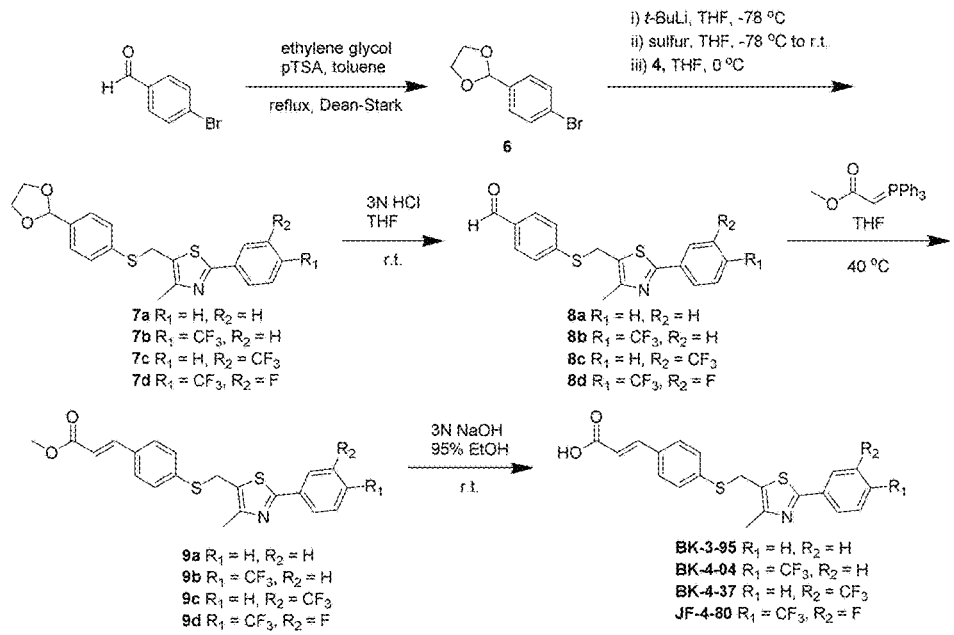
FIG. 8: Scheme 3—S-series synthesis.
Figure 9:
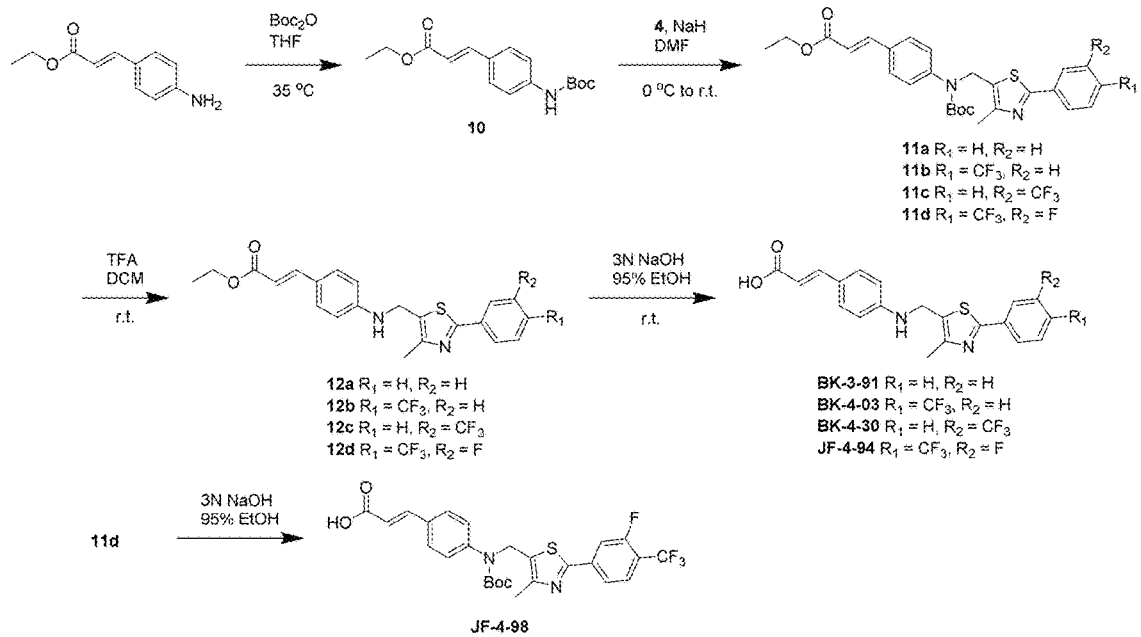
FIG. 9: Scheme 4—NH-series synthesis.
Figure 10:
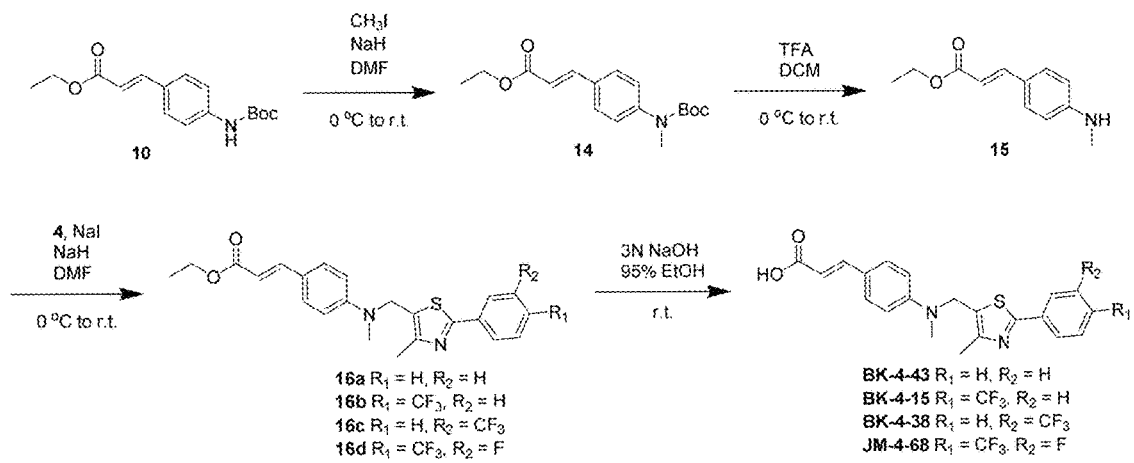
FIG. 10: Scheme 5—N-Methyl synthesis.
Figure 11:
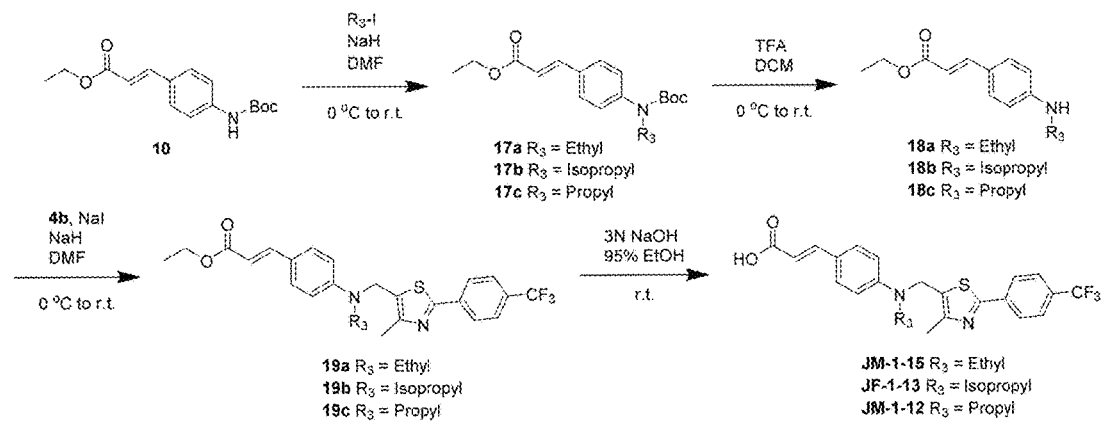
FIG. 11: Scheme 6—N-Alkyl synthesis.
Figure 12:
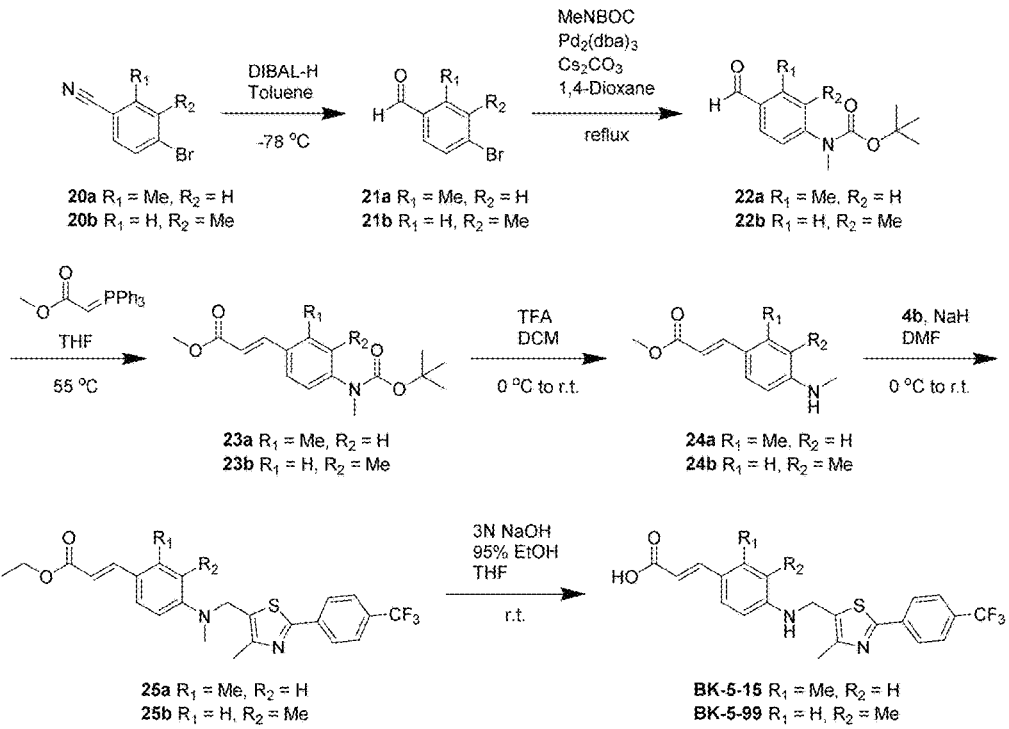
FIG. 12: Scheme 7—R$_1$ & R$_2$ Western Ring Analogs Group #1.
Figure 13:
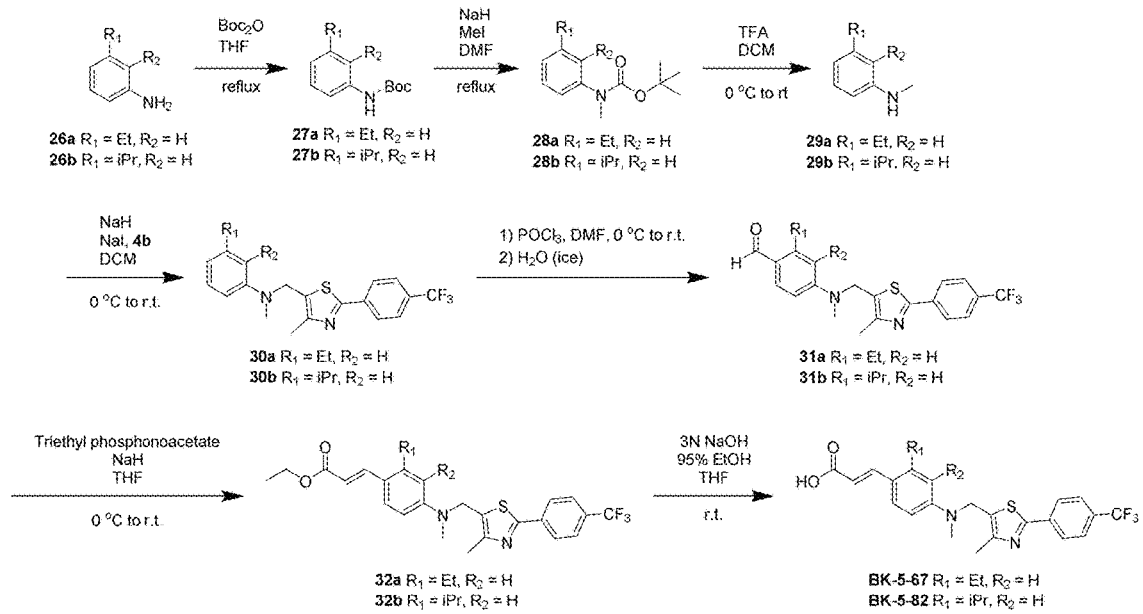
FIG. 13: Scheme 8—R$_1$ & R$_2$ Western Ring Analogs Group #2.
Figure 14:
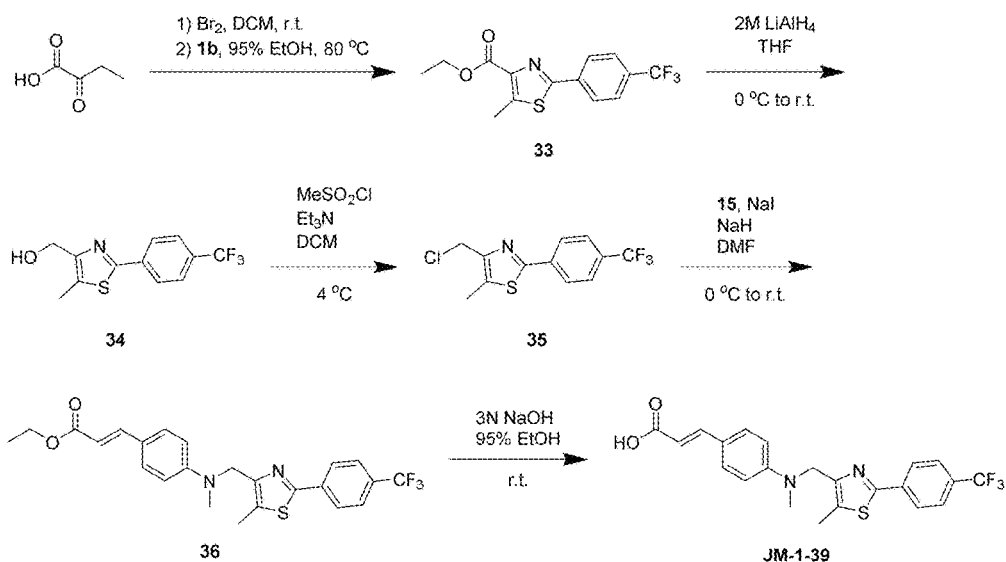
FIG. 14: Scheme 9—Central Heterocycle "Thiazole-flip".
Figure 15:
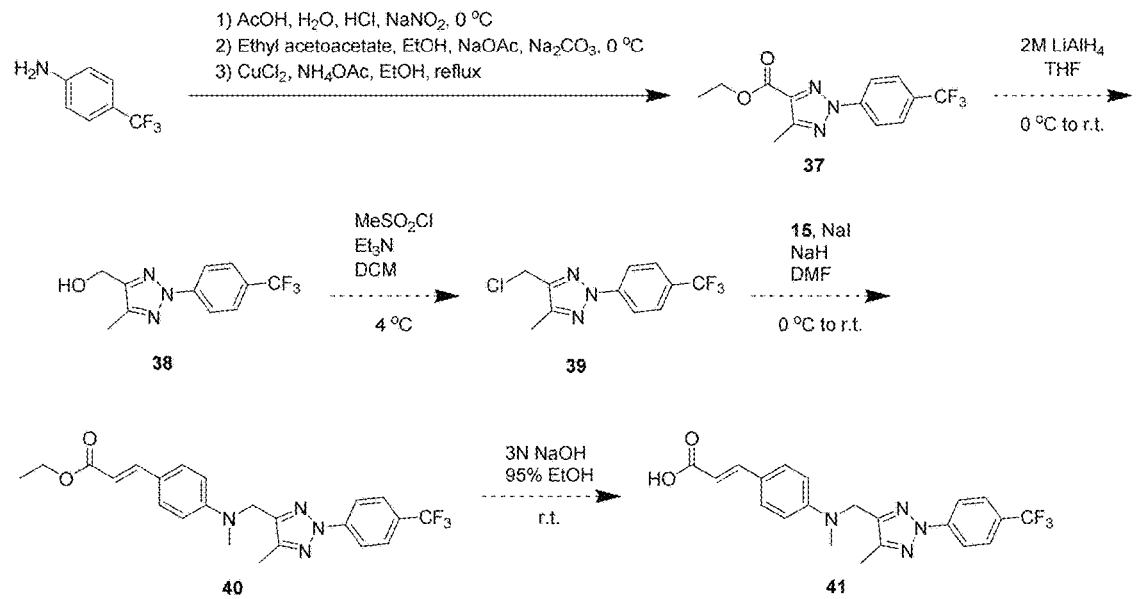
FIG. 15: Scheme 10—Central Heterocycle Triazole Synthesis.
Figure 16:
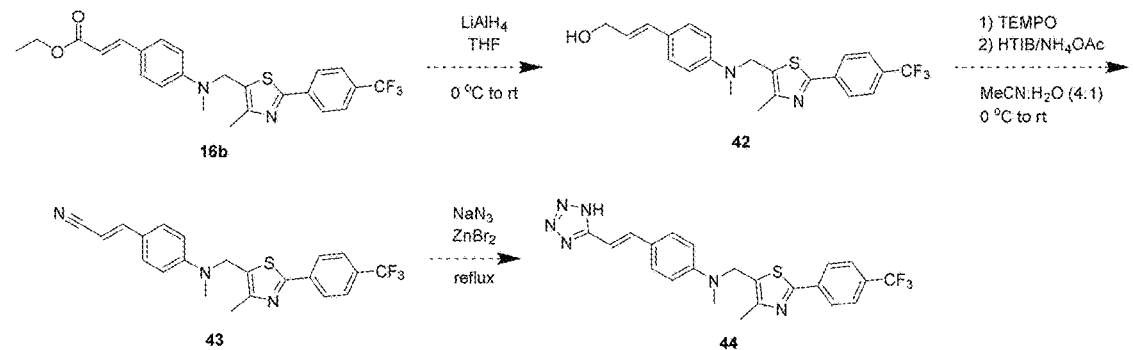
FIG. 16: Scheme 11—Carboxylic Acid Bioisostere 44.
Figure 17:
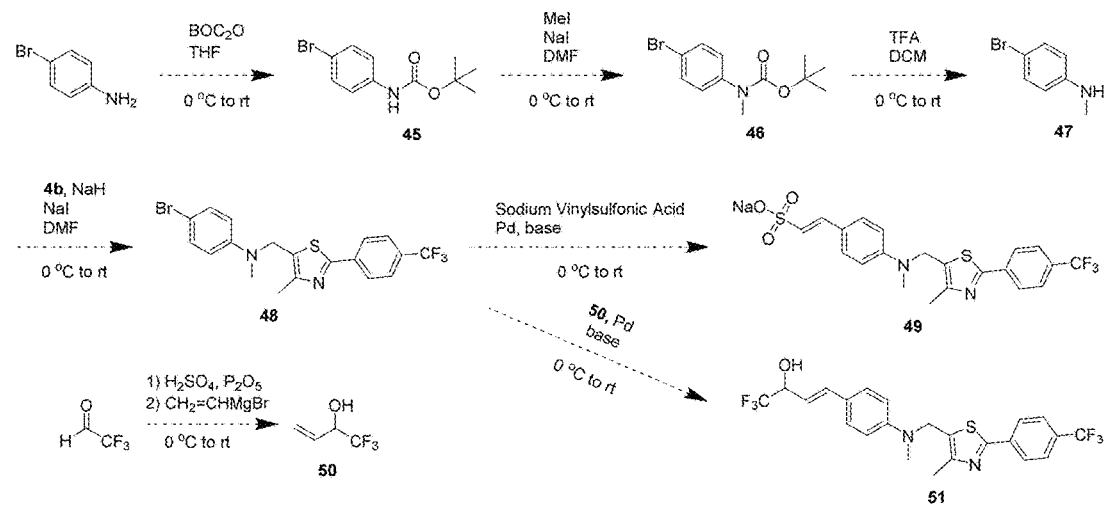
FIG. 17: Scheme 12—Carboxylic Acid Bioisosteres 49 and 51.
Figure 18:
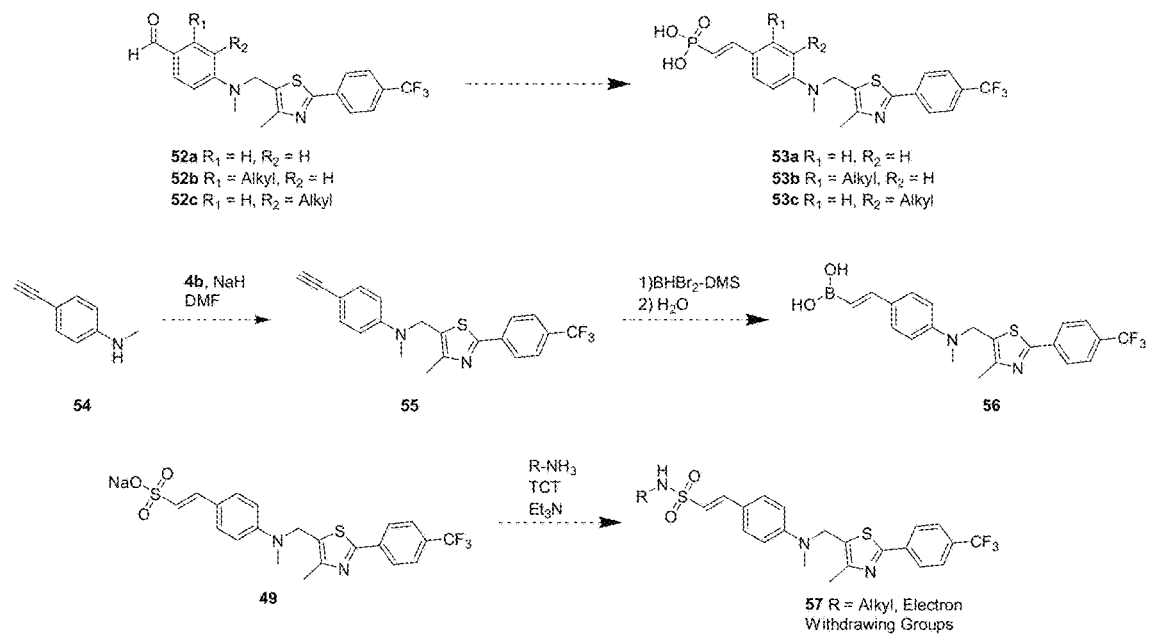
FIG. 18: Scheme 13—Carboxylic Acid Bioisosteres 53, 56, and 57 Syntheses.
Figure 19:
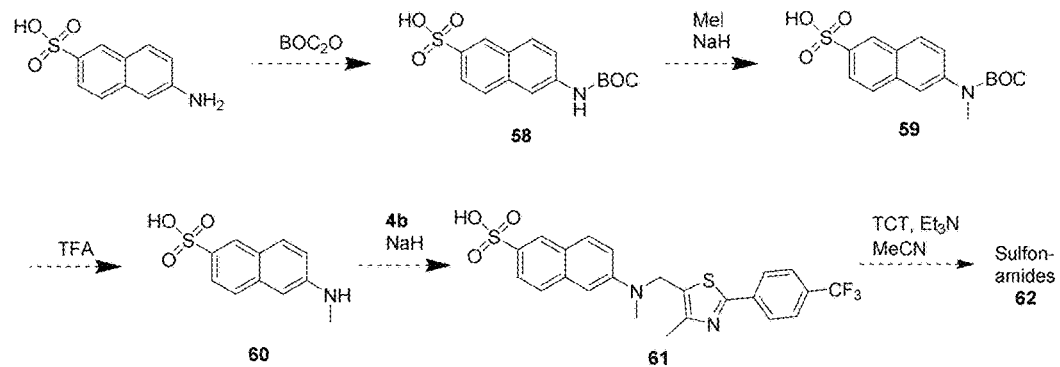
FIG. 19: Scheme 14—Naphthalene Sulfonic Acid 61 and Amide 61 Syntheses.

FIG. 5—Table I provides a structural key for these compounds and a summary of biological data for several additional members within each of the four linkage types. FIG. 5—Table I shows the structure of GW0742, chemical template for test agents, and summary of results for several compounds tested in the MSC assay with concomitant assessment of fat cell formation.

Explanatory comments: 'AD' indicates formation of fat cells analogous to those in adipose tissue; 'OS' indicates formation of mineral deposits indicative of osteogenesis ('OS'); For both observations, generalized scaling was '0' for none observed, '+' for modest, '++' for moderate, '+++' for significant, and '++++' for extensive; The term 'Toxic' indicates that cell viability was affected by the test agent such that assignment of a scale for either AD or OS became compromised; and, Blank entries indicate that the corresponding dose either was not tested or assessed, the latter generally being due to the observation of toxicity from the preceding dose.

Additional notes: A mix of fat and osteogenic effects is regarded as acceptable as long as bone predominates during dose progression, e.g. BK-4-15 exhibits the most preferred profile while the profile for BK-4-30 is not as suitable. While GW0742 initially demonstrates such a preference, its OS activity typically decreased as its dose range was continued to 10 and 20 uM such that all of its estimated, averaged effects at these higher doses have been placed in parentheses.

The chemical synthesis and reaction schemes are shown in FIGS. 6-19. Note that the numbering of R groups does not correspond to the template depicted in FIG. 5 Table I. The final compound designations, however, are identical.

It is intended that any of the compounds disclosed herein could be used in a medication, a food additive, an injection, or a surgical implant designed to treat, ameliorate, or modify, osteoporosis, osteoarthritis, metabolic bone disease, and/or fracture management problems. The compounds of the present disclosure could be used to enhance the natural pathways to direct a patient's own mesenchymal stem cells toward bone and cartilage formation over adipose formation, thereby preventing and/or treating these underlying conditions. The compounds could also be incorporated into a pharmaceutical composition, or could be used to treat isolated stem cells that are then administered to a patient in need thereof.

Pharmaceutical Compositions

Pharmaceutical compositions of the present disclosure comprise an effective amount of a compound disclosed herein, and/or additional agents, dissolved or dispersed in a pharmaceutically acceptable carrier. The phrases "pharmaceutical" or "pharmacologically acceptable" refers to molecular entities and compositions that produce no adverse, allergic or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In most cases, the form must be sterile and must be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it is preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed is known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroethylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits

It is further intended the compounds disclosed herein could be packaged in the form of a kit containing a single or separate containers. Many embodiments of such kits are possible. For instance, a kit could house two containers, the first container comprising a compound of Formula I, and the second container comprising a compound of Formula II. By way of further non-limiting example, a kit could have a first container housing a solution comprising one or more compounds of Formula I and Formula II, and a second container comprising a syringe configured to inject the solution. As another example, a kit for the preparation of a pharmaceutical composition could have a first container housing one or more compounds of Formula I and Formula II, and a second container housing a pharmaceutically acceptable carrier, excipient, diluent, or adjuvant. Many other variations and embodiments of such kits are envisioned. The kits typically further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Chemical Syntheses

4-Methyl-2-phenylthiazole-5-carboxylic acid ethyl ester (2a)

To a suspension of thiobenzamide 1a (6.05 g, 0.044 mol) in 95% ethanol was added ethyl 2-chloroacetoacetate (6.10 mL, 0.044 mol) and the mixture was stirred at reflux temperature for 26 hours. The reaction mixture was concentrated under reduced pressure and the resulting residue was suspended in ice-cold hexane and stirred for 20 minutes. The suspension was filtered and 2a collected as a cream-colored solid (7.434 g, 0.030 mol, 68.3%). TLC $R_f$ (25% EtOAc/Hexane)=0.63. Mp 84-87° C. $^1$H NMR (CDCl$_3$, 600 MHz): δ ppm 8.19 (2H, d, J=7.32 Hz), 7.56 (1H, t, J=7.32 Hz), 7.53 (2H, t, J=7.08 Hz), 4.41 (2H, q, J=7.14 Hz), 2.94 (3H, s), 1.41 (3H, t, J=7.14 Hz). $^{13}$C NMR (CDCl$_3$, 150 MHz): δ (ppm) 171.25, 161.07, 157.83, 133.21, 129.82, 128.10, 122.55, 62.37, 16.29, 14.52 ppm.

4-Methyl-2-phenyl-5-thiazolemethanol (3a)

To a stirred solution of ethyl ester 2a (0.304 g, 1.237 mmol) in anhydrous THF (1 mL) at 0° C. was added 2M lithium aluminum hydride solution in THF (1.24 ml, 2.48 mmol). The resulting mixture was stirred under argon at 0° C. for 1.5 hours. The reaction mixture was quenched by the careful addition of 0.5 ml of water, followed by 2.5 ml of ethyl acetate and 0.92 g of anhydrous sodium sulfate. The mixture was stirred for 15 minutes and was filtered and concentrated under reduced pressure to give 3a as a light-yellow solid (0.215 g, 1.053 mmol, 85.1%). TLC $R_f$(25% EtOAc/Hexane)=0.11. Mp 101-102° C. $^1$H NMR (CDCl$_3$, 600 MHz): δ ppm 7.88 (2H, d, J=7.92 Hz), 7.41 (3H, m), 4.79 (2H, s), 2.94 (1H, s), 2.41 (3H, s).

5-Chloromethyl-4-methyl-2-phenyl-thiazole (4a)

To a stirred solution of alcohol 3a (4.095 g, 0.019 mol) in anhydrous dichloromethane (100 ml) was added triethylamine (5.50 ml, 0.039 mol). The resulting mixture was cooled to 4° C. and methanesulfonyl chloride (2.30 ml, 0.029 mol) was slowly added. The mixture was stirred at 4° C. for 24 hours and then diluted with 100 ml dichloromethane, washed with saturated $NaHCO_3$ solution, water, brine, dried with $Na_2SO_4$, and concentrated. The residue was purified by column chromatography on silica gel with 10% ethyl acetate/hexane to give 4a as a light yellow solid (2.850 g, 0.013 mol, 64.0%). TLC $R_f$ (25% EtOAc/Hexane)=0.57. Mp 89-90° C. $^1H$ NMR ($CDCl_3$, 600 MHz): δ ppm 7.90 (2H, m), 7.43 (3H, m), 4.80 (2H, s), 2.50 (3H, s).

Methyl 4-[[4-methyl-2-phenylthiazol-5-yl]methyl]methoxycinnamate (5a)

To a stirred solution of Methyl 4-Hydroxycinnamate (0.142 g, 0.797 mmol) and chloromethyl 4a (0.150 g, 0.670 mmol) in anhydrous acetonitrile (5 ml) was added cesium carbonate with partial solubility. The resulting mixture was stirred for 24 hours at room temperature at which TLC showed that the chloromethyl 4a had been consumed. The reaction mixture was concentrated and the residue was dissolved in ethyl acetate and washed with water, brine, dried with $Na_2SO_4$, and concentrated. Column chromatography on silica gel failed to give a pure product and the crude white solid 5a collected was moved to the next step without further purification.

4-[[4-Methyl-2-phenylthiazol-5-yl]methyl]methoxycinnamic Acid (BK-3-51)

To a stirred solution of methyl ester 5a was added dropwise 3N NaOH. After 20 hours, the mixture was acidified with 1N HCl to a pH=1-2 and concentrated. The residue was suspended in ethyl acetate and washed with water and brine. The aqueous phase was extracted with a separate portion of ethyl acetate and the organic phases were combined, dried with $Na_2SO_4$ and concentrated. The residue was purified by column chromatography on silica gel to give BK-3-51 as a white solid (0.061 g, 0.173 mmol, 41.7%). TLC $R_f$ (50% EtOAc/Hexane)=0.17. Mp 209-211° C. $^1H$ NMR (Acetone-d6, 600 MHz): δ ppm 7.91 (2H, m), 7.67 (2H, d, J=8.76 Hz), 7.55 (1H, d, J=15.96 Hz), 7.49 (3H, m), 7.09 (2H, d, J=8.82 Hz), 6.41 (1H, d, J=15.96 Hz), 5.38 (2H, s), 2.46 (4H, s).

Ethyl 4-Methyl-2-[4-(trifluoromethyl)phenyl]-thiazole-5-carboxylate (2b)

In analogy to the procedure described in example 2a, 4-(trifluoromethyl)thiobenzamide 1a (1.065 g, 5.190 mmol) was treated with ethyl-2-chloroacetoacetate in 95% ethanol to give 2b as a cream-colored solid (1.148 g, 3.644 mmol, 70.2%). TLC $R_f$ (25% EtOAc/Hexane)=0.69. Mp 89-89.5° C. $^1H$ NMR ($CDCl_3$, 600 MHz): δ ppm 8.10 (2H, d, J=8.04 Hz), 7.73 (2H, d, J=8.16 Hz), 4.39 (2H, q, J=7.14 Hz), 2.81 (3H, s), 1.42 (3H, t, J=7.08 Hz). $^{13}C$ NMR ($CDCl_3$, 150 MHz): δ (ppm) 167.87, 162.17, 161.38, 136.16, 132.59 (q, $^2J_{FC}$=33 Hz), 127.18, 126.22 (m), 123.90 (q, $^1J_{FC}$=270 Hz), 123.13, 61.61, 17.67, 14.47. Anal. Calcd for $C_{14}H_{12}F_3NO_2S$ (with $0.2H_2O$ mol per target): C, 52.73; H, 3.92; N, 4.39. Found: C, 52.59; H, 3.85; N, 4.71.

4-Methyl-2-[4-(trifluoromethyl)phenyl]-thiazole-5-methanol (3b)

In analogy to the procedure described in example 3a, ethyl ester 2b (1.320 g, 4.190 mmol) was treated with 2M $LiAlH_4$ solution in THF to give 3b as a yellow solid (0.904 g, 3.308 mmol, 79.0%). TLC $R_f$ (25% EtOAc/Hexane)=0.16. Mp 121.5-122° C. $^1H$ NMR ($CDCl_3$, 600 MHz): δ ppm 8.02 (2H, d, J=8.04 Hz), 7.69 (2H, d, J=8.16 Hz), 4.86 (2H, s), 2.48 (3H, s). $^{13}C$ NMR ($CDCl_3$, 150 MHz): δ (ppm) 164.33, 150.91, 136.74, 132.57, 131.63 (q, $^2J_{FC}$=33 Hz), 126.66, 126.08 (m), 124.03 (q, $^1J_{FC}$=270 Hz), 57.04, 15.27.

5-Chloromethyl-4-methyl-2-[4-(trifluoromethyl)phenyl]-thiazole (4b)

In analogy to the procedure described in example 4a, alcohol 3b (0.883 g, 3.231 mmol) was treated with methanesulfonyl chloride and triethylamine in dry DCM to give 4b as a light yellow solid (0.790 g, 2.708 mmol, 83.8%). TLC $R_f$ (25% EtOAc/Hexane)=0.53. Mp 68.5-69° C. $^1H$ NMR ($CDCl_3$, 600 MHz): δ ppm 8.03 (2H, d, J=8.10 Hz), 7.70 (2H, d, J=8.16 Hz), 4.81 (2H, s), 2.52 (3H, s). $^{13}C$ NMR ($CDCl_3$, 150 MHz): δ (ppm) 165.02, 153.25, 136.51, 131.92 (q, $^2J_{FC}$=33 Hz), 129.06, 126.77, 126.12 (m), 123.99 (q, $^1J_{FC}$=270 Hz), 37.32, 15.20. Anal. Calcd for $C_{12}H_9ClF_3NS$: C, 49.41; H, 3.11; N, 4.80. Found: C, 49.43; H, 3.22; N, 4.75.

Methyl 4-[[4-methyl-2-[4-(trifluoromethyl)phenyl]-thiazol-5-yl]methyl]methoxy]cinnamate (5b)

In analogy to the procedure described in example 5a, chloromethyl 4b (0.331 g, 1.135 mmol) and Methyl4-Hydroxycinnamate were treated with cesium carbonate in anhydrous acetonitrile to give 5b as a light yellow solid (0.365 g, 0.842 mmol, 74.3%). TLC $R_f$ (25% EtOAc/Hexane)=0.32. Mp 153-155° C. $^1H$ NMR ($CDCl_3$, 600 MHz): δ ppm 8.04 (2H, d, J=8.1 Hz), 7.70 (2H, d, J=8.2 Hz), 7.68 (1H, d, J=16.0 Hz), 7.52 (2H, d, J=8.6 Hz), 7.00 (2H, d, J=8.7 Hz), 6.36 (1H, d, J=16.0 Hz), 5.24 (2H, s), 3.8 (3H, s), 2.54 (3H, s). $^{13}C$ NMR ($CDCl_3$, 150 MHz): δ (ppm) 167.79, 165.13, 159.81, 152.49, 144.33, 136.67, 131.80 (q, $^2J_{FC}$=33 Hz), 129.96, 128.20, 127.61, 126.75, 126.10 (m), 124.02 (q, $^1J_{FC}$=270 Hz), 116.08, 115.38, 62.29, 51.82, 15.57. Anal. Calcd for $C_{22}H_{18}F_3NO_3S$: C, 60.96; H, 4.19; N, 3.23. Found: C, 60.79; H, 4.36; N, 3.15.

4-[[4-methyl-2-[4-(trifluoromethyl)phenyl]-thiazol-5-yl]methyl]methoxycinnamic Acid (BK-3-70)

In analogy to the procedure described in example BK-3-51, methyl ester 5b (0.202 g, 0.466 mmol) was treated with 3N NaOH in 95% ethanol to give BK-3-70 as a white solid (0.048 g, 0.114 mmol, 24.6%). TLC $R_f$ (50% EtOAc/Hexane)=0.15. Mp 224-225° C. $^1H$ NMR (Acetone-d6, 600 MHz): δ ppm 8.18 (2H, d, J=8.1 Hz), 7.85 (2H, d, J=8.2 Hz), 7.67 (2H, d, J=8.8 Hz), 7.63 (1H, d, J=16.0 Hz), 7.13 (2H, d, J=8.8 Hz), 6.41 (1H, d, J=16.0 Hz), 5.44 (2H, s), 2.53 (3H, s). $^{13}C$ NMR (Acetone-d6, 150 MHz): δ ppm 167.94, 164.82, 160.83, 153.28, 144.93, 137.90, 131.71 (q, $^2J_{FC}$=33 Hz), 130.75, 129.46, 128.87, 127.50, 126.93 (m), 125.11 (q, $^1J_{FC}$=270 Hz), 117.15, 116.24, 62.85, 15.42. $^{19}F$ NMR (Acetone-d6, 376 MHz): δ ppm −63.67 (3F, s). Anal. Calcd for $C_{21}H_{16}F_3NO_3S$: C, 60.14; H, 3.85; N, 3.34. Found: C, 60.12; H, 3.85; N, 3.31.

Ethyl 4-Methyl-2-[3-(trifluoromethyl)phenyl]-thiazole-5-carboxylate (2c)

In analogy to the procedure described in example 2a, 3-(trifluoromethyl)thiobenzamide 1c (2.00 g, 9.75 mmol) was treated with ethyl-2-chloroacetoacetate in 95% ethanol to give 2c as a cream-colored solid (2.103 g, 6.677 mmol, 68.5%). TLC $R_f$ (25% EtOAc/Hexane)=0.63. Mp 90-91° C. $^1H$ NMR (CDCl$_3$, 600 MHz): δ ppm 8.26 (1H, s), 8.14 (1H, d, J=7.86 Hz), 7.73 (1H, d, J=7.80 Hz), 7.60 (1H, dd, $J_1$=7.86 Hz, $J_2$=7.80 Hz), 4.38 (2H, q, J=7.14 Hz), 2.81 (3H, s), 1.41 (3H, t, J=7.14 Hz). $^{13}C$ NMR (CDCl$_3$, 150 MHz): δ (ppm) 167.94, 162.18, 161.34, 133.83, 131.80 (q, $^2J_{FC}$=32.7 Hz), 130.03, 129.78, 127.48 (q, $^3J_{FC}$=3.5 Hz), 123.81 (q, $^3J_{FC}$=271 Hz), 123.69 (q, $^3J_{FC}$=3.5 Hz), 122.84, 61.59, 17.65, 14.46. Anal. Calcd for $C_{14}H_{12}F_3NO_2S$: C, 53.33; H, 3.84; N, 4.44. Found: C, 53.05; H, 3.93; N, 4.54.

4-Methyl-2-[3-(trifluoromethyl)phenyl]-thiazole-5-methanol (3c)

In analogy to the procedure described in example 3a, ethyl ester 2c (2.053 g, 6.516 mmol) was treated with 2M LiAlH$_4$ solution in THF to give 3c as a yellow solid (1.273 g, 4.658 mmol, 71.5%). TLC $R_f$ (25% EtOAc/Hexane)=0.16. Mp 58-60° C. $^1H$ NMR (CDCl$_3$, 600 MHz): δ ppm 8.19 (1H, s), 8.07 (1H, d, J=7.8 Hz), 7.66 (1H, d, J=7.8 Hz), 7.56 (1H, t, J=7.8 Hz), 4.87 (2H, s), 2.49 (3H, s). $^{13}C$ NMR (CDCl$_3$, 150 MHz): δ (ppm) 164.43, 150.67, 134.31, 132.36, 131.61 (q, $^2J_{FC}$=32.5 Hz), 129.63, 126.52 (q, $^3J_{FC}$=3.5 Hz), 123.92 (q, $^1J_{FC}$=271 Hz), 123.19 (q, $^3J_{FC}$=3.5 Hz), 56.95, 15.20.

5-Chloromethyl-4-methyl-2-[3-(trifluoromethyl) phenyl]thiazole (4c)

In analogy to the procedure described in example 4a, alcohol 3c (1.295 g, 4.739 mmol) was treated with methanesulfonyl chloride and triethylamine in dry DCM to give 4c as a light yellow solid (0.830 g, 2.846 mmol, 60.1%). TLC $R_f$ (25% EtOAc/Hexane)=0.61. Mp 43-44° C. $^1H$ NMR (CDCl$_3$, 600 MHz): δ ppm 8.19 (1H, s), 8.07 (1H, d, J=7.8 Hz), 7.68 (1H, d, J=7.8 Hz), 7.57 (1H, t, J=7.8 Hz), 4.81 (2H, s), 2.51 (3H, s). $^{13}C$ NMR (CDCl$_3$, 150 MHz): δ (ppm) 165.09, 153.16, 134.21, 131.68 (q, $^2J_{FC}$=33 Hz), 129.70, 129.67, 128.75, 126.78 (q, $^3J_{FC}$=3.6 Hz), 123.90 (q, $^1J_{FC}$=271 Hz), 123.30 (q, $^3J_{FC}$=3.6 Hz), 37.37, 15.21. Anal. Calcd for $C_{12}H_9ClF_3NS$: C, 49.41; H, 3.11; N, 4.80. Found: C, 49.46; H, 3.16; N, 4.91.

Ester 4-[[4-methyl-2-[3-(trifluoromethyl)phenyl]-thiazol-5-yl]methyl]methoxycinnamate (5c)

In analogy to the procedure described in example 5a, chloromethyl 4c (0.472 g, 1.618 mmol) and Methyl 4-Hydroxycinnamate were treated with cesium carbonate in anhydrous acetonitrile to give 5c as a white solid (0.551 g, 1.270 mmol, 80.5%). TLC $R_f$ (25% EtOAc/Hexane)=0.30. Mp 125-127° C. $^1H$ NMR (CDCl$_3$, 600 MHz): δ ppm 8.19 (1H, s), 8.09 (1H, d, J=7.7 Hz), 7.68 (1H, d, J=7.8 Hz), 7.67 (1H, d, J=16.0 Hz), 7.56 (1H, t, J=7.8 Hz), 7.51 (2H, d, J=8.6 Hz), 6.99 (2H, d, J=8.7 Hz), 5.24 (2H, s), 3.81 (3H, s), 2.54 (3H, s). $^{13}C$ NMR (CDCl$_3$, 150 MHz): δ (ppm) 167.81, 165.26, 159.79, 152.23, 144.34, 134.20, 131.66 (q, $^2J_{FC}$=32 Hz), 129.96, 129.72, 129.67, 128.19, 127.36, 126.72 (q, $^3J_{FC}$=3.9 Hz), 125.71 (q, $^1J_{FC}$=270 Hz), 123.31 (q, $^3J_{FC}$=3.5 Hz), 116.06, 115.39, 62.28, 51.81, 15.51. Anal. Calcd for $C_{22}H_{18}F_3NO_3S$ (with 0.4H$_2$O mol per target): C, 59.97; H, 4.30; N, 3.18. Found: C, 59.66; H, 4.29; N, 3.07.

4-[[4-methyl-2-[3-(trifluoromethyl)phenyl]-thiazol-5-yl]methyl]methoxycinnamic Acid (BK-3-75)

In analogy to the procedure described in example BK-3-51, methyl ester 5c (0.207 g, 0.477 mmol) was treated with 3N NaOH in 95% ethanol to give BK-3-75 as a white solid (0.138 g, 0.329 mmol, 69.0%). TLC $R_f$ (50% EtOAc/Hexane)=0.40. Mp 179.5-181° C. $^1H$ NMR (Acetone-d6, 600 MHz): δ ppm 8.29 (1H, s), 8.23 (1H, d, J=7.8 Hz), 7.83 (1H, d, J=7.8 Hz), 7.76 (1H, t, J=7.8 Hz), 7.69 (2H, d, J=8.7 Hz), 7.65 (1H, d, J=16.0 Hz), 7.14 (2H, d, J=8.7 Hz), 6.43 (1H, d, J=16.0 Hz), 5.46 (2H, s), 2.54 (3H, s). $^{13}C$ NMR (Acetone-d6, 150 MHz): δ ppm 167.93, 164.81, 160.85, 153.12, 145.02, 135.37, 131.73 (q, $^2J_{FC}$=32 Hz), 131.14, 130.77, 130.70, 129.09, 128.85, 127.27 (q, $^3J_{FC}$=3.3 Hz), 125.01 (q, $^1J_{FC}$=270 Hz), 123.11 (q, $^3J_{FC}$=3.5 Hz), 117.05, 116.24, 62.86, 15.42. $^{19}F$ NMR (Acetone-d6, 376 MHz): δ ppm −63.76 (s, 3F). Anal. Calcd for $C_{21}H_{16}F_3NO_3S$: C, 60.14; H, 3.85; N, 3.34. Found: C, 59.96; H, 3.89; N, 3.30.

Ethyl 4-Methyl-2-[3-fluoro-4-(trifluoromethyl)phenyl]thiazole-5-carboxylate (2d)

In analogy to the procedure described in example 2a, 3-fluoro-4-(trifluoromethyl)thiobenzamide 1d (1.606 g, 7.195 mmol) was treated with ethyl-2-chloroacetoacetate in 95% ethanol to give 2d as a cream-colored solid (1.657 g, 4.971 mmol, 69.1%). TLC $R_f$ (25% EtOAc/Hexane)=0.72. Mp 101-102° C. $^1H$ NMR (CDCl$_3$, 600 MHz): δ ppm 7.86 (1H, d, J=10.9 Hz), 7.82 (1H, d, J=7.7 Hz), 7.70 (1H, t, J=7.7 Hz), 4.40 (2H, q, J=7.1 Hz), 2.80 (3H, s), 1.41 (3H, t, J=7.1 Hz). $^{13}C$ NMR (CDCl$_3$, 150 MHz): δ ppm 166.23, 161.97, 161.43, 160.16 (d, $^1J_{FC}$=254 Hz), 138.56 (d, $^4J_{FC}$=8.2 Hz), 128.16 (q, $^2J_{FC}$=3.9 Hz), 123.75, 122.39 (q, $^1J_{FC}$=271 Hz), 122.34 (d, $^3J_{FC}$=3.9 Hz), 120.20 (dq, $^2J_{FC}$=33 Hz, $^2J_{FC}$=12 Hz), 115.07 (d, $^2J_{FC}$=23 Hz), 67.74, 17.62, 14.45. $^{19}F$ NMR (CDCl$_3$, 376 MHz): δ ppm −61.74 (3F, s), −113.07 (1F, s). Anal. Calcd for $C_{14}H_{11}F_4NO_2S$: C, 50.45; H, 3.33; N, 4.20. Found: C, 50.47; H, 3.32; N, 4.24.

5-Hydroxymethyl-4-methyl-2-[3-fluoro-4-(trifluoromethyl)phenyl]thiazole (3d)

In analogy to the procedure described in example 3a, ethyl ester 2d (4.640 g, 13.92 mmol) was treated with 2M LiAlH$_4$ solution in THF to give 3d as a yellow solid (2.988 g, 10.26 mmol, 73.7%). TLC $R_f$ (25% EtOAc/Hexane)=0.21 Mp 158-159° C. $^1H$ NMR (CDCl$_3$, 600 MHz): δ ppm 7.79 (1H, d, J=11.2 Hz), 7.75 (1H, d, J=8.3 Hz), 7.65 (1H, t, $J_1$=7.6 Hz, $J_2$=7.7 Hz), 4.87 (2H, d, J=5.2 Hz), 2.48 (3H, s), 1.93 (1H, t, J=5.5 Hz). $^{13}C$ NMR (CDCl$_3$, 150 MHz): δ ppm 162.73, 160.16 (d, $^1J_{FC}$=255 Hz), 151.11, 139.20 (d, $^4J_{FC}$=8.2 Hz), 133.37, 127.98 (m), 122.53 (q, $^1J_{FC}$=271 Hz), 121.83 (d, $^3J_{FC}$=3.3 Hz), 119.17 (dq, $^2J_{FC}$=33 Hz, $^2J_{FC}$=12 Hz), 114.48 (d, $^2J_{FC}$=23 Hz), 57.05, 15.27. $^{19}F$ NMR (CDCl$_3$, 376 MHz): δ ppm −61.81 (3F, s), −113.84 (1F, s). Anal. Calcd for $C_{12}H_9F_4NOS$: C, 49.49; H, 3.11; N, 4.81. Found: C, 49.52; H, 3.09; N, 4.79.

5-Chloromethyl-4-methyl-2-[3-fluoro-4-(trifluoromethyl)phenyl]thiazole (4d)

In analogy to the procedure described in example 4a, alcohol 3d (1.502 g, 5.157 mmol) was treated with methanesulfonyl chloride and triethylamine in dry DCM to give 4d as a yellow oil (1.357 g, 4.382 mmol, 85.0%). TLC $R_f$ (25% EtOAc/Hexane)=0.68. $^1$H NMR (CDCl$_3$, 600 MHz): δ ppm 7.75 (2H, m), 7.65 (1H, m), 4.79 (2H, s), 2.50 (3H, s). $^{13}$C NMR (CDCl$_3$, 150 MHz): δ ppm 163.38, 161.02 (d, $^1J_{FC}$=255 Hz), 159.32, 153.52, 139.00 (d, $^4J_{FC}$=8.2 Hz), 129.83, 128.02 (q, $^3J_{FC}$=4 Hz), 123.39 (q, $^1J_{FC}$=270 Hz), 121.91 (m), 119.47 (dq, $^2J_{FC}$=33 Hz, $^2J_{FC}$=12 Hz), 114.60 (d, $^2J_{FC}$=22 Hz), 37.15, 15.21. $^{19}$F NMR (CDCl$_3$, 376 MHz): δ ppm −61.82 (3F, s), −113.62 (1F, s). Anal. Calcd for C$_{12}$H$_8$ClF$_4$NS: C, 46.54; H, 2.60; N, 4.52. Found: C, 46.61; H, 2.37; N, 4.44.

Methyl 4-[Oxo-[5-methylene-4-methyl-2-[3-fluoro-4-(trifluoromethyl)phenyl]-thiazole]]cinnamate (5d)

In analogy to the procedure described in example 5a, chloromethyl 4d (0.494 g, 1.595 mmol) and Methyl 4-Hydroxycinnamate were treated with cesium carbonate in anhydrous acetonitrile to give 5d as a white solid (0.614 g, 1.360 mmol, 85.3%). TLC $R_f$ (25% EtOAc/Hexane)=0.46. Mp 180° C. $^1$H NMR (CDCl$_3$, 600 MHz): δ ppm 7.79 (1H, d, J=11 Hz), 7.76 (1H, d, J=8 Hz), 7.67 (1H, d, J=16.0 Hz), 7.66 (1H, m), 7.51 (2H, d, J=8.7 Hz), 6.99 (2H, d, J=8.7 Hz), 6.35 (1H, d, J=16.0 Hz), 5.23 (2H, s), 3.80 (3H, s), 2.52 (3H, s). $^{13}$C NMR (CDCl$_3$, 150 MHz): δ ppm 167.77, 163.51, 161.00 (d, $^1J_{FC}$=254 Hz), 159.71, 152.65, 144.25, 139.14 (d, $^4J_{FC}$=8.4 Hz), 129.89, 128.41, 128.26, 127.98 (q, $^3J_{FC}$=3.9 Hz), 123.40 (q, $^1J_{FC}$=270 Hz), 121.89 (d, $^3J_{FC}$=3 Hz), 119.48 (dq, $^2J_{FC}$=33 Hz, $^2J_{FC}$=13 Hz), 116.13, 115.35, 114.64 (d, $^2J_{FC}$=22 Hz), 62.23, 51.81, 15.55. Anal. Calcd for C$_{22}$H$_{17}$F$_4$NO$_3$S: C, 58.53; H, 3.80; N, 3.10. Found: C, 58.56; H, 3.83; N, 3.15.

4-[Oxo-[5-methylene-4-methyl-2-[3-fluoro-4-(trifluromethyl)phenyl]thiazole]]cinnamic Acid (JM-4-57)

In analogy to the procedure described in example BK-3-51, methyl ester 5d (0.562 g, 1.245 mmol) was treated with 3N NaOH in 95% ethanol to give JM-4-57 as a white solid (0.403 g, 0.921 mmol, 74.0%). TLC $R_f$ (50% EtOAc/Hexane)=0.29. Mp 192-194° C. $^1$H NMR (Acetone-d$_6$, 600 MHz): δ ppm 7.97 (2H, t, J=11 Hz), 7.87 (1H, t, J=7.9 Hz), 7.68 (2H, d, J=8.7 Hz), 7.65 (1H, d, J=16.0 Hz), 7.14 (2H, d, J=8.7 Hz), 6.43 (1H, d, J=16.0 Hz), 5.46 (2H, s), 2.53 (3H, s). $^{13}$C NMR (Acetone-d$_6$, 150 MHz): δ ppm 167.89, 163.30, 161.58 (d, $^1J_{FC}$=254 Hz), 160.79, 153.41, 144.98, 140.57 (d, $^4J_{FC}$=8.4 Hz), 130.77, 130.46, 129.14 (q, $^3J_{FC}$=3.9 Hz), 128.91, 124.51 (q, $^1J_{FC}$=270 Hz), 123.06 (d, $^3J_{FC}$=4 Hz), 119.11 (dq, $^2J_{FC}$=33 Hz, $^2J_{FC}$=13 Hz), 117.10, 116.24, 114.89 (d, $^2J_{FC}$=23 Hz), 62.86, 15.43. Anal. Calcd for C$_{21}$H$_{15}$F$_4$NO$_3$S: C, 57.66; H, 3.46; N, 3.20. Found: C, 57.95; H, 3.48; N, 3.20.

2-(4-Bromophenyl)-1,3-dioxolane (6)

4-Bromobenzaldehyde (4.303 g, 23.26 mmol) was dissolved in anhydrous toluene (50 mL) and ethylene glycol (3.80 mL, 69.18 mmol) was added followed by p-toluenesulfonic acid monohydrate (0.303 g, 1.59 mmol). The mixture was heated to a vigorous reflux set at 140° C. in a Dean-Stark apparatus and stirred at that temperature for 2 days. The mixture was allowed to cool and was poured into a 75 mL saturated NaHCO$_3$ solution and extracted with 40 mL toluene. The organic phase was collected and washed with water twice, dried with Na$_2$SO$_4$, and concentrated under reduced pressure. The resulting crude mixture was purified using column chromatography to give 6 as white solid (2.787 g, 12.17 mmol, 52.3%). TLC $R_f$ (25% EtOAc/Hexane)=0.55. Mp 34-35° C. $^1$H NMR (CDCl$_3$, 600 MHz): δ (ppm) 7.52 (2H, d, J=8.4 Hz), 7.36 (2H, d, J=8.4 Hz), 5.78 (1H, s), 4.10 (2H, m), 4.02 (2H, m). $^{13}$C NMR (CDCl$_3$, 150 MHz): δ (ppm) 137.29, 131.63, 128.30, 123.33, 103.19, 65.43. Anal. Calcd for C$_9$H$_9$O$_2$Br: C, 47.19; H, 3.96; N, 0.00. Found: C, 47.00; H, 3.97; N, 0.00.

2-[4-Thio-[5-methylene-4-methyl-2-phenylthiazole]phenyl]-1,3-dioxolane (7a)

Acetal 6 (0.934 g, 4.077 mmol) was dissolved in THF (15 mL) and cooled to −78° C. A t-BuLi solution in THF (1.7 M, 4.8 mL, 8.55 mmol) was added slowly and the reaction was stirred for 2 hours. Sulfur (0.131 g, 4.078 mmol) was suspended in THF (9 mL) and added to the reaction at −78° C. The mixture was stirred at r.t. for 1.5 hours and was then cooled to 00. Thiazole 4a (0.918 g, 4.103 mmol) was dissolved in THF (15 mL) and added to the reaction mixture. The reaction mixture was allowed to warm to r.t. and stirred for an additional 2 hours. The mixture was quenched with aqueous NH$_4$Cl and the organic phase was separated. The aqueous phase was extracted using two portions of EtOAc and the organic phases were combined and washed with water, brine, and dried over Na$_2$SO$_4$. After evaporation of the solvent, a crude product 7a was isolated as a sticky yellow solid. Attempts to purify the product using column chromatography were unsuccessful and the material was moved to the next step (0.941 g, 2.546 mmol, 62.5%). TLC $R_f$(25% EtOAc/Hexane)=0.23.

4-Thio-[5-methylene-4-methyl-2-phenylthiazole]benzaldehyde (8a)

Crude acetal 7a (0.476 g, 1.288 mmol) was dissolved in THF (15 mL) and 3N HCl (5 mL) was added. The reaction mixture was stirred at r.t. for 2 hours and was concentrated under reduced pressure. The residue was neutralized with 1N NaOH and extracted with EtOAc. The organic extract was washed with water, brine, and dried with Na$_2$SO$_4$. After evaporation of the solvent, the product was purified with column chromatography using a gradient of 10-20% EtOAc/Hexane. The purified product 8a was collected as a yellow solid (0.302 g, 0.928 mmol, 72.0%). TLC $R_f$ (25% EtOAc/Hexane)=0.35. Mp 116-117° C. $^1$H NMR (CDCl$_3$, 600 MHz): δ ppm 9.95 (1H, s), 7.86 (2H, m), 7.80 (2H, d, J=8.3 Hz), 7.43 (2H, d, J=8.3 Hz), 7.41 (3H, m), 4.37 (2H, s), 2.43 (3H, s). $^{13}$C NMR (CDCl$_3$, 150 MHz): δ ppm 191.34, 165.94, 151.23, 144.55, 134.30, 133.51, 130.28, 130.17, 129.04, 128.34, 127.31, 126.42, 29.28, 15.34. Anal. Calcd for C$_{18}$H$_{15}$NOS$_2$: C, 66.43; H, 4.65; N, 4.30. Found: C, 66.29; H, 4.53; N, 4.19.

Methyl 4-[Thio-[5-methylene-4-methyl-2-phenylthiazole]]cinnamate (9a)

Aldehyde 8a (0.251 g, 0.771 mmol) and Methyl (triphenylphosphoranylidene)acetate (0.291 g, 0.870 mmol) were dissolved in THF (6 mL) and stirred at 60° C. for 2 days. The reaction mixture was concentrated and the resulting residue was taken up into EtOAc and washed with water, brine, and dried with Na$_2$SO$_4$. After evaporation of the solvent, the product was purified with column chromatography using a gradient of 5-15% EtOAc/Hexane. The product collected from the column was recrystallized using 95% EtOH to give 9a as a light yellow solid (0.244 g, 0.640 mmol, 83.1%). TLC $R_f$ (25% EtOAc/Hexane)=0.36. Mp 102-103° C. $^1$H NMR (CDCl$_3$, 600 MHz): δ ppm 7.87 (2H, m), 7.63 (1H, d, J=16.0 Hz), 7.44 (2H, d, J=8.2 Hz), 7.41 (3H, m), 7.34 (2H, d, J=8.3 Hz), 6.41 (1H, d, J=16.0 Hz), 4.27 (2H, s), 3.80 (3H, s), 2.35 (3H, s). $^{13}$C NMR (CDCl$_3$, 150 MHz): δ ppm 167.47, 143.99, 137.99, 133.19, 130.50, 130.32, 129.10, 128.86, 128.73, 128.47, 127.35, 126.62, 126.53, 118.09, 51.93, 30.43, 15.08. Anal. Calcd for C$_{18}$H$_{15}$NOS$_2$: C, 66.11; H, 5.02; N, 3.67. Found: C, 66.05; H, 4.87; N, 3.56.

4-[Thio-[5-methylene-4-methyl-2-phenylthiazole]] cinnamic Acid (BK-3-95)

Methyl ester 9a (0.200 g, 0.524 mmol) was dissolved in 95% EtOH (15 mL) using heat. The mixture was cooled to r.t. and 3N NaOH was added. The reaction mixture was stirred for 24 hours and was concentrated under reduced pressure. The resulting residue was taken up into EtOAc and washed with acidified water (HCl, pH=3), brine, and dried with Na$_2$SO$_4$. After evaporation of the solvent, the product was purified by column chromatography using a gradient of 25-100% EtOAc/Hexane. The product collected from the column was recrystallized using 95% EtOH to give BK-3-95 as an off-white solid (0.089 g, 0.243 mmol, 46.4%). TLC $R_f$(50% EtOAc/Hexane)=0.33. Mp 192.5-193.5° C. $^1$H NMR (CDCl$_3$, 600 MHz): δ ppm 7.90 (2H, m), 7.65-7.61 (3H, m), 7.45 (5H, m), 6.51 (1H, d, J=16.0 Hz), 4.52 (2H, s), 2.35 (3H, s). $^{13}$C NMR (CDCl$_3$, 150 MHz): δ ppm 167.47, 165.27, 151.85, 144.41, 139.06, 134.47, 133.69, 130.67, 130.46, 129.77, 129.46, 126.67, 119.15, 15.09. Anal. Calcd for C$_{18}$H$_{15}$NOS$_2$ (0.2H$_2$O mol per target): C, 65.37; H, 4.66; N, 3.81. Found: C, 64.64; H, 4.57; N, 3.72.

2-[4-Thio-[5-methylene-4-methyl-2-[4-(trifluoromethyl)phenyl]thiazole]phenyl]-1,3-dioxolane (7b)

Acetal 6 (0.909 g, 3.968 mmol) was dissolved in THF (15 mL) and cooled to −78° C. A t-BuLi solution in THF (1.7 M, 4.7 mL, 7.99 mmol) was added slowly and the reaction was stirred for 2 hours. Sulfur (0.130 g, 4.053 mmol) was suspended in THF (12 mL) and added to the reaction at −78° C. The mixture was stirred at r.t. for 1.5 hours and was then cooled to 0° C. Thiazole 4b (1.150 g, 3.942 mmol) was dissolved in THF (15 mL) and added to the reaction mixture. The reaction mixture was allowed to warm to r.t. and stirred for an additional 2 hours. The mixture was quenched with aqueous NH$_4$Cl and the organic phase was separated. The aqueous phase was extracted using two portions of EtOAc and the organic phases were combined and washed with water, brine, and dried over Na$_2$SO$_4$. After evaporation of the solvent, a crude product was isolated as a sticky yellow solid. The crude product was purified by column chromatography using a 5-20% EtOAc/Hexane gradient to give 7b as a yellow solid (0.658 g, 1.504 mmol, 38.2%). TLC $R_f$ (25% EtOAc/Hexane)=0.33. Mp 57-61° C. $^1$H NMR (CDCl$_3$, 600 MHz): δ ppm 7.98 (2H, d, J=8.1 Hz), 7.66 (2H, d, J=8.1 Hz), 7.42 (2H, d, J=8.2 Hz), 7.38 (2H, d, J=8.4 Hz), 5.78 (1H, s), 4.24 (2H, s), 4.12 (2H, m), 4.04 (2H, m), 2.31 (3H, m). $^{13}$C NMR (CDCl$_3$, 150 MHz): δ ppm 163.49, 151.42, 137.35, 136.74, 135.84, 131.47 (q, $^2J_{FC}$=32 Hz), 131.09, 130.36, 127.39, 126.56, 125.99 (m), 124.04, 103.33, 65.46, 30.98, 15.11. Anal. Calcd for C$_{21}$H$_{18}$NO$_2$S$_2$ (with 0.4H$_2$O mol per target): C, 56.72; H, 4.26; N, 3.15. Found: C, 56.50; H, 4.00; N, 3.32.

4-Thio-[5-methylene-4-methyl-2-[4-(trifluoromethyl)phenyl]thiazole]benzaldehyde (8b)

Acetal 7b (0.589 g, 1.346 mmol) was dissolved in THF (20 mL) and 3N HCl (5 mL) was added. The reaction mixture was stirred at r.t. for 2 hours and was concentrated under reduced pressure. The residue was neutralized with 1N NaOH and extracted with EtOAc. The organic extract was washed with water, brine, and dried with Na$_2$SO$_4$. After evaporation of the solvent, the product was purified with column chromatography using a gradient of 5-20% EtOAc/Hexane. The purified product 8b was collected as a yellow solid (0.297 g, 0.754 mmol, 56.0%). TLC $R_f$(25% EtOAc/Hexane)=0.36. Mp 77-79° C. $^1$H NMR (CDCl$_3$, 600 MHz): δ ppm 9.94 (1H, s), 7.96 (2H, d, J=8.1 Hz), 7.79 (2H, d, J=8.5 Hz), 7.65 (2H, d, J=8.2 Hz), 7.43 (2H, d, J=8.3 Hz), 4.36 (2H, s), 2.43 (3H, s). $^{13}$C NMR (CDCl$_3$, 150 MHz): δ ppm 191.28, 163.85, 151.76, 144.21, 136.58, 134.39, 131.65 (q, $^2J_{FC}$=32 Hz), 130.30, 128.94, 128.37, 126.57, 126.04 (m), 123.99 (q, $^1J_{FC}$=271 Hz), 29.19, 15.32. Anal. Calcd for C$_{18}$H$_{15}$NOS$_2$: C, 58.00; H, 3.59; N, 3.56. Found: C, 57.83; H, 3.67; N, 3.63.

Methyl 4-[Thio-[5-methylene-4-methyl-2-[4-(trifluoromethyl)phenyl]-thiazole]]cinnamate (9b)

Aldehyde 8b (0.248 g, 0.629 mmol) and Methyl (triphenylphosphoranylidene)acetate (0.238 g, 0.712 mmol) were dissolved in THF (6 mL) and stirred at 40° C. for 2 days. The reaction mixture was concentrated and the resulting residue was taken up into EtOAc and washed with water, brine, and dried with Na$_2$SO$_4$. After evaporation of the solvent, the product 9b was purified with column chromatography using a gradient of 5-15% EtOAc/Hexane and collected as a light yellow solid (0.201 g, 0.447 mmol, 71.1%). TLC $R_f$ (25% EtOAc/Hexane)=0.44. Mp 121-122° C. $^1$H NMR (CDCl$_3$, 600 MHz): δ ppm 7.98 (2H, d, J=8.1 Hz), 7.65 (3H, m), 7.45 (2H, d, J=8.2 Hz), 7.35 (2H, d, J=8.3 Hz), 6.42 (1H, d, J=16.0 Hz), 4.28 (2H, s), 3.81 (3H, s), 2.36 (3H, s). $^{13}$C NMR (CDCl$_3$, 150 MHz): δ ppm 167.43, 163.68, 151.50, 143.91, 137.80, 136.62, 133.27, 131.61 (q, $^2J_{FC}$=32.5 Hz), 130.53, 129.90, 128.74, 126.58, 126.03 (m), 124.01 (q, $^1J_{FC}$=270 Hz), 118.16, 51.93, 30.39, 15.19. Anal. Calcd for C$_{18}$H$_{15}$NOS$_2$: C, 58.78; H, 4.04; N, 3.12. Found: C, 58.98; H, 4.05; N, 3.13.

4-Thio-[5-methylene-4-methyl-2-[4-(trifluoromethyl)phenyl]thiazole]cinnamic Acid (BK-4-04)

To a stirred solution of methyl ester 9b (0.178 g, 0.396 mmol) in 95% Ethanol (12 mL) was added dropwise 3N NaOH (1 mL). After 20 hours, the mixture was concentrated and the resulting residue was suspended in ethyl acetate and washed with acidified water (pH=3, HCl). The organic phase was then washed with water and brine, dried with Na$_2$SO$_4$, filtered and concentrated. The residue was purified by column chromatography and recrystallized with 95% Ethanol to give the product BK-4-04 as a light yellow solid (0.119 g, 0.273 mmol, 68.9%). TLC $R_f$(50% EtOAc/Hexane)=0.54. Mp 217° C. $^1$H NMR (Acetone-d6, 600 MHz): δ ppm 8.11 (2H, d. J=8.1 Hz), 7.80 (2H, d, J=8.1 Hz), 7.64 (3H, m), 7.47 (2H, d, J=8.5 Hz), 6.52 (1H, d, J=16.1 Hz), 4.55 (2H, s), 2.39 (3H, s). $^{13}$C NMR (Acetone-d6, 150 MHz): δ ppm 172.99, 167.62, 163.35, 152.54, 144.54, 128.94, 137.98, 133.89, 131.69 (q, $^2J_{FC}$=32 Hz), 130.64, 129.61, 129.45, 127.31, 126.87 (m), 125.13 (q, $^1J_{FC}$=270 Hz), 119.25, 15.21. $^{19}$F NMR (Acetone-d6, 376 MHz): δ ppm −63.67 (s, 3F). Anal.

Calcd. for $C_{21}H_{16}F_3NO_2S_2$: C, 57.92; H, 3.70; N, 3.22. Found: C, 57.80; H, 3.66; N, 3.29.

2-[4-Thio-[5-methylene-4-methyl-2-[3-(trifluoromethyl)phenyl]thiazole]phenyl]-1,3-dioxolane (7c)

Acetal 6 (1.079 g, 4.710 mmol) was dissolved in THF (15 mL) and cooled to −78° C. A t-BuLi solution in THF (1.7 M, 5.6 mL, 9.52 mmol) was added slowly and the reaction was stirred for 2 hours. Sulfur (0.176 g, 5.488 mmol) was suspended in THF (10 mL) and added to the reaction at −78° C. The mixture was stirred at r.t. for 1.5 hours and was then cooled to 0° C. Thiazole 4c (1.3.90 g, 4.765 mmol) was dissolved in THF (17 mL) and added to the reaction mixture. The reaction mixture was allowed to warm to r.t. and stirred for an additional 2 hours. The mixture was quenched with aqueous $NH_4Cl$ and the organic phase was separated. The aqueous phase was extracted using two portions of EtOAc and the organic phases were combined and washed with water, brine, and dried over $Na_2SO_4$. After evaporation of the solvent, a crude product 7c was isolated as an orange oil. Attempts to purify the product using column chromatography were unsuccessful and the material was moved to the next step (0.604 g, 1.381 mmol, 29.3%). TLC $R_f$ (25% EtOAc/Hexane)=0.31.

4-Thio-[5-methylene-4-methyl-2-[3-(trifluromethyl)phenyl]thiazole]benzaldehyde (8c)

Crude acetal 7c (0.604 g, 1.381 mmol) was dissolved in THF (20 mL) and 3N HCl (5 mL) was added. The reaction mixture was stirred at r.t. for 2.5 hours and was concentrated under reduced pressure. The residue was neutralized with 1N NaOH and extracted with EtOAc. The organic extract was washed with water, brine, and dried with $Na_2SO_4$. After evaporation of the solvent, the product was purified with column chromatography using a gradient of 10-20% EtOAc/Hexane. The purified product 8c was collected as a yellow solid (0.275 g, 0.698 mmol, 50.6%). Elemental analysis was completed after NMR experiments leading to $CDCl_3$ contaminant. TLC $R_f$ (25% EtOAc/Hexane)=0.40. Mp 89-91° C. $^1H$ NMR ($CDCl_3$, 600 MHz): δ ppm 9.95 (1H, s), 8.15 (1H, s), 8.02 (1H, d, J=7.8 Hz), 7.81 (2H, d, J=8.5 Hz), 7.65 (1H, d, J=7.8 Hz), 7.54 (1H, d, J=7.8 Hz), 7.44 (2H, d, J=8.3 Hz), 4.37 (2H, s), 2.44 (3H, s). $^{13}C$ NMR ($CDCl_3$, 150 MHz): δ ppm 191.32, 163.96, 151.64, 144.24, 134.40, 134.27, 131.60 (q, $^2J_{FC}$=33 Hz), 130.33, 129.60, 129.54, 128.65, 128.39, 126.54 (m), 123.90 (q, $^1J_{FC}$=271 Hz), 123.13, 29.22, 15.34. Anal. Calcd for $C_{19}H_{14}F_3NOS_2$ (with 1.0$H_2O$ and 0.1 $CDCl_3$ mol per target): C, 58.00; H, 3.59; N, 3.56. Found: C, 54.11; H, 3.57; N, 3.41.

Methyl 4-[Thio-[5-methylene-4-methyl-2-[3-(trifluoromethyl)phenyl]-thiazole]]cinnamate (9c)

Aldehyde 8c (0.239 g, 0.607 mmol) and Methyl (triphenylphosphoranylidene)acetate (0.228 g, 0.682 mmol) were dissolved in THF (6 mL) and stirred at 60° C. for 2 days. The reaction mixture was concentrated and the resulting residue was taken up into EtOAc and washed with water, brine, and dried with $Na_2SO_4$. After evaporation of the solvent, the product was purified with column chromatography using 10% EtOAc/Hexane and collected 9c as a light yellow solid (0.130 g, 0.289 mmol, 47.6%). TLC $R_f$ (25% EtOAc/Hexane)=0.53. Mp 142-143° C. $^1H$ NMR ($CDCl_3$, 600 MHz): δ ppm 8.14 (1H, s), 8.01 (1H, d, J=7.9 Hz), 7.65 (2H, m), 7.53 (1H, t, J=7.9 Hz), 7.45 (2H, d, J=8.2 Hz), 7.34 (2H, d, J=8.3 Hz), 6.42 (1H, d, J=16.0 Hz), 4.28 (2H, s), 3.81 (3H, s), 2.35 (3H, s). $^{13}C$ NMR ($CDCl_3$, 150 MHz): δ ppm 167.44, 163.72, 151.47, 143.94, 137.87, 134.40, 133.24, 131.58 (q, $^2J_{FC}$=33 Hz), 130.51, 129.56, 129.53, 129.52, 128.74, 126.43 (m), 123.93 (q, $^1J_{FC}$=271 Hz), 123.10 (m), 118.13, 51.92, 30.40, 15.22. Anal. Calcd for $C_{18}H_{15}NOS_2$: C, 58.78; H, 4.04; N, 3.12. Found: C, 58.49; H, 3.90; N, 3.18.

4-Thio-[5-methylene-4-methyl-2-[3-(trifluoromethyl)phenyl]thiazole]cinnamic Acid (BK-4-37)

To a stirred solution of methyl ester 9c (0.120 g, 0.267 mmol) in 95% Ethanol (5 mL) and THF (5 mL) was added dropwise 3N NaOH (1 mL). After 20 hours, the mixture was concentrated and the resulting residue was taken up into EtOAc and washed with acidic water (HCl, pH=3), brine, dried with $Na_2SO_4$, and concentrated. After evaporation of the solvent, the product was purified using column chromatography and recrystallized with 95% Ethanol to give the product BK-4-37 as a light yellow solid (0.082 g, 0.188 mmol, 70.7%). TLC $R_f$ (50% EtOAc/Hexane)=0.51. Mp 150-151° C. $^1H$ NMR (Acetone-d6, 600 MHz): δ ppm 8.21 (1H, s), 8.13 (1H, d, J=7.8 Hz), 7.78 (2H, d, J=7.8 Hz), 7.71 (1H, t, J=7.8 Hz), 7.64 (3H, m), 7.46 (2H, d, J=8.3 Hz), 6.52 (1H, d, J=16.0 Hz), 4.54 (2H, s), 2.38 (3H, s). $^{13}C$ NMR (Acetone-d6, 150 MHz): δ ppm 167.64, 163.37, 152.37, 144.54, 138.95, 135.43, 133.89, 131.69 (q, $^2J_{FC}$=33 Hz), 131.22, 131.08, 130.65, 130.54, 129.60, 127.05 (m), 125.00 (q, $^1J_{FC}$=270 Hz), 122.92 (m), 119.25, 15.18. $^{19}F$ NMR (Acetone-d6, 376 MHz): δ ppm −63.79 (3F, s). Anal. Calcd for $C_{21}H_{16}F_3NO_2S_2$: C, 57.92; H, 3.70; N, 3.22. Found: C, 57.81; H, 3.72; N, 3.23.

2-[4-Thio-[5-methylene-4-methyl-2-[3-fluoro-4-(trifluoromethyl)phenyl]thiazole]phenyl-1,3-dioxolane (7d)

Acetal 6 (0.915 g, 3.99 mmol) was dissolved in THF (15 mL) and cooled to −78° C. A t-BuLi solution in THF (1.7 M, 4.7 mL) was added slowly and the reaction was stirred for 2 hours. Sulfur (0.129 g, 4.022 mmol) was suspended in THF (12 mL) and added to the reaction at −78° C. The mixture was stirred at r.t. then cooled to 0° C. and thiazole 4d (0.9589 g, 3.29 mmol) was added in THF (15 mL). After 20 minutes the reaction was allowed to warm to r.t. and was stirred for an additional 1 hour. The mixture was quenched with $NH_4Cl$ and the organic phase was separated. The aqueous phase was then extracted using two portions of EtOAc. The combined extract was washed with water and brine then dried over $Na_2SO_4$. After evaporation of the solvent, the product was purified with column chromatography using a 0-20% EtOAc/Hexane gradient to give the product 7d as an off-white solid (0.3539 g, 0.776 mmol, 19%). TLC $R_f$ (25% EtOAc/Hexane)=0.40. Mp 105-107° C. $^1H$ NMR ($CDCl_3$, 600 MHz): δ ppm 7.73 (1H, m), 7.70 (1H, m), 7.62 (1H, t, J=7.5), 7.40 (2H, m), 7.37 (2H, m), 5.77 (1H, s), 4.22 (2H, s), 4.10 (2H, m), 4.04 (2H, m), 2.30 (3H, s). $^1C$ NMR ($CDCl_3$, 150 MHz): δ ppm 161.79, 160.85 (d, $^1J_{FC}$=255 Hz), 151.54, 139.07 (d, $^4J_{FC}$=8.2 Hz), 137.34, 135.53, 131.05, 127.77 (d, $^3J_{FC}$=3.9 Hz), 127.32, 122.42 (q, $^1J_{FC}$=270 Hz), 121.61 (d, $^3J_{FC}$=3.3 Hz), 118.90 (dq, $^2J_{FC}$=33 Hz, $^2J_{FC}$=12 Hz), 114.27, (d, $^1J_{FC}$=23 Hz), 103.20, 65.36, 30.83, 14.99. Anal. Calcd for $C_{21}H_{17}F_4NO_2S_2$: C, 55.38; H, 3.76; N, 3.08. Found: C, 55.41; H, 3.65; N, 3.20.

4-Thio-[5-methylene-4-methyl-2-[3-fluoro-4-(trifluromethyl)phenyl]thiazole]benzaldehyde (8d)

Acetal 7d (0.354 g, 0.7770 mmol) was dissolved in THF (12 mL) and 3N HCl (3 mL) was added. The mixture was stirred for 3 hours at room temperature. Sample was concentrated under reduced pressure and neutralized with 1N NaOH. The mixture was then taken into EtOAc, washed with water, brine, and dried with $Na_2SO_4$. After evaporation of the solvent, the crude product was purified with column chromatography using a 5-20% EtOAc/Hexane gradient to give the desired product 8d as an off-white solid (0.2443 g, 0.593 mmol, 76%). TLC $R_f$(25% EtOAc/Hexane)=0.33. Mp 122-123° C. $^1$H NMR (CDCl$_3$, 600 MHz): δ ppm 9.91 (1H, s), 7.76 (2H, d, J=8.4 Hz), 7.69 (1H, d, J=11.2 Hz), 7.65 (1H, d, J=8.3 Hz), 7.59 (1H, t, J=7.6 Hz), 7.39 (2H, d, J=8.4 Hz), 4.32 (2H, s), 2.39 (3H, s), 1.50 (3H, s). $^1$C NMR (CDCl$_3$, 150 MHz): δ ppm 191.15, 162.16, 160.0 (d, $^1J_{FC}$=256 Hz), 151.87, 143.86, 138.88 (d, $^1J_{FC}$=8.3 Hz), 134.37, 130.22, 128.34, 127.82 (d, $^3J_{FC}$=4.2 Hz), 122.36 (q, $^1J_{FC}$=270 Hz), 121.64, 119.11 (dq, $^2J_{FC}$=33 Hz, $^2J_{FC}$=13 Hz), 114.31 (d, $^1J_{FC}$=22 Hz), 29.05, 15.20. Anal. Calcd for $C_{19}H_{13}F_4NOS_2$: C, 55.47; H, 3.18; N, 3.40. Found: C, 55.64; H, 3.35; N, 3.42.

Methyl 4-[Thio-[5-methylene-4-methyl-2-[3-fluoro-4-(trifluoromethyl)phenyl]-thiazole]]cinnamate (9d)

Aldehyde 8d (0.244 g, 0.594 mmol) was dissolved in THF under inert gas and Methyl (triphenylphosphoranylidene)acetate (0.216 g, 0.646 mmol) was added. Reaction was heated to 74° C. and stirred for 2 days. The mixture was concentrated and the resulting residue was taken up into EtOAc and washed with water, brine, and dried with $Na_2SO_4$. After evaporation of the solvent, the crude product was purified with column chromatography using a 5-20% gradient to give the desired product 9d as a white solid (56.1 mg, 0.12 mmol, 20%). TLC $R_f$(25% EtOAc/Hexane)=0.40. Mp 121-123° C. $^1$H NMR (CDCl$_3$, 600 MHz): δ ppm 7.72 (1H, d, J=11.2 Hz), 7.69 (1H, d, J=8.3 Hz), 7.63 (2H, m), 7.44 (2H, d, J=8.4 Hz), 7.33 (2H, d, J=8.3 Hz), 6.40 (1H, d, J=16.0 Hz), 4.27 (2H, s), 3.80 (3H, s), 2.34 (3H, s). $^1$C NMR (CDCl$_3$, 150 MHz): δ ppm 167.28, 161.95, 160.01 (d, $^1J_{FC}$=254 Hz), 151.64, 143.74, 138.95 (d, $^1J_{FC}$=8.3 Hz), 137.48, 133.23, 130.71, 130.46, 128.64, 127.8 (d, $^3J_{FC}$=4.0 Hz), 122.38 (d, $^1J_{FC}$=271 Hz), 121.63, 118.90 (dq, $^2J_{FC}$=33 Hz, $^2J_{FC}$=13 Hz), 118.11, 114.27 (d, $^2J_{FC}$=23 Hz), 51.81, 30.02, 15.05. Anal. Calcd for $C_{22}H_{17}F_4NO_2S_2$: C, 56.62; H, 3.67; N, 3.00. Found: C, 56.54; H, 3.73; N, 3.02.

4-Thio-[5-methylene-4-methyl-2-[3-fluoro-4-(trifluoromethyl)phenyl]thiazole]cinnamic Acid (JF-4-80)

Methyl ester 9d (0.053 g, 0.113 mmol) was dissolved in 95% EtOH (10 mL) with heat. Mixture was allowed to cool to room temperature before 3N NaOH (1 mL) was added. Mixture was stirred overnight and was then concentrated under reduced pressure. Residue was taken into EtOAc and was washed with acidified water (HCl, pH=3), water, brine, and dried with $Na_2SO_4$. Sample recrystallized with 95% ethanol to give JF-4-80 as a white solid (20 mg, 0.0441 mmol, 38%). TLC $R_f$(25% EtOAc/Hexane)=0.20. Mp 180-182° C. $^1$H NMR (CDCl$_3$, 600 MHz): δ ppm 7.88 (2H, m), 7.84 (1H, m), 7.64 (3H, m), 7.47 (2H, m), 6.51 (1H, d, J=15.9 Hz), 4.56 (2H, s), 2.39 (3H, s). $^1$C NMR (CDCl$_3$, 150 MHz): δ ppm 166.69, 160.96, 159.88 (d, $^1J_{FC}$=256 Hz), 151.87, 143.63, 139.71 (d, $^4J_{FC}$=8.8 Hz), 137.89, 133.05, 131.86, 129.78, 128.73, 128.17 (d, $^3J_{FC}$=4.2 Hz), 122.73 (d, $^1J_{FC}$=269 Hz), 121.99, 118.37, 117.95 (dq, $^2J_{FC}$=33 Hz, $^2J_{FC}$=12 Hz), 113.69 (d, $^2J_{FC}$=23 Hz), 14.30. Anal. Calcd for $C_{21}H_{15}F_4NO_2S_2$: C, 55.62; H, 3.33; N, 3.09. Found: C, 55.35; H, 3.44; N, 3.04.

Ethyl 4-(N-tert-butoxycarbonyl)aminocinnamate (10)

Ethyl 4-aminocinnamate (1.270 g, 6.641 mmol) and di-tert-butyl dicarbonate (1.480 g, 6.781 mmol) were dissolved in THF (20 mL) under inert gas and heated to reflux at 65° C. overnight. The mixture was cooled to room temperature and concentrated under reduced pressure. The resulting residue was taken up into EtOAc and washed with sat. NaHCO$_3$, water, brine, dried with $Na_2SO_4$, and concentrated. The crude sample was purified using column chromatography to give the desired product 10 a light orange solid (1.200 g, 4.122 mmol, 62.1%). TLC $R_f$(25% EtOAc/Hexane)=0.46. Mp 93-96° C. $^1$H NMR (CDCl$_3$, 600 MHz): δ ppm 7.63 (1H, d, J=16.0 Hz), 7.47 (2H, d, J=8.6 Hz), 7.39 (2H, d, J=8.5 Hz), 6.59 (1H, s), 6.34 (1H, d, J=16.0 Hz), 4.26 (2H, q, J=7.1 Hz), 1.53 (9H, s), 1.34 (3H, t, J=7.1 Hz). $^{13}$C NMR (CDCl$_3$, 150 MHz): δ (ppm) 167.36, 152.43, 144.17, 140.37, 129.19, 118.39, 116.62, 81.16, 60.51, 28.40, 14.46. Anal. Calcd for $C_{16}H_{21}NO_4$: C, 65.96; H, 7.27; N, 4.81. Found: C, 65.81; H, 7.42; N, 4.93.

Ethyl 4-[N-(tert-Butoxycarbonyl)-N-[(5-methylene-4-methyl-2-phenyl)thiazole]]aminocinnamate (11a)

Ethyl 4-(N-tert-Butoxycarbonyl)aminocinnamate 10 (1.336 g, 4.586 mmol), thiazole 4a (1.027 g, 4.590 mmol), and NaI (0.690 g, 4.603 mmol) were dissolved in anhydrous DMF (30 mL) under inert gas and cooled in an icebath. NaH (60% dispersion in mineral oil, 0.281 g, 7.025 mmol) was carefully added to the reaction mixture by briefly exposing the system to air. The reaction mixture was stirred for 3 hours at room temperature and quenched with a 50% dilution of sat. NaHCO$_3$. The mixture was extracted with three portions of ether which were combined, washed with brine, dried with $Na_2SO_4$, and concentrated. The crude material was purified by column chromatography using a gradient of 100% hexane to 25% EtOAc/hexane to give the desired product 11a as a yellow oil (1.488 g, 3.109 mmol, 67.8%). TLC $R_f$(25% EtOAc/Hexane)=0.39. $^1$H NMR (CDCl$_3$, 600 MHz): δ ppm 7.87 (2H, m), 7.64 (1H, d, J=16.0 Hz), 7.46 (2H, d, J=8.5 Hz), 7.39 (3H, m), 7.15 (2H, bd, J=8.0 Hz), 6.39 (1H, d, J=16.0 Hz), 4.94 (2H, s), 4.25 (2H, q, J=7.1 Hz), 2.19 (3H, s), 1.47 (9H, s), 1.32 (3H, t, J=7.1 Hz). $^1$C NMR (CDCl$_3$, 150 MHz): δ ppm 167.00, 166.24, 154.12, 150.93, 143.69, 143.49, 133.67, 132.70, 130.02, 128.99, 128.71, 128.16, 127.49, 126.41, 118.57, 81.61, 60.65, 45.87, 28.42, 15.13, 14.43. Anal. Calcd for $C_{27}H_{30}N_2O_4S$ (with 0.2H$_2$O mol per target): C, 67.25; H, 6.35; N, 5.81. Found: C, 67.02; H, 6.55; N, 5.58.

Ethyl 4-[N-[5-Methylene-4-methyl-2-phenylthiazole]]aminocinnamate (12a)

BOC protected amine 11a (1.354 g, 2.749 mmol) was dissolved in anhydrous DCM (15 mL) and cooled in an ice bath. Trifluoroacetic acid (3 mL) was added slowly and the mixture was stirred at room temperature for 3 hours. The reaction mixture was then washed with a chilled saturated NaHCO$_3$ solution, water, brine, and dried with $Na_2SO_4$.

After filtration and evaporation of the solvent, the crude product was purified with column chromatography using a gradient of 10% EtOAc/hexane to 25% EtOAc/hexane. The purified product 12a was collected as a yellow solid (0.810 g, 2.140 mmol, 77.8%). TLC $R_f$ (25% EtOAc/Hexane) =0.23. Mp 112-113° C. $^1$H NMR (CDCl$_3$, 600 MHz): δ ppm 7.86 (2H, m), 7.60 (1H, d, J=15.9 Hz), 7.39 (5H, m), 6.63 (2H, d, J=8.6 Hz), 6.23 (1H, d, J=15.8 Hz), 4.47 (2H, s), 4.37 (1H, bs), 4.23 (2H, q, J=7.1 Hz), 2.48 (3H, s), 1.32 (3H, t, J=7.1 Hz). $^{13}$C NMR (CDCl$_3$, 150 MHz): δ ppm 167.83, 165.86, 150.16, 149.10, 144.89, 133.63, 130.02, 129.49, 129.01, 126.38, 124.65, 113.75, 113.00, 60.30, 40.19, 15.44, 14.50. Anal. Calcd for C$_{22}$H$_{22}$N$_2$O$_2$S: C, 69.81; H, 5.86; N, 7.40. Found: C, 69.57; H, 5.88; N, 7.53.

4-[N-[5-Methylene-4-methyl-2-phenylthiazole]]
aminocinnamic Acid (BK-3-91)

Methyl ester 12a (0.721 g, 1.905 mmol) was dissolved in a mixture of THF (20 mL) and 95% ethanol (10 mL). A 3N NaOH solution (3 mL) was added and the reaction mixture was stirred for 24 hours. The reaction was found to be incomplete as determined by TLC and additional 3N NaOH (3 mL) was added. The mixture was stirred for an additional 24 hours (48 hours total) and was neutralized and then acidified with 1N HCl (to pH=3). Organic solvents were removed under reduced pressure and the residue was extracted with EtOAc. The organic extract was washed with brine, dried with Na$_2$SO$_4$, and concentrated. The crude material was purified by column chromatography using a 25% EtOAc/Hexane to 30% EtOAc/Hexane gradient supplemented with dropwise amounts of acetic acid to give the desired product BK-3-91 as a yellow solid (0.308 g, 0.879 mmol, 46.1%). TLC $R_f$ (50% EtOAc/Hexane)=0.15. Mp 205-207° C. $^1$H NMR (Acetone-d6, 600 MHz): δ ppm 10.41 (1H, bs), 7.91 (2H, m), 7.56 (2H, d, J=15.9 Hz), 7.44 (5H, m), 6.76 (2H, d, J=8.6 Hz), 6.23 (1H, d, J=15.9 Hz), 6.16 (1H, bs), 4.61 (2H, s), 2.47 (3H, s). $^{13}$C NMR (Acetone-d6, 150 MHz): δ ppm 168.35, 165.07, 151.06, 150.59, 146.12, 134.77, 132.01, 130.74, 130.58, 129.83, 126.70, 124.32, 113.57, 113.46, 40.11, 15.39. Anal. Calcd for C$_{20}$H$_{18}$N$_2$O$_2$S: C, 68.55; H, 5.18; N, 7.99. Found: C, 68.46; H, 5.20; N, 8.06.

Ethyl 4-[N-(tert-Butoxycarbonyl)-N-[(5-methylene-4-methyl-2-[4-(trifluoromethyl)phenyl]thiazole]]
aminocinnamate (11b)

Ethyl ester 10 (1.342 g, 4.606 mmol), thiazole 4b (1.345 g, 4.611 mmol), and NaI (0.693 g, 4.623 mmol) were dissolved in anhydrous DMF (30 mL) under inert gas and cooled in an icebath. NaH (60% dispersion in mineral oil, 0.288 g, 7.20 mmol) was carefully added to the reaction mixture by briefly exposing the system to air. The reaction mixture was stirred for 3 hours at room temperature and quenched with a 50% dilution of sat. NaHCO$_3$. The mixture was extracted with three portions of ether which were combined, washed with brine, dried with Na$_2$SO$_4$, and concentrated. The crude material was purified by column chromatography using a gradient of 100% hexane to 25% EtOAc/hexane to give the desired product 11b as a yellow solid (1.302 g, 2.384 mmol, 51.8%). TLC $R_f$ (25% EtOAc/Hexane)=0.45. Mp 51-54° C. $^1$H NMR (CDCl$_3$, 600 MHz): δ ppm 7.99 (2H, d, J=8.2 Hz), 7.64 (3H, m), 7.47 (2H, d, J=8.5 Hz), 7.15 (2H, bd, J=8.1 Hz), 6.39 (1H, d, J=16.0 Hz), 4.95 (2H, s), 4.25 (2H, q, J=7.1 Hz), 2.21 (3H, s), 1.47 (9H, s), 1.32 (3H, t, J=7.1 Hz). $^{13}$C NMR (CDCl$_3$, 150 MHz): δ ppm 166.99, 164.25, 154.12, 151.53, 143.62, 143.41, 136.79, 132.80, 131.47 (q, $^2J_{FC}$=32 Hz), 129.59, 128.76, 127.43, 126.59, 126.00 (m), 124.02 (q, $^1J_{FC}$=270 Hz), 118.69, 81.75, 60.70, 45.86, 28.41, 15.15, 14.43. Anal. Calcd for C$_{28}$H$_{29}$F$_3$N$_2$O$_4$S: C, 61.53; H, 5.35; N, 5.13. Found: C, 61.63; H, 5.53; N, 5.27.

Ethyl 4-[N-[5-Methylene-4-methyl-2-[4-(trifluoromethyl)phenyl]thiazole]]aminocinnamate (12b)

BOC protected amine 11b (1.140 g, 2.085 mmol) was dissolved in anhydrous DCM (15 mL) and cooled in an ice bath. Trifluoroacetic acid (3 mL) was added slowly and the mixture was stirred at room temperature for 2 hours. The reaction mixture was then washed with a chilled saturated NaHCO$_3$ solution, water, brine, and dried with Na$_2$SO$_4$. After filtration and evaporation of the solvent, the crude product was purified with column chromatography using a gradient of 10% EtOAc/hexane to 25% EtOAc/hexane. The purified product 12b was collected as an ivory solid (0.793 g, 1.776 mmol, 85.2%). TLC $R_f$ (25% EtOAc/Hexane)=0.20. Mp 120-122° C. $^1$H NMR (CDCl$_3$, 600 MHz): δ ppm 7.98 (2H, d, J=8.1 Hz), 7.65 (2H, d, J=8.2 Hz), 7.60 (1H, d, J=15.9 Hz), 7.39 (2H, d, J=8.6 Hz), 6.65 (2H, d, J=8.6 Hz), 6.24 (1H, d, J=15.9 Hz), 4.52 (2H, s), 4.24 (2H, q, J=7.1 Hz), 2.51 (3H, s), 1.32 (3H, t, J=7.1 Hz). $^{13}$C NMR (CDCl$_3$, 150 MHz): δ ppm 167.79, 163.90, 150.59, 148.79, 144.77, 136.67, 131.61 (q, $^2J_{FC}$=32.5 Hz), 131.22, 130.05, 126.60, 126.05 (m), 125.05, 124.02 (q, $^1J_{FC}$=270 Hz), 114.08, 113.18, 60.36, 40.37, 15.47, 14.53. Anal. Calcd for C$_{23}$H$_{21}$F$_3$N$_2$O$_2$S: C, 61.87; H, 4.74; N, 6.27. Found: C, 61.73; H, 4.77; N, 6.37.

4-[N-[5-Methylene-4-methyl-2-[4-(trifluoromethyl)phenyl]thiazole]]aminocinnamic Acid (BK-4-03)

Methyl ester 12b (0.595 g, 1.333 mmol) was dissolved in a mixture of THF (10 mL) and 95% ethanol (10 mL). A 3N NaOH solution (2 mL) was added and the reaction mixture was stirred for 24 hours. After reaction was determined complete by TLC, 1N HCl was added to pH=3. Organic solvents were removed under reduced pressure and the residue was extracted with EtOAc. The organic extract was washed with brine, dried with Na$_2$SO$_4$, and concentrated. The crude material was purified by column chromatography using a 25% EtOAc/Hexane to 30% EtOAc/Hexane gradient supplemented with dropwise amounts of acetic acid to give the desired product BK-4-03 as a yellow solid (0.153 g, 0.365 mmol, 27.4%). TLC $R_f$ (50% EtOAc/Hexane)=0.35. Mp 224-226° C. $^1$H NMR (Acetone-d6, 600 MHz): δ ppm 10.42 (1H, bs), 8.12 (2H, d, J=8.2 Hz), 7.79 (2H, d, J=8.3 Hz), 7.56 (1H, d, J=15.8), 7.48 (2H, d, J=8.6 Hz), 6.77 (2H, d, J=8.7 Hz), 6.24 (2H, m), 4.65 (2H, s), 2.50 (3H, s). $^{13}$C NMR (Acetone-d6, 150 MHz): δ ppm 168.35, 163.07, 151.11, 150.95, 146.07, 138.17, 134.09, 131.35 (q, $^2J_{FC}$=31.8 Hz), 130.76, 127.22, 126.85 (m), 125.15 (q, $^1J_{FC}$=270 Hz), 124.46, 113.61, 113.58, 40.17, 15.40. $^{19}$F NMR (Acetone-d6, 376 MHz): δ ppm −63.64 (s, 3F). Anal. Calcd for C$_{21}$H$_{17}$F$_3$N$_2$O$_2$S (with 0.4 mol H$_2$O per target): C, 59.26; H, 4.22; N, 6.58. Found: C, 59.41; H, 4.58; N, 6.36.

Ethyl 4-(N-tert-Butoxycarbonyl)-[N-[5-methylene-4-methyl-2-[3-(trifluoromethyl)phenyl]thiazole]]
aminocinnamate (11c)

Ethyl ester 10 (1.313 g, 4.507 mmol), thiazole 4c (1.315 g, 4.509 mmol) and NaI (0.680 g, 4.538 mmol) were dissolved in anhydrous DMF (34 mL) and cooled to 0° C. in an ice bath. The mixture was briefly exposed to air and NaH (60% dispersion in mineral oil, 0.277 g, 6.925 mmol) was added. The reaction mixture was warmed to room temperature and stirred for 2 hours. The solution was quenched with water and diluted with a 1:1 mixture of aqueous NaHCO$_3$ and ether. The two phase mixture was separated and the isolated aqueous phase was extracted twice with ether. The organic phase extracts were combined, washed with brine, dried over Na$_2$SO$_4$, filtered, and concentrated. The crude sample was purified with silica gel column chromatography using a 100% hexane to 15% EtOAc/hexane gradient to give 11c as a viscous yellow oil (1.621 g, 2.966 mmol, 65.8%). TLC R$_f$ (25% EtOAc/hexane)=0.35. $^1$H NMR (CDCl$_3$, 600 MHz): δ ppm 8.18 (1H, s), 8.05 (1H, d, J=7.8 Hz), 7.65 (2H, m), 7.55 (1H, t, J=7.8 Hz), 7.49 (2H, d, J=8.5 Hz), 7.17 (2H, d, J=8.1 Hz), 6.41 (1H, d, J=16.0 Hz), 4.98 (2H, s), 4.28 (2H, q, J=7.1 Hz), 2.23 (3H, s), 1.49 (9H, s), 1.35 (3H, t, J=7.1 Hz). $^{13}$C NMR (CDCl$_3$, 150 MHz): δ ppm 167.00, 164.36, 154.15, 151.38, 143.63, 143.41, 134.40, 132.82, 131.56 (q, $^2J_{FC}$=32 Hz), 129.62, 129.56, 128.77, 126.44 (m), 123.93 (q, $^1J_{FC}$=271 Hz), 123.15 (m), 118.70, 81.75, 60.70, 45.85, 28.43, 15.13, 14.45. Anal. Calcd for C$_{28}$H$_{29}$F$_3$N$_2$O$_4$S: C, 61.53; H, 5.35; N, 5.13. Found: C, 61.39; H, 5.48; N, 5.01.

Ethyl 4-[N-[5-Methylene-4-methyl-2-[3-(trifluoromethyl)phenyl]thiazole]]aminocinnamate (12c)

BOC protected amine 11c (1.30 g, 2.378 mmol) was dissolved in anhydrous DCM (15 mL) and was cooled in an ice bath at 0° C. Trifluoroacetic acid (3 mL) was added and the mixture was stirred for 2 hours. The mixture was then washed with cold saturated NaHCO$_3$, brine, dried over Na$_2$SO$_4$, filtered, and concentrated. The crude sample was purified using silica gel column chromatography and a 10% to 25% EtOAc/hexane gradient to give 12c as a light yellow solid (0.811 g, 1.817 mmol, 76.4%). TLC R$_f$ (25% EtOAc/Hexane)=0.23. Mp 133-135° C. $^1$H NMR (CDCl$_3$, 600 MHz): δ ppm 8.14 (1H, s), 8.02 (1H, d, J=7.9 Hz), 7.63 (1H, d, J=7.8 Hz), 7.60 (1H, d, J=15.9 Hz), 7.52 (1H, m), 7.39 (2H, d, J=8.6 Hz), 6.64 (2H, d, J=8.6 Hz), 6.24 (2H, d, J=15.9 Hz), 4.51 (2H, s), 4.23 (2H, q, J=7.1 Hz), 2.51 (3H, s), 1.32 (3H, t, J=7.1 Hz). $^{13}$C NMR (CDCl$_3$, 150 MHz): δ ppm 167.80, 163.89, 150.44, 148.92, 134.40, 131.57 (q, $^2J_{FC}$=32 Hz), 130.94, 130.05, 129.57, 129.52, 126.42 (m), 124.90, 123.92 (q, $^1J_{FC}$=271 Hz), 123.10 (m), 113.97, 113.08, 60.33, 40.29, 15.46, 14.51. Anal. Calcd for C$_{23}$H$_{22}$F$_3$N$_2$O$_2$S: C, 61.87; H, 4.74; N, 6.27. Found: C, 61.87; H, 4.79; N, 6.26.

4-[N-[5-methylene-4-methyl-2-[3-fluoro-4-(trifluoromethyl)phenyl]thiazole]]aminocinnamic Acid (BK-4-30)

Ethyl ester 12c (0.629 g, 1.409 mmol) was dissolved in 95% ethanol (10 mL) and THF (10 mL). The mixture was cooled in an ice bath at 0° C. and 3N NaOH (2 mL) was added. The mixture was stirred at room temperature overnight and acidified with 1N HCl to a pH near 3. Organic solvents were removed under reduced pressure and the residue was taken up into EtOAc. The mixture was washed with a chilled saturated NaHCO$_3$ solution, brine, dried over Na$_2$SO$_4$, filtered, and concentrated. The crude sample was purified using silica gel column chromatography with a 25% EtOAc/hexane mobile phase that was supplemented with dropwise amounts of glacial acetic acid. A yellow-white solid was collected (0.474 g) and recrystallized using 95% ethanol to give the desired product BK-4-30 as a light yellow solid (0.122 g, 0.292 mmol, 20.7%). TLC R$_f$ (50% EtOAc/Hexane)=0.33. Mp 171-173° C. $^1$H NMR (Acetone-d6, 600 MHz): δ ppm 8.22 (1H, s), 8.13 (1H, d, J=7.9 Hz), 7.77 (1H, d, J=7.8 Hz), 7.70 (1H, t, J=7.8 Hz), 7.56 (1H, d, J=15.8 Hz), 7.47 (2H, d, J=8.6 Hz), 6.76 (2H, d, J=8.7 Hz), 6.24 (2H, d, J=15.8 Hz), 4.64 (2H, s), 2.50 (3H, s). $^{13}$C NMR (Acetone-d6, 150 MHz): δ ppm 168.41, 163.08, 150.95, 150.93, 146.09, 135.61, 133.69, 131.67 (q, $^2J_{FC}$=32 Hz), 131.05, 130.76, 130.47, 126.88 (m), 125.02 (q, $^1J_{FC}$=270 Hz), 124.45, 113.61, 113.58, 40.17, 15.38. $^{19}$F NMR (Acetone-d6, 150 MHz): δ ppm −63.76 (3F, s). Anal. Calcd for C$_{21}$H$_{17}$F$_3$N$_2$O$_2$S: C, 60.28; H, 4.10; N, 6.69. Found: C, 60.16; H, 4.15; N, 6.65.

Ethyl 4-(N-tert-butoxycarbonyl)-[N-[5-methylene-4-methyl-2-[3-fluoro-4-(trifluoromethyl)phenyl]thiazole]]cinnamate (11d)

Ethyl ester 10 (1.274 g, 4.373 mmol) and thiazole 4d (1.314 g, 4.250 mmol) were dissolved in anhydrous DMF (35 mL) and cooled to 0° C. NaI (0.677 g, 4.520 mmol) was added and the mixture was warmed to room temperature and stirred for 1.5 hours. The solution was then quenched with water and extracted with ether/NaHCO$_3$ solution three times. The ether extracts were combined and washed with brine and dried with Na$_2$SO$_4$. The crude yellow-orange oil was concentrated and purified using column chromatography with a 100% hexane to 15% EtOAc/hexane gradient yielding the desired product 11d as a yellow solid (1.075 g, 1.90 mmol, 53%). TLC R$_f$ (25% EtOAc/Hexane)=0.43. Mp 64-66° C. $^1$H NMR (CDCl$_3$, 600 MHz): δ ppm 7.73 (2H, m), 7.64 (2H, m), 7.49 (2H, d, J=8.4 Hz), 7.16 (2H, d, J=8.2 Hz), 6.41 (1H, d, J=15.9 Hz), 4.97 (2H, s), 4.27 (2H, q, J=7.14 Hz), 2.22 (3H, s), 1.47 (9H, s), 1.34 (3H, t, J=7.14 Hz). $^{13}$C NMR (CDCl$_3$, 150 MHz): δ ppm 166.85, 162.60, 159.52 (d, $^1J_{FC}$=254 Hz), 153.99, 151.66, 143.45, 143.22, 139.10 (d, $^1J_{FC}$=8.4 Hz), 132.75, 130.29, 128.67, 127.79, 127.78 (d, $^1J_{FC}$=3.3 Hz), 127.28, 122.42 (q, $^1J_{FC}$=269 Hz) 121.67, 119.00 (dq, $^2J_{FC}$=33 Hz, $^2J_{FC}$=13 Hz) 118.65, 114.32 (d, $^1J_{FC}$=22 Hz), 81.72, 60.60, 28.30, 15.02, 14.33. Anal. Calcd for C$_{28}$H$_{28}$F$_4$N$_2$O$_4$S: C, 59.57; H, 5.00; N, 4.96. Found: C, 59.30; H, 5.13; N, 4.95.

Ethyl 4-[N-[5-Methylene-4-methyl-2-[3-fluoro-4-(trifluoromethyl)phenyl]thiazole]]aminocinnamate (12d)

BOC protected amine 11d (0.684 g, 1.473 mmol) was dissolved is DCM anhydrous (15 mL) and the solution was cooled to 0° C. before trifluoroacetic acid (5 mL) was added. After 1.5 hours, the reaction mixture was concentrated under reduced pressure. The solid yellow crude product was purified using column chromatography with a 100% hexane to 35% EtOAc/hexane gradient yielding the desired product 12d as a yellow solid (0.296 g, 0.637 mmol, 44%). TLC R$_f$ (25% EtOAc/Hexane)=0.20. Mp 138-140° C. $^1$H NMR (CDCl$_3$, 600 MHz): δ ppm 7.77 (1H, d, J=11.2 Hz), 7.72 (1H, d, J=8.3 Hz), 7.63 (2H, m), 7.42 (2H, d, J=8.6 Hz), 6.68 (2H, d, J=8.6 Hz), 6.28 (1H, d, J=15.9 Hz), 4.51 (2H, s), 4.26 (2H, m), 2.52 (3H, s), 1.34 (3H, t, J=7.14 Hz). $^{13}$C NMR (CDCl$_3$, 150 MHz): δ ppm 169.86, 162.15, 160.01 (d, $^1J_{FC}$=255 Hz), 150.74, 148.53, 144.60, 139.8 (d, $^1J_{FC}$=8.3 Hz), 132.02, 129.93, 129.21, 127.80 (d, $^1J_{FC}$=4.2 Hz), 125.02, 122.39 (q, $^1J_{FC}$=270 Hz), 121.62, 118.97 (dq, $^2J_{FC}$=33 Hz, $^2J_{FC}$=13 Hz), 117.96, 114.25 (d, $^1J_{FC}$=22 Hz), 60.25, 40.28, 15.36, 14.39. Anal. Calcd for $C_{23}H_{20}F_4N_2O_2S$: C, 59.48; H, 4.34; N, 6.03. Found: C, 59.48; H, 4.24; N, 6.00.

4-[N-[5-Methylene-4-methyl-2-[3-fluoro-4-(trifluoromethyl)phenyl]thiazole]]aminocinnamic Acid (JF-4-94)

Ethyl ester 12d (97.5 mg, 0.210 mmol) was suspended in 95% EtOH (10 mL) and achieved complete solubility after addition of 3N NaOH (1.0 mL). Reaction mixture was stirred at r.t overnight and was then concentrated. The resulting residue was suspended in EtOAc and washed with acidified water (HCl, pH=3), water, brine, and dried with $Na_2SO_4$. The crude material was purified by column chromatography using a 25% EtOAc/Hexane to 40% EtOAc/Hexane gradient supplemented with dropwise amounts of acetic acid to give the desired product as a yellow solid (90.6 mg). The product was recrystallized using 95% ethanol to give JF-4-94 as a cream-colored crystalline solid (24.0 mg, 0.054 mmol, 26.2%). TLC $R_f$ (50% EtOAc/Hexane)=0.30. Mp 213-214° C. $^1$H NMR (CDCl$_3$, 600 MHz): δ ppm 7.89 (2H, d, J=9.8 Hz), 7.82 (1H, t, J=7.71 Hz), 7.57 (1H, d, J=15.9 Hz), 7.48 (2H, d, J=8.6 Hz), 6.76 (2H, d, J=8.6 Hz), 6.25 (1H, d, J=15.9 Hz), 4.65 (2H, s), 2.50 (3H, s), 1.96 (3H, s). $^1$C NMR (CDCl$_3$, 150 MHz): δ ppm 167.45, 160.68, 158.99, 150.39, 149.94, 145.19, 139.92 (d, $^4J_{FC}$=8.5 Hz), 134.44, 133.13, 129.88, 128.13 (d, $^3J_{FC}$=4.1 Hz), 123.63, 122.8 (q, $^1J_{FC}$=270 Hz), 121.90, 117.8 (dq, $^2J_{FC}$=33 Hz, $^2J_{FC}$=13 Hz), 113.59 (d, $^1J_{FC}$=22 Hz), 112.72, 39.25, 14.50. Anal. Calcd for $C_{21}H_{16}F_4N_2O_2S$: C, 57.79; H, 3.70; N, 6.42. Found: C, 57.74; H, 3.72; N, 6.28.

4-[N-(tert-Butoxycarbonyl)-N-[5-methylene-4-methyl-2-[3-fluoro-4-(trifluoromethyl)phenyl]thiazole]]aminocinnamic Acid. (JF-4-98)

Ethyl ester 11d (206 mg, 0.365 mmol) was dissolved in 95% EtOH (10 mL) and 3N NaOH (1.0 mL) was added. The reaction mixture was stirred at room temperature overnight and was concentrated under reduced pressure. The resulting residue was suspended in EtOAc and washed with acidified water (HCl, pH=3), neutral water, brine and dried with $Na_2SO_4$. Crude product was purified by column chromatography using a 20% EtOAc/hexane to 35% EtOAc/hexane gradient supplemented with dropwise amounts of acetic acid to give the desired product as a white solid. The solid was recrystallized with 95% EtOH giving JF-4-98 as a crystalline white solid product (107.5 mg, 0.2004 mmol, 55%). TLC $R_f$ (50% EtOAc/Hexane)=0.46. Mp 212-214° C. $^1$H NMR (CDCl$_3$, 600 MHz): δ ppm 7.92 (2H, m), 7.84 (1H, t, J=7.8 Hz), 7.68 (2H, d, J=8.4 Hz), 7.64 (1H, d, J=15.9 Hz), 7.33 (2H, d, J=8.4 Hz), 6.50 (1H, d, J=15.9 Hz), 5.12 (2H, s), 2.22 (3H, s), 1.46 (9H, s). $^{13}$C NMR (CDCl$_3$, 150 MHz): δ ppm 166.73, 161.61, 159.83 (d, $^1J_{FC}$=253 Hz), 153.62, 151.81, 143.61, 143.52, 139.79 (d, $^3J_{FC}$=8.6 Hz), 132.53, 131.26, 128.64, 128.17 (d, $^3J_{FC}$=4.1 Hz), 127.39, 122.74 (q, $^1J_{FC}$=270 Hz), 122.08, 118.48, 117.89 (dq, $^2J_{FC}$=33 Hz, $^2J_{FC}$=13 Hz), 113.76 (d, $^1J_{FC}$=23 Hz), 80.78, 45.23, 27.49, 14.26. Anal. Calcd for $C_{26}H_{24}F_4N_2O_4S$: Theory: C, 58.20; H, 4.51; N, 5.22. Found: C, 57.93; H, 4.63; N, 5.08.

Ethyl 4-[N-(tert-butoxycarbonyl)methyl]aminocinnamate (14)

Ethyl 4-N-tert-butoxycarbonyl)aminocinnamate 10 (0.935 g, 3.211 mmol) was dissolved in anhydrous DMF (17 mL) and cooled in an icebath. NaH (60% dispersion in oil, 0.198 g, 4.95 mmol) was added and the mixture was stirred for 60 minutes followed by addition of iodomethane (0.60 mL, 9.63 mmol). The reaction mixture was stirred overnight at room temperature and quenched with a 50% aqueous solution of $NaHCO_3$ and extracted twice with ether. The ether extracts were combined and washed with brine, dried with $Na_2SO_4$, and concentrated. The crude material was purified by column chromatography using a 10% EtOAc/hexane mobile phase giving the product 14 as an off-white solid (0.897 g, 2.937 mmol, 91.5%). TLC $R_f$ (25% EtOAc/Hexane)=0.53. Mp 44-45° C. $^1$H NMR (CDCl$_3$, 600 MHz): δ ppm 7.65 (1H, d, J=16.0 Hz), 7.47 (2H, d, J=8.5 Hz), 7.27 (2H, d, J=8.5 Hz), 6.38 (1H, d, J=16.0 Hz), 4.25 (2H, q, J=7.1 Hz), 3.27 (3H, s), 1.46 (9H, s), 1.33 (3H, t, J=7.1 Hz). $^{13}$C NMR (CDCl$_3$, 150 MHz): δ ppm 167.19, 154.48, 145.60, 143.97, 131.21, 128.40, 125.34, 117.84, 80.97, 60.61, 37.10, 28.42, 14.46. Anal. Calcd for $C_{16}H_{21}NO_4$: C, 66.86; H, 7.59; N, 4.59. Found: C, 66.60; H, 7.52; N, 4.45.

Ethyl 4-(N-Methyl)aminocinnamate (15)

Ethyl 4-[N-(tert-butoxycarbonyl)methyl]aminocinnamate 14 (0.775 g, 2.538 mmol) was dissolved in anhydrous DCM (20 mL) and cooled in an icebath. Trifluoroacetic acid (5 mL) was slowly added and the mixture was allowed to warm to room temperature. The mixture was stirred for 90 minutes and the solvent was removed under reduced pressure. The residue was taken up into EtOAc and washed with chilled saturated $NaHCO_3$, brine, dried with $Na_2SO_4$, filtered, and concentrated. The crude material was purified by column chromatography using 10% EtOAc/Hexane to give the product 15 as a yellow solid (0.474 g, 2.307 mmol, 90.9%). TLC $R_f$ (25% EtOAc/Hexane)=0.37. Mp 49-50° C. $^1$H NMR (CDCl$_3$, 600 MHz): δ ppm 7.61 (1H, d, J=15.8 Hz), 7.37 (2H, d, J=8.5 Hz), 6.56 (2H, d, J=8.6 Hz), 6.21 (1H, d, J=15.8 Hz), 4.23 (2H, q, J=7.1 Hz), 4.08 (1H, bs), 2.87 (3H, s), 1.32 (3H, t, J=7.1 Hz). $^{13}$C NMR (CDCl$_3$, 150 MHz): δ ppm 168.00, 151.17, 145.26, 130.01, 123.47, 112.86, 112.20, 60.21, 30.41, 14.53. Anal. Calcd for $C_{12}H_{15}NO_2$: C, 70.22; H, 7.37; N, 6.82. Found: C, 70.03; H, 7.25; N, 6.71.

Ethyl 4-[N-Methyl-N-[5-methylene-4-methyl-2-phenylthiazole]]aminocinnamate (16a)

Ethyl 4-(N-Methyl)aminocinnamate 15 (0.200 g, 0.974 mmol), thiazole 4a (0.238 g, 1.063 mmol), and NaI (0.180 g, 1.200 mmol) were dissolved in anhydrous DMF (15 mL) and cooled in an icebath. NaH (60% dispersion in oil, 0.080 g, 2.000 mmol) was added and the reaction mixture was stirred at room temperature for 3.5 hours. The reaction mixture was diluted with ether and washed with a 10% aqueous $NaHCO_3$ solution. The organic phase was collected and the aqueous phase was extracted with ether 3 times. The combined organic extracts were washed with brine, dried with $Na_2SO_4$, filtered, and concentrated. Purification by silica gel plug was unsuccessful and the yellow oil crude product 16a (0.346 g, 0.881 mmol, 90.5%) was moved to the next step. TLC $R_f$ (25% EtOAc/Hexane)=0.35.

4-[N-Methyl-N-[5-methylene-4-methyl-2-phenylthiazole]]aminocinnamic Acid (BK-4-43)

Ethyl ester 16a (0.205 g, 0.522 mmol) was dissolved in 95% ethanol (5 mL) and THF (5 mL). The solution was cooled in an ice bath and 3N NaOH (1 mL) was added and the mixture was stirred at room temperature overnight. The reaction mixture was concentrated and the residue was taken up into EtOAc and acidified water (HCl, pH=3). The organic phase was collected and washed with brine, dried with Na$_2$SO$_4$, filtered, and concentrated. The crude product was purified by column chromatography using a 25% EtOAc/Hexane mobile phase spiked with dropwise amounts of acetic acid. The collected product was recrystallized using a mixture of 95% ethanol and EtOAc to give the product BK-4-43 as a light yellow solid (0.061 g, 0.167 mmol, 32.0%). TLC R$_f$ (50% EtOAc/Hexane)=0.36. Mp 196-197° C. $^1$H NMR (CDCl$_3$, 600 MHz): δ ppm 7.88 (2H, m), 7.58 (1H, d, J=15.8 Hz), 7.54 (2H, d, J=8.8 Hz), 7.42 (3H, m), 6.90 (2H, d, J=8.9 Hz), 6.27 (1H, d, J=15.9 Hz), 4.85 (2H, s), 3.10 (3H, s), 2.48 (3H, s). $^{13}$C NMR (CDCl$_3$, 150 MHz): δ ppm 168.38, 165.16, 151.48, 150.94, 145.88, 134.74, 130.74, 130.70, 129.90, 126.81, 124.24, 114.07, 113.71, 49.09, 38.46, 15.57. Anal. Calcd for C$_{21}$H$_{20}$N$_2$O$_2$S: C, 69.12; H, 5.53; N, 7.69. Found: C, 69.03; H, 5.69; N, 7.76.

Ethyl 4-[N-Methyl-N-[5-methylene-4-methyl-2-[4-(trifluoromethyl)phenyl]thiazole]]aminocinnamate (16b)

Ethyl 4-(N-Methyl)aminocinnamate 15 (0.430 g, 2.094 mmol), thiazole 4b (0.661 g, 2.265 mmol), and NaI (0.336 g, 2.241 mmol) were dissolved in anhydrous DMF (15 mL) and cooled in an icebath. NaH (60% dispersion in oil, 0.132 g, 3.300 mmol) was added and the reaction mixture was stirred at room temperature for 2 hours. The reaction mixture was quenched with water, diluted with ether, and washed with a 10% aqueous NaHCO$_3$ solution. The organic phase was collected and the aqueous phase was extracted with ether three times. The combined organic extracts were washed with brine, dried with Na$_2$SO$_4$, filtered, and concentrated. Separation of the starting material and desired product by silica gel column chromatography was unsuccessful and the yellow-orange oil 16b (0.721 g, 1.565 mmol, 74.7%) was moved to the next step. TLC R$_f$ (25% EtOAc/Hexane)=0.36.

4-[N-Methyl-N-[5-methylene-4-methyl-2-[4-(trifluoromethyl)phenyl]thiazole]]aminocinnamic Acid (BK-4-15)

Ethyl ester 16b (0.555 g, 1.205 mmol) was dissolved in 95% ethanol (5 mL) and THF (5 mL). The solution was cooled in an ice bath and 3N NaOH (1 mL) was added and the mixture was stirred at room temperature overnight. The reaction mixture was concentrated and the residue was taken up into EtOAc and acidified water (HCl, pH=3). The organic phase was collected and washed with brine, dried with Na$_2$SO$_4$, filtered, and concentrated. The crude product was purified by column chromatography using a 25% EtOAc/Hexane mobile phase spiked with dropwise amounts of acetic acid. The collected product was recrystallized using EtOAc to give the product BK-4-15 as a yellow solid (0.338 g, 0.782 mmol, 64.9%). TLC R$_f$ (50% EtOAc/Hexane)=0.40. Mp 210-212° C. $^1$H NMR (CDCl$_3$, 600 MHz): δ ppm 8.10 (2H, d, J=8.1 Hz), 7.79 (2H, d, J=8.3 Hz), 7.59 (1H, d, J=15.9 Hz), 7.56 (2H, d, J=8.9 Hz), 6.91 (2H, d, 8.9 Hz), 6.29 (1H, d, J=15.9 Hz), 4.88 (2H, s), 3.12 (3H, s), 2.52 (3H, s). $^{13}$C NMR (CDCl$_3$, 150 MHz): δ ppm 186.31, 163.13, 151.47, 151.33, 145.79, 138.11, 132.60, 131.45 (q, $^2J_{FC}$=32.6 Hz), 130.73, 127.32, 126.90 (m), 124.34, 114.16, 113.70, 49.15, 38.53. Anal. Calcd for C$_{22}$H$_{19}$F$_3$N$_2$O$_2$S: C, 61.10; H, 4.43; N, 6.48. Found: C, 61.11; H, 4.41; N, 6.49.

Ethyl 4-[N-Methyl-N-[5-methylene-4-methyl-2-[3-(trifluoromethyl)phenyl]thiazole]]aminocinnamate (16c)

Ethyl 4-(N-Methyl)aminocinnamate 15 (0.247 g, 1.203 mmol), thiazole 4c (0.407 g, 1.395 mmol), and NaI (0.213 g, 1.421 mmol) were dissolved in anhydrous DMF (15 mL) and cooled in an icebath. NaH (60% dispersion in oil, 0.085 g, 2.125 mmol) was added and the reaction mixture was stirred at room temperature for 3.5 hours. The reaction mixture was quenched with water, diluted with ether, and washed with a 10% aqueous NaHCO$_3$ solution. The organic phase was collected and the aqueous phase was extracted with ether/sat. NaHCO$_3$ three times. The combined organic extracts were washed with brine, dried with Na$_2$SO$_4$, filtered, and concentrated. Separation of the starting material and desired product by silica gel column chromatography was unsuccessful and the yellow solid 16c (0.250 g, 0.543 mmol, 45.1%) was moved to the next step. TLC R$_f$ (25% EtOAc/Hexane)=0.45.

4-[N-Methyl-N-[5-methylene-4-methyl-2-[3-(trifluoromethyl)phenyl]thiazole]]aminocinnamic Acid (BK-4-38)

Ethyl ester 16c (0.240 g, 0.521 mmol) was dissolved in 95% ethanol (5 mL) and THF (5 mL). The solution was cooled in an ice bath and 3N NaOH (1 mL) was added and the mixture was stirred at room temperature overnight. The reaction mixture was concentrated and the residue was taken up into EtOAc and acidified water (HCl, pH=3). The organic phase was collected and washed with brine, dried with Na$_2$SO$_4$, filtered, and concentrated. The crude product was purified by column chromatography using a 25% EtOAc/Hexane mobile phase spiked with dropwise amounts of acetic acid. The collected product was recrystallized using EtOH to give the product BK-4-38 as a yellow solid (0.098 g, 0.226 mmol, 43.5%). TLC R$_f$ (50% EtOAc/Hexane)=0.35. Mp 217° C. $^1$H NMR (CDCl$_3$, 600 MHz): δ ppm 8.21 (1H, s), 8.12 (1H, d, J=7.8 Hz), 7.76 (1H, d, J=7.8 Hz), 7.70 (1H, t, J=7.8 Hz), 7.59 (1H, d, J=15.9 Hz), 7.56 (2H, d, J=8.6 Hz), 6.90 (2H, d, J=8.8 Hz), 6.29 (1H, d, J=15.8 Hz), 4.88 (2H, s), 3.12 (3H, s), 2.51 (3H, s). $^{13}$C NMR (CDCl$_3$, 150 MHz): δ ppm 168.33, 163.13, 151.33, 151.29, 145.83, 135.55, 132.24, 131.70 (q, $^2J_{FC}$=32.5 Hz), 131.10, 130.73, 130.56, 126.98 (q, $^3J_{FC}$=3.7 Hz), 126.85 (q, $^1J_{FC}$=270 Hz), 124.30, 122.92 (q, $^3J_{FC}$=3.6 Hz), 114.09, 113.66, 49.12, 38.51, 15.51. Anal. Calcd for C$_{22}$H$_{19}$F$_3$N$_2$O$_2$S: C, 61.10; H, 4.43; N, 6.48. Found: C, 60.92; H, 4.45; N, 6.45.

Ethyl 4-[N-Methyl-N-[5-methylene-4-methyl-2-[3-fluoro-4-(trifluromethyl)phenyl]thiazole]]aminocinnamate (16d)

To a stirred solution of ethyl ester 15 (0.2885 g, 1.405 mmol), thiazole 4d (0.4754 g, 1.535 mmol), and NaI (0.2384 g, 1.590 mmol) in anhydrous DMF (12 ml) was added NaH (0.0697, 2.904 mmol) slowly while at 0° C. The mixture was stirred at room temperature for 3 hours and turned from a yellow to a dark orange color. Then the reaction mixture was quenched with water and extracted with diethyl ether twice. The ether extracts were combined and washed with brine and dried with Na$_2$SO$_4$. The residue was concentrated then purified by column chromatography on silica gel with 5 to 20% gradient of ethyl acetate/hexane to give the desired product 16d as an orange solid (0.192 g, 0.401 mmol, 28.5%). TLC R$_f$ (25% EtOAc/Hexane)=0.43. Mp 142° C. $^1$H NMR (CDCl$_3$, 600 MHz): δ ppm 7.73 (1H, m), 7.67 (1H, m), 7.63 (2H, m), 7.45 (2H, d, J=8.8 Hz), 6.76 (2H, d, J=8.8 Hz), 6.26 (1H, d, J=16 Hz), 4.68 (2H, s), 4.26 (2H, q, J=7.14 Hz), 3.05 (3H, s), 2.50 (3H, s), 1.33 (3H, t, J=7.14 Hz). $^{13}$C NMR (CDCl$_3$, 150 MHz): δ ppm 167.81, 161.97, 160.97 (d, $^1J_{FC}$=254 Hz), 150.57, 150.09, 144.69, 139.29 (d, $^4J_{FC}$=8.6 Hz), 131.88, 129.99, 127.85, 124.07, 123.42 (q, $^1J_{FC}$=270 Hz), 121.70 (d, $^3J_{FC}$=3.5), 119.16 (dq, $^2J_{FC}$=14 Hz, $^2J_{FC}$=33 Hz), 114.40 (d, $^2J_{FC}$=23 Hz), 113.97, 112.85, 60.33, 49.15, 38.42, 15.57, 14.53. Anal. Calcd for C$_{24}$H$_{22}$F$_4$N$_2$O$_2$S (with 0.3 water mol per target): C, 59.57; H, 4.71; N, 5.79. Found: C, 59.19; H, 4.55; N, 5.74.

4-[N-Methyl-N-[5-methylene-4-methyl-2-[3-fluoro-4-(trifluormethyl)phenyl]thiazole]]aminocinnamic Acid (JM-4-68)

To a stirred solution of ethyl ester 16d (0.157 g, 0.328 mmol) in THF (5 ml) and 95% ethanol (5 ml) was added 3 N NaOH (1 ml) slowly. The mixture was stirred at room temperature overnight and concentrated. The residue was taken up in EtOAc then washed with acidified water (HCl, pH=3), brine and dried with Na$_2$SO$_4$. The residue was concentrated then purified by column chromatography on silica gel with a gradient of 25% to 50% EtOAc/Hexanes including drop-wise amount of acetic acid to give the product JM-4-68 as an orange solid (0.045 g, 0.010 mmol, 31%). TLC R$_f$ (50% EtOAc/Hexanes)=0.36. Mp 214° C. $^1$H NMR (Acetone-d$_6$, 600 MHz): δ ppm 7.86 (2H, m), 7.81 (1H, m), 7.60 (1H, d, J=16 Hz), 7.56 (2H, d, J=8.9 Hz), 6.91 (2H, d, J=8.9 Hz), 6.29 (1H, d, J=16 Hz), 4.89 (2H, s), 3.12 (3H, s), 2.52 (3H, s). $^{13}$C NMR (Acetone-d$_6$, 150 MHz): δ ppm 168.30, 161.56, 159.86 (d, $^1J_{FC}$=255 Hz), 151.61, 151.21, 145.74, 140.72 (d, $^4J_{FC}$=9 Hz), 133.73, 130.69, 129.04 (m), 124.52 (q, $^1J_{FC}$=270 Hz), 124.33, 122.87 (d, $^3J_{FC}$=3.3 Hz), 118.85 (dq, $^2J_{FC}$=33 Hz, $^2J_{FC}$=12 Hz), 114.60 (d, $^2J_{FC}$=23 Hz), 114.14, 113.63, 49.16, 38.54, 15.47. Anal. Calcd for C$_{22}$H$_{18}$F$_4$N$_2$O$_2$S: C, 58.66; H, 4.03; N, 6.22. Found: C, 58.43; H, 4.09; N, 6.21.

Ethyl 4-[N-Ethyl-N-(tert-butoxycarbonyl)]aminocinnamate (17a)

To a stirred solution of N-ethyl-cinnamate 10 (1.459 g, 5.01 mmol) in anhydrous DMF (20 mL) under inert gas at 0° C. was added NaH (60% dispersion in mineral oil, 0.317 g, 13.208 mmol). Mixture stirred for 1 hour and iodoethane (1.2 mL, 14.9 mmol) was then added and mixture continued to stir at room temperature overnight. The mixture was then diluted with 50% sodium bicarbonate solution and extracted with ether three times. The ether extracts were combined and washed with brine, dried with Na$_2$SO$_4$, filtered and concentrated. The residue was concentrated then purified by column chromatography on silica gel with a gradient of 10% to 15% ethyl acetate/hexane to give the desired product 17a as a yellow solid (1.253 g, 3.923 mmol, 78.3%). TLC R$_f$ (25% EtOAc/Hexane)=0.56. Mp 58-60° C. $^1$H NMR (CDCl$_3$, 600 MHz): δ ppm 7.67 (1H, d, J=16.0 Hz), 7.49 (2H, d, J=8.4 Hz), 7.23 (2H, d, J=8.4 Hz), 6.40 (1H, d, J=16.0 Hz), 4.28 (2H, q, J=7.1 Hz), 3.71 (2H, q, J=7.0 Hz), 1.44 (9H, s), 1.35 (3H, t, J=7.1 Hz), 1.17 (3H, t, J=7.0 Hz). $^{13}$C NMR (CDCl$_3$, 150 MHz): δ ppm 167.19, 154.30, 144.44, 143.99, 131.82, 128.54, 126.93, 118.04, 80.62, 60.65, 44.93, 28.46, 14.47, 14.10. Anal. Calcd for C$_{18}$H$_{25}$NO$_4$: C, 67.69; H, 7.89; N, 4.39. Found: C, 67.62; H, 7.90; N, 4.42.

Ethyl 4-(N-Ethyl)-aminocinnamate (18a)

To a stirred solution of ethyl ester 17a (1.143 g, 3.579 mmol) in anhydrous DCM (25 mL) under inert gas at 0° C. was slowly added trifluoroacetic acid (6 mL). The mixture was allowed to warm to room temperature and stirred for 2 hours. The reaction mixture was then concentrated and the residue was taken up into EtOAc and washed with cold saturated NaHCO$_3$, brine, dried with NaSO$_4$, and filtered. The filtrated was concentrated and the resulting residue was purified by column chromatography using a 5% to 10% EtOAc/hexane mobile phase to give the desired product 18a as a light yellow solid (0.741 g, 3.380 mmol, 94.4%). TLC R$_f$ (25% EtOAc/hexane)=0.43. Mp 65-67° C. $^1$H NMR (CDCl$_3$, 600 MHz): δ ppm 7.61 (1H, d, J=16.0 Hz), 7.39 (2H, d, J=8.5 Hz), 6.61 (2H, d, J=8.5), 6.22 (1H, d, J=16.0 Hz), 4.25 (2H, q, J=7.1 Hz), 3.22 (2H, q, J=7.2 Hz), 1.33 (3H, t, J=7.1 Hz), 1.28 (3H, t, J=7.2 Hz). $^{13}$C NMR (CDCl$_3$, 150 MHz): δ ppm 167.95, 149.63, 145.12, 130.05, 124.15, 113.24, 113.09, 60.26, 38.70, 14.66, 14.55. Anal. Calcd for C$_{13}$H$_{17}$NO$_2$: C, 71.21; H, 7.81; N, 6.39. Found: C, 71.01; H, 7.75; N, 6.33.

Ethyl 4-[N-Ethyl-N-[5-methylene-4-methyl-2-[4-(trifluormethyl)phenyl]thiazole]]aminocinnamate (19a)

To a stirred solution of ethyl ester 18a (0.226 g, 1.031 mmol), thiazole 4b (0.3032 g, 1.039 mmol), and NaI (0.184 g, 1.228 mmol) in anhydrous DMF (15 mL) and was added NaH (60% dispersion in mineral oil, 0.0612 g, 2.550 mmol) slowly while at 0° C. The mixture then stirred at rt for 3.5 hours. The mixture was quenched with 10% NaHCO$_3$ solution and extracted with diethyl ether three times. The ether extracts were combined and washed with brine and dried with Na$_2$SO$_4$. After filtration, the filtrate was concentrated and purified by column chromatography on silica gel with 5 to 25% gradient of ethyl acetate/hexane. The purification was unsuccessful and gave the product 19a as a crude orange solid (0.158 g, 0.333 mmol, 32.3%). Crude product was moved to the next step without further purification. TLC R$_f$ (25% EtOAc/Hexane)=0.53. $^1$H NMR (CDCl$_3$-d, 600 MHz): δ ppm 7.92 (2H, d, J=8.2 Hz), 7.61 (1H, d, J=16 Hz), 7.59 (2H, d, J=8.2 Hz), 7.40 (2H, d, J=8.9 Hz), 6.69 (2H, d, J=8.9 Hz), 6.23 (1H, d, J=16 Hz), 4.58 (2H, s), 4.23 (2H, q, J=7.14 Hz), 3.49 (2H, q, J=7.08), 2.48 (3H, s), 2.45 (1H, s), 1.30 (3H, t, J=7.14 Hz), 1.22 (3H, t, J=7.08 Hz). $^{13}$C NMR (CDCl$_3$-d, 150 MHz): δ ppm 167.71, 163.21, 152.10, 149.66, 148.89, 144.65, 136.74, 132.07, 131.28 (q, $^2J_{FC}$=32 Hz), 129.95, 129.03, 126.52, 126.32, 125.83 (q, $^3J_{FC}$=3.8 Hz), 124.84 (q, $^1J_{FC}$=270 Hz), 123.04, 113.35, 112.40, 60.12, 46.73, 45.24, 15.41, 14.38, 12.20.

4-[N-Ethyl-N-[5-methylene-4-methyl-2-[4-(trifluormethyl)phenyl]thiazole]]aminocinnamic Acid (JM-1-15)

To a stirred solution of ethyl ester 19a (0.132 g, 0.278 mmol) in THF (4 ml) and 95% ethanol (4 ml) was added 3 N NaOH (1 ml) slowly. The reaction mixture was stirred at room temperature overnight and upon completion was diluted with EtOAc, quenched with acidified water (HCl, pH=3), washed with brine, dried with Na$_2$SO$_4$, and filtered. The filtrate was concentrated then purified by column chromatography with a gradient of 15% to 45% ethyl acetate/hexanes with dropwise amounts of acetic acid to give the desired product JM-1-15 as orange solid (0.061 g, 0.137 mmol, 49%). TLC R$_f$(50% EtOAc/Hexanes)=0.43. Mp 198° C. $^1$H NMR (Acetone-d$_6$, 600 MHz): δ ppm 8.09 (2H, d, J=8.9 Hz), 7.78 (2H, d, J=8.2 Hz), 7.58 (1H, d, J=16 Hz), 7.52 (2H, d, J=8.9 Hz), 6.86 (2H, d, J=8.9 Hz), 6.27 (1H, d, J=16 Hz), 4.82 (2H, s), 3.62 (2H, q, J=7 Hz), 2.51 (3H, s), 1.25 (3H, t, J=7 Hz). $^{13}$C NMR (Acetone-$d_6$, 150 MHz): δ ppm 168.45, 162.97, 150.80, 150.05, 145.83, 138.08, 133.86, 131.43 (q, $^2J_{FC}$=32 Hz), 130.80, 127.21, 126.82 (q, $^3J_{FC}$=4 Hz), 126.03 (q, $^1J_{FC}$=270 Hz), 123.88, 113.76, 113.36, 47.22, 45.92, 15.49, 12.52. Anal. Calcd for $C_{23}H_{21}F_3N_2O_2S$ with 0.17 mol per target $CDCl_3$: C, 59.60; H, 4.53; N, 6.00. Found: C, 59.56; H, 4.75; N, 5.96.

Ethyl 4-[N-Isopropyl-N-(tert-butoxycarbonyl)]aminocinnamate (17b)

Ethyl 4-aminocinnamate-BOC 10 (0.840 g, 2.885 mmol) was dissolved in DMF (20 mL) and NaH (60% dispersion in mineral oil, 0.262 g, 6.550 mmol) was added while reaction vessel was in an ice bath. The solution was stirred for 1 hour and 2-iodopropane (1 mL, 10.1 mmol) was added. The reaction was allowed to warm to room temperature and was stirred overnight. Reaction mixture was quenched with saturated $NaHCO_3$ and extracted with ether three times. The ether extracts were combined and washed with brine, dried with $Na_2SO_4$, and filtered. The crude material was purified by column chromatography with a gradient of 5% to 10% EtOAc/hexane to give the desired product 17b as a yellow oil (0.488 g, 1.46 mmol, 50%). TLC $R_f$ (25% EtOAc/Hexane)=0.58. $^1$H NMR ($CDCl_3$, 600 MHz): δ ppm 7.69 (1H, d, J=15.9 Hz), 7.50 (2H, d, J=8.3 Hz), 7.11 (2H, d, J=8.3 Hz), 6.42 (1H, d, J=16.0 Hz), 4.50 (1H, sep, J=6.8 Hz), 4.27 (2H, q, J=7.14 Hz), 1.38 (9H, s), 1.35 (3H, t, J=7.14 Hz), 1.13 (6H, d, J=6.8 Hz). $^1$C NMR ($CDCl_3$, 150 MHz): δ ppm 166.97, 154.56, 143.86, 141.33, 132.97, 130.26, 128.21, 118.40, 80.02, 60.56, 48.80, 28.35, 21.55, 14.34.

Ethyl 4-(N-Isopropyl)aminocinnamate (18b)

Ethyl ester 17b (1.05 g, 3.149 mmol) was dissolved with anhydrous DCM (25 mL). The solution was placed in an ice bath and cooled to 0° C. before TFA (8 mL) was added. After 1.5 hours, the reaction mixture was concentrated under reduced pressure. The residue was purified by column chromatography to give the desired product 18b as a white solid (0.609 g, 2.613 mmol, 83.0%). TLC $R_f$=0.11 (25% EtOAc/Hexane). Mp 112-115° C. $^1$H NMR ($CDCl_3$, 600 MHz): δ ppm 7.59 (1H, d, J=15.84 Hz), 7.35 (2H, d, J=8.52 Hz), 6.54 (2H, d, J=8.64 Hz), 6.20 (1H, d, J=15.84 Hz), 4.23 (2H, q, J=7.14 Hz), 3.67 (1H, sept., J=6.3 Hz), 1.32 (3H, t, J=7.14 Hz), 1.22 (6H, d, J=6.3 Hz) (2H, m). $^{13}$C NMR ($CDCl_3$, 150 MHz): δ ppm 167.91, 149.19, 145.11, 130.00, 123.15, 112.82, 112.61, 60.08, 44.12, 22.84, 14.43. Anal. Calcd for $C_{14}H_{19}NO_2$: C, 72.07; H, 8.21; N, 6.00. Found: C, 72.03; H, 8.30; N, 5.98.

Ethyl 4-[N-Isopropyl-N-[5-methylene-4-methyl-2-(4-trifluoromethylphenyl)thiazole]]aminocinnamate (19b)

N-isopropyl ester 18b (0.490 g, 2.100 mmol), thiazole 4b (0.745 g, 2.554 mmol) and NaI (0.41 g, 2.735 mmol) were dissolved in dry DMF (25 mL) and cooled to 0° C. NaH (0.107 g, 2.675 mmol) was added and the reaction mixture was stirred for 4 hours at room temperature. The mixture was diluted with a solution of $NaHCO_3$ and extracted with ether three times. The ether extracts were combined and washed with brine, water, dried with $Na_2SO_4$, and filtered. Attempts to purify crude sample by column chromatography failed and the crude product 19b was moved to next step without further purification (0.181 g, 0.370 mmol, 18%). TLC $R_f$ (25% EtOAc/Hexane)=0.35. Mp 80-82° C. $^1$H NMR ($CDCl_3$, 600 MHz): δ ppm 7.93 (2H, d, J=8.19 Hz), 7.61 (2H, d, J=8.19 Hz), 7.57 (1H, s), 7.39 (H, d, J=15.84 Hz), 4.23 (2H, q, J=8.14 Hz), 3.67 (1H, sep, J=6.3 Hz), 1.32 (3H, t, J=7.14 Hz), 1.22 (6H, d, J=6.3 Hz) (2H, m). $^{13}$C NMR ($CDCl_3$, 150 MHz): δ ppm 167.74, 163.15, 149.79, 148.21, 144.57, 136.80, 134.71, 131.15 (q, $^2J_{FC}$=32 Hz), 129.79, 127.45, 126.26, 125.81 (q, $^3J_{FC}$=3.5 Hz), 124.35 (q, $^1J_{FC}$=270 Hz), 113.69, 60.19, 49.02, 41.53, 20.00, 15.59, 14.39. Anal. Calcd for $C_{26}H_{27}N_2O_2S$ with 0.4 per mol target $H_2O$: C, 62.99; H, 5.65; N, 5.65. Found: C, 62.75; H, 5.49; N, 5.58.

4-[N-Isopropyl-N-[5-methylene-4-methyl-2-(4-trifluoromethylphenyl)thiazole]]aminocinnamic Acid (JF-1-13

N-isopropyl ester 19b (0.168 g, 0.344 mmol) was dissolved in EtOH (5 mL) and THF (5 mL) and cooled in ice bath. 3N NaOH (1 mL) was added and the reaction mixture was stirred at room temperature overnight. Reaction mixture was concentrated and the resulting residue was suspended in EtOAc and washed with acidified water (HCl, pH=3), water, brine, dried with $Na_2SO_4$, and filtered. The filtrate was purified by column chromatography with a gradient of 5% to 30% EtOAc/hexane to give the desired product JF-1-13 as a white solid (0.122 g, 0.266 mmol, 77.1%). TLC $R_f$ (50% EtOAc/Hexane)=0.52. Mp 208-210° C. $^1$H NMR ($CDCl_3$, 600 MHz): δ ppm 8.20 (2H, d, J=8.1 Hz), 7.88 (2H, d, J=8.3 Hz), 7.67 (1H, d, J=15.9 Hz), 7.62 (2H, d, J=8.9 Hz), 7.0 (2H, d, J=9.0 Hz), 6.36 (1H, d, J=15.8 Hz), 4.53 (1H, sept., J=6.6 Hz), 2.63 (3H, s), 2.07 (2H, s), 1.43 (6H, d, J=6.6 Hz). $^{13}$C NMR ($CDCl_3$, 150 MHz): δ ppm 167.34, 161.79, 150.14, 148.66, 144.78, 137.34, 135.51, 130.31 (q, $^2J_{FC}$=32 Hz), 129.72, 126.21, 125.91 (q, $^3J_{FC}$=3.5 Hz), 124.27 (q, $^1J_{FC}$=270 Hz), 123.58, 113.68, 49.04, 41.09, 19.57, 19.15, 14.71. Anal. Calcd for $C_{24}H_{23}F_3N_2O_2S$: C, 62.60; H, 5.03; N, 6.08. Found: C, 62.30; H, 5.09; N, 6.03.

Ethyl 4-[N-Propyl-N-(tert-butoxycarbonyl)]aminocinnamate (17c)

To a stirred solution of Ethyl 4-aminocinnamate-BOC 10 (2.147 g, 7.374 mmol) in anhydrous DMF (25 mL) under inert gas at 0° C. was added NaH (60% dispersion in mineral oil, 0.314 g, 7.850 mmol). Mixture stirred for 1 hour and 1-Iodopropane (2.2 mL, 22.558 mmol) was then added and mixture continued to stir at room temperature overnight. The reaction mixture was then diluted with 50% sodium bicarbonate solution and extracted with ether 3 times. The ether extracts were combined and washed with brine, dried with $Na_2SO_4$, filtered and concentrated. The residue was concentrated then purified by column chromatography on silica gel with a gradient of 100% Hexanes to 10% ethyl acetate/hexanes to give the desired product 17c as a yellow solid (2.290 g, 6.868 mmol, 93.2%). TLC $R_f$ (25% EtOAc/Hexane)=0.59. Mp 56° C. $^1$H NMR ($CDCl_3$, 600 MHz): δ ppm 7.66 (1H, d, J=16 Hz), 7.48 (2H, d, J=8.4 Hz), 7.22 (2H, d, J=8.4 Hz), 6.39 (1H, d, J=16 Hz), 4.27 (2H, q, J=7.14 Hz), 3.61 (2H, q, J=7.4 Hz), 1.57 (2H, q, J=7.4 Hz), 1.43 (9H, s), 1.34 (3H, t, J=7.14 Hz), 0.88 (3H, t, J=7.4 Hz). $^{13}$C NMR ($CDCl_3$, 150 MHz): δ ppm 167.12, 154.50, 144.52, 143.94, 131.80, 128.50, 127.03, 118.02, 80.54, 60.60, 51.53, 28.41, 21.91, 14.44, 11.56. Anal. Calcd for $C_{19}H_{27}NO_4$: C, 68.44; H, 8.16; N, 4.20. Found: C, 68.46; H, 8.22; N, 4.22.

Ethyl 4-(N-Propyl)aminocinnamate (18c)

To a stirred solution of ethyl ester 17c (2.080 g, 6.238 mmol) in anhydrous DCM (30 mL) under inert gas at 0° C.

was added trifluoroacetic acid (8 mL) slowly. The mixture was allowed to warm to room temperature and stirred for 2 hours. The mixture was then concentrated and residue was taken up in EtOAc and washed with cold saturated NaHCO$_3$, brine, and dried with sodium sulfate. After filtration, the filtrate was concentrated and purified by column chromatography on silica gel with a gradient of 10% to 20% EtOAc/hexane to give an orange solid 18c (0.573 g, 2.455 mmol, 39.4%). TLC R$_f$(25% EtOAc/Hexane)=0.43. Mp 78° C. $^1$H NMR (CDCl$_3$, 600 MHz): δ ppm 7.61 (1H, d, J=16 Hz), 7.38 (2H, d, J=8 Hz), 6.61 (2H, d, J=8 Hz), 6.23 (1H, d, J=16 Hz), 4.25 (2H, q, J=7.14 Hz), 3.13 (2H, t, J=7.3 Hz), 1.68 (2H, q, J=7.3 Hz), 1.33 (3H, t, J=7.14 Hz), 1.00 (3H, t, J=7.3 Hz). $^{13}$C NMR (CDCl$_3$, 150 MHz): δ ppm 167.97, 149.60, 145.11, 130.06, 129.23, 124.16, 133.22, 60.28, 46.01, 22.50, 14.54, 11.67. Anal. Calcd for C$_{13}$H$_{17}$F$_4$NO$_2$ (with 0.13 mol CDCl$_3$ per target contaminant): C, 68.17; H, 7.69; N, 5.63. Found: C, 68.09; H, 7.50; N, 5.53.

Ethyl 4-[N-Propyl-N-[5-methylene-4-methyl-2-[4-(trifluormethyl)phenyl]aminocinnamate (19c)

To a stirred solution of ethyl ester 18c (0.237 g, 1.014 mmol), thiazole 4b (0.325 g, 1.115 mmol), and NaI (0.231 g, 1.542 mmol) in anhydrous DMF (15 mL) and was added NaH (0.045, 1.896 mmol) slowly while at 0° C. The mixture then stirred at rt for 4 hours. Then the mixture was quenched with 50% NaHCO$_3$ and extracted with ether three times. The ether extracts were combined and washed with brine and dried with Na$_2$SO$_4$. The residue was concentrated then purified by column chromatography on silica gel with 10 to 30% gradient of EtOAc/hexane to give the desired product 19c as an orange solid (0.294 g, 0.603 mmol, 60%). TLC R$_f$ (25% EtOAc/Hexane)=0.35. Mp 128-129° C. $^1$H NMR (CDCl$_3$, 600 MHz): δ ppm 7.97 (2H, d, J=8.2 Hz), 7.64 (2H, d, J=8.2 Hz), 7.61 (1H, d, J=16 Hz), 7.43 (2H, d, J=8.9 Hz), 6.75 (2H, m), 6.25 (1H, d, J=16 Hz), 4.66 (2H, s), 4.25 (2H, q, J=7.14 Hz), 3.40 (2H, t, J=7.4 Hz), 2.50 (3H, s), 1.72 (2H, q, J=7.6 Hz), 1.33 (3H, t, J=7.14 Hz), 0.99 (3H, t, J=7.4 Hz). $^{13}$C NMR (CDCl$_3$, 150 MHz): δ ppm 167.89, 163.61, 149.79, 148.99, 144.73, 136.68, 131.92, 131.60 ($^2J_{FC}$=32 Hz), 130.05, 126.58, 126.01 ($^3J_{FC}$=3.9 Hz), 124.92 ($^1J_{FC}$=270 Hz), 123.69, 113.65, 112.69, 60.32, 53.18, 47.66, 20.62, 15.57, 14.53, 11.56. Anal. Calcd for C$_{26}$H$_{27}$F$_3$N$_2$O$_2$S: C, 63.92; H, 5.57; N, 5.73. Found: C, 63.71; H, 5.55; N, 5.65.

4-[N-Propyl-N-[5-methylene-4-methyl-2-[4-(trifluormethyl)phenyl]]aminocinnamic Acid (JM-1-12)

To a stirred solution of ethyl ester 19c (0.165 g, 0.337 mmol) in THF (5 mL) and 95% ethanol (5 ml) was added 3 N NaOH (1 ml) slowly. The mixture was stirred at room temperature overnight and taken up in EtOAc then quenched with acidified water (HCl, pH=3), washed with brine and dried with Na$_2$SO$_4$. The residue was concentrated then purified by column chromatography on silica gel with a gradient of 15% to 50% EtOAc/hexane supplemented with drop-wise amounts of acetic acid to give the desired compound JM-1-12 as orange solid (0.134 g, 0.290 mmol, 86.1%). TLC R$_f$ (50% EtOAc/Hexanes)=0.36. Mp 205° C. $^1$H NMR (Acetone-d$_6$, 600 MHz): δ ppm 8.10 (2H, d, J=8.2 Hz), 7.78 (2H, d, J=8.2 Hz), 7.58 (1H, d, J=16 Hz), 7.52 (2H, d, J=8.9 Hz), 6.85 (2H, d, J=8.9 Hz), 6.26 (1H, d, J=16 Hz), 4.85 (2H, s), 3.51 (2H, q, J=7.5 Hz), 2.51 (3H, s), 1.74 (2H, sex, J=7.5 Hz), 0.99 (3H, t, J=7.5 Hz). $^{13}$C NMR (Acetone-d$_6$, 150 MHz): δ ppm 168.35, 162.94, 150.85, 150.24, 145.83, 138.09, 133.72, 131.43 ($^2J_{FC}$=32 Hz), 130.76, 127.21, 126.83 ($^3J_{FC}$=4 Hz), 126.04 ($^1J_{FC}$=270 Hz), 123.82, 113.70, 113.37, 53.49, 47.80, 21.17, 15.50, 11.49. Anal. Calcd for C$_{24}$H$_{23}$F$_3$N$_2$O$_2$S: C, 62.60; H, 5.03; N, 6.08. Found: C, 62.20; H, 5.04; N, 6.03.

4-Bromo-2-methylbenzaldehyde (21a)

4-Bromo-2-methylbenzonitrile 20a (1.859 g, 9.483 mmol) was dissolved in anhydrous toluene (40 mL) under nitrogen and was cooled to −78° C. Reagent grade DIBAL-H (1.70 mL, 9.538 mmol) was added slowly and mixture was stirred for 30 minutes. Anhydrous methanol (3 mL) was carefully added followed by 2M H$_2$SO$_4$ (9 mL) dropwise. Mixture was stirred overnight at r.t. The mixture was diluted with ethyl acetate (50 mL) and the organic phase was collected, dried with Na$_2$SO$_4$, and concentrated. The crude material was purified with flash chromatography using 5% EtOAc/hexane to give 20a as an off-white solid (1.590 g, 7.988 mmol, 84.2%). TLC R$_f$ (25% EtOAc/Hexane)=0.80. Mp 29-30° C. $^1$H NMR (CDCl$_3$, 600 MHz): δ ppm 10.22 (1H, s), 7.66 (1H, d, J=8.22), 7.51 (1H, dd, J$_1$=8.22, J$_2$=1.92), 7.45 (1H, s), 2.65 (3H, s). $^{13}$C NMR (CDCl$_3$, 150 MHz): δ ppm 191.76, 142.86, 134.86, 133.35, 133.02, 129.83, 129.01, 19.40.

tert-Butyl-N-methylcarbamate

Di-tert-butyl dicarbonate (10.91 g, 49.98 mmol) was dissolved in anhydrous THF (30 mL) under nitrogen and was cooled in ice bath. 2 M Methylamine in THF (50.0 mL, 0.1 mol) was added slowly and mixture was allowed to warm to r.t and was stirred overnight. Solvent was removed using rotary evaporation and the resulting residue was taken up into 1 M HCl and DCM. The organic phase was collected and the aqueous phase was extracted with a separate portion of DCM. The organic phases were combined and washed with water, dried with sodium sulfate, and concentrated. Residual solvents were removed using Kugelrohr distillation to give the title compound as light yellow oil (6.476 g, 49.37 mmol, 98.7%). $^1$H NMR (CDCl$_3$, 600 MHz): δ ppm 4.43 (1H, bs), 2.73 (3H, d, J=4.92 Hz), 1.45 (9H, s). $^{13}$C NMR (CDCl$_3$, 150 MHz): δ ppm 156.74, 79.25, 28.57, 27.26. Anal. Calcd for C$_6$H$_{13}$NO$_2$ (with 0.1 mol H$_2$O and 0.1 mol DCM per target): C, 51.79; H, 9.55; N, 9.90. Found: C, 51.70; H, 9.34; N, 9.73.

2-Methyl-4-[N-(tert-butoxycarbonyl)methyl]benzaldehyde (22a)

Aldehyde 21a (1.286 g, 6.461 mmol), tert-Butyl-N-methylcarbamate (1.015 g, 7.737 mmol), and Cs$_2$CO$_3$ (2.958 g, 9.078 mmol) were dissolved in anhydrous dioxane (40 mL) and under nitrogen. Xantphos (0.175 g, 0.302 mmol) and Pd$_2$(dba)$_3$ (0.136 g, 0.148 mmol) were measured out in nitrogen bag and added to the reaction flask. The reaction mixture was refluxed with stirring overnight and was then cooled to room temperature before removal of the solvent under reduced pressure. The resulting residue was taken up into EtOAc and water followed by filtration through celite. The EtOAc phase was collected and washed with water, brine, and dried with Na$_2$SO$_4$. After filtration, the filtrate was concentrated and the residue was purified using column chromatography and a 100% hexane to 5% EtOAc/hexane mobile phase gradient to give the desired product 22a as a yellow oil (0.976 g, 3.914 mmol, 60.6%). TLC R$_f$ (25% EtOAc/hexane)=0.53. $^1$H NMR (CDCl$_3$, 600 MHz): δ ppm 10.21 (1H, s), 7.77 (1H, d, J=8.4 Hz), 7.29 (1H, d, J=2.2 Hz), 7.20 (1H, d, J=1.7 Hz), 3.31 (3H, s), 2.67 (3H, s), 1.50 (9H, s). $^{13}$C NMR (CDCl$_3$, 150 MHz): δ ppm 191.65, 154.21, 148.54, 141.42, 132.72, 130.94, 127.38, 122.27, 81.40, 36.91, 28.46, 19.75. Anal. Calcd for C$_{14}$H$_{19}$NO$_3$ (with 0.1H$_2$O and 0.1 mol DCM per target): C, 65.24; H, 7.53; N, 5.40. Found: C, 65.27; H, 7.18; N, 5.06.

Methyl 2-Methyl-4-[N-(tert-butoxycarbonyl)methyl] aminocinnamate (23a)

Aldehyde 22a (0.591 g, 2.371 mmol) and methyl(triphenylphosphoranylidene)acetate (0.876 g, 2.620 mmol) were dissolved in anhydrous THF (10 mL) under nitrogen gas and stirred at 55° C. for 2 days. The reaction mixture was concentrated and the resulting crude solid was taken up into EtOAc and washed with water, brine, and dried with Na$_2$SO$_4$. After filtration, the filtrate was concentrated and purified using column chromatography with a 5% to 15% EtOAc/hexane gradient to give the desired product 23a as a yellow oil (0.548 g, 1.794 mmol, 75.7%). TLC R$_f$ (25% EtOAc/hexane)=0.53. $^1$H NMR (CDCl$_3$, 600 MHz): δ ppm 7.94 (1H, d, J=15.9 Hz), 7.51 (1H, d, J=9.1 Hz), 7.11 (2H, m), 6.34 (1H, d, J=15.9 Hz), 3.81 (3H, s), 3.26 (3H, s), 2.42 (3H, s), 1.47 (9H, s). $^{13}$C NMR (CDCl$_3$, 150 MHz): δ ppm 167.70, 154.56, 145.35, 141.94, 138.31, 130.16, 127.00, 126.78, 123.11, 118.33, 80.87, 60.54, 51.83, 37.14, 28.46, 20.06. Anal. Calcd for C$_{17}$H$_{23}$NO$_4$ (with 0.1 mol H$_2$O per target): C, 66.47; H, 7.61; N, 4.56. Found: C, 66.26; H, 7.44; N, 4.56.

Methyl 2-Methyl-4-(N-methyl)aminocinnamate (24a)

Methyl2-Methyl-4-[N-(tert-butoxycarbonyl)methyl] aminocinnamate 23a (0.516 g, 1.689 mmol) was taken up into anhydrous DCM (10 mL) under nitrogen gas and cooled in an ice bath. Trifluoroacetic acid (4 mL) was added slowly and the mixture was stirred at room temperature for 1.5 hours. The reaction mixture was concentrated and the residue was taken up into EtOAc and washed with chilled sat. NaHCO$_3$, brine, and dried with Na$_2$SO$_4$. After filtration, the filtrate was concentrated and the filtrate was purified using column chromatography and a 10% to 20% EtOAc/hexane mobile phase gradient to give the product 24a as a yellow solid (0.229 g, 1.116 mmol, 66.1%). TLC (25% EtOAc/hexane)=0.31. Mp 79-83° C. $^1$H NMR (CDCl$_3$, 600 MHz): δ ppm 7.93 (1H, d, J=15.7 Hz), 7.47 (1H, d, J=8.5 Hz), 6.45 (1H, dd, J$_1$=8.5 Hz, J$_2$=2.5 Hz), 6.20 (1H, d, J=15.8 Hz), 4.11 (1H, bs), 3.78 (3H, s), 2.86 (3H, s), 2.39 (3H, s). $^{13}$C NMR (CDCl$_3$, 150 MHz): δ ppm 168.51, 150.94, 142.66, 139.97, 128.13, 122.18, 113.62, 113.10, 110.61, 51.52, 30.41, 20.26. Anal. Calcd for C$_{12}$H$_{15}$NO$_2$: C, 70.22; H, 7.37; N, 6.82. Found: C, 70.00; H, 7.26; N, 6.68.

Methyl 2-Methyl-4-[N-methyl-N-[5-methylene-4-methyl-2-[4-(trifluoromethyl)phenyl]-thiazole]] aminocinnamate (25a)

Methyl ester 24a (0.316 g, 1.540 mmol), thiazole 4b (0.520 g, 1.782 mmol), and NaI (0.328 g, 2.188 mmol) were dried in vacuum desiccator overnight to ensure dry starting reagents. These starting reagents were combined in a two-neck flask under nitrogen and anhydrous DMF (15 mL) was added. The reaction mixture was cooled in ice bath and NaH (60% dispersion in mineral oil, 0.101 g, 2.525 mmol) was added by briefly exposing the system to air. The mixture was warmed to room temperature and stirred for 2.5 hours. The reaction mixture was quenched with water carefully and diluted with ether and neutralized with NaHCO$_3$. Additional water was added to obtain a clear two phase solution. The organic phase was collected and the aqueous phase was extracted with two portions of ether. The organic phases were combined and washed with water, brine, dried with Na$_2$SO$_4$. After filtration, the filtrate was concentrated and the residue was purified by column chromatography with a 5% to 20% EtOAc/hexane mobile phase gradient to give the product 25a as a yellow-orange solid (0.523 g, 1.136 mmol, 73.8%). TLC (25% EtOAc/hexane)=0.33. Mp 151-152° C. $^1$H NMR (CDCl$_3$, 600 MHz): δ ppm 7.96 (2H, d, J=8.2 Hz), 7.93 (1H, d, J=15.8 Hz), 7.64 (2H, d, J=8.2 Hz), 7.53 (1H, d, J=8.8 Hz), 6.66 (1H, dd, J$_1$=8.8 Hz, J$_2$=2.7 Hz), 6.58 (1H, d, J=2.5 Hz), 6.24 (1H, d, 8.8 Hz), 4.67 (2H, s), 3.79 (3H, s), 3.04 (3H, s), 2.51 (3H, s), 2.43 (3H, s). $^{13}$C NMR (CDCl$_3$, 150 MHz): δ ppm 168.35, 163.65, 150.31, 149.90, 142.29, 139.88, 136.73, 131.51 (q, $^2$J$_{FC}$=32.4 Hz), 131.02, 128.18, 126.57, 126.02 (q, $^3$J$_{FC}$=3.5 Hz), 124.03 (q, $^1$J$_{FC}$=271 Hz), 122.88, 114.52, 114.21, 111.08, 51.64, 49.06, 38.33, 20.65, 15.56. Anal. Calcd for C$_{24}$H$_{23}$N$_2$F$_3$O$_2$S: C, 62.60; H, 5.03; N, 6.08. Found: C, 62.36; H, 5.06; N, 6.05.

2-Methyl-4-[N-methyl-N-[5-methylene-4-methyl-2-[4-(trifluoromethyl)phenyl]thiazole]]aminocinnamic Acid (BK-5-15)

Methyl ester 25a (0.400 g, 0.868 mmol) was dissolved in anhydrous THF (10 mL) and 95% ethanol (5 mL) and was cooled in an icebath. Upon, cooling a precipitate formed but then returned to solution after the addition of 3N NaOH (1 mL). The reaction mixture was stirred overnight at room temperature and was then concentrated under reduced pressure. The resulting residue was taken up into EtOAc and washed with acidic water (pH=3, HCl), brine, and dried with Na$_2$SO$_4$. After filtration, the filtrate was concentrated and the residue was purified by column chromatography using a 25% EtOAc/hexane mobile phase that was supplemented with dropwise amounts of acetic acid. The column purified product was collected and recrystallized using 95% ethanol to give BK-5-15 as a yellow solid (0.081 g, 0.181 mmol, 20.9%). TLC (50% EtOAc/hexane)=0.46. Mp 228-230° C. $^1$H NMR (Acetone-d$_6$, 600 MHz): δ ppm 8.10 (2H, d, J=8.1 Hz), 7.90 (1H, d, J=15.8 Hz), 7.79 (2H, d, J=8.3 Hz), 7.64 (1H, d, J=8.7 Hz), 6.78 (1H, dd, J$_1$=9.0 Hz, J$_2$=2.8 Hz), 6.75 (1H, d, J=2.6 Hz), 6.25 (1H, d, J=15.8 Hz), 4.86 (2H, s), 3.10 (3H, s), 2.52 (3H, s), 2.41 (3H, s). $^{13}$C NMR (Acetone-d$_6$, 150 MHz): δ ppm 167.44, 162.18, 150.51, 150.19, 141.91, 139.23, 137.18, 131.77, 130.51 (q, $^2$J$_{FC}$=31.8 Hz), 127.93, 126.38, 125.95 (m), 124.25 (q, $^1$J$_{FC}$=271 Hz), 122.00, 114.21, 113.79, 111.00, 48.08, 37.50, 19.42, 14.60. Anal. Calcd for C$_{23}$H$_{21}$F$_3$N$_2$O$_2$S: C, 61.87; H, 4.74; N, 6.27. Found: C, 61.15; H, 4.86; N, 6.18.

4-Bromo-3-methylbenzaldehyde (21b)

4-Bromo-3-methylbenzonitrile (2.100 g, 10.71 mmol) was dissolved in anhydrous toluene (40 mL) under nitrogen and cooled in dry ice bath to −78° C. DIBAL-H was then added and the reaction mixture was stirred at −78° C. for 45 minutes. Anhydrous methanol (3 mL) followed by 2M H$_2$SO$_4$ (10 mL) were carefully added to the reaction mixture and was stirred overnight at room temperature. The reaction mixture was diluted with EtOAc, washed with water, and dried with Na$_2$SO$_4$. After filtration, the filtrate was concentrated and purified by column chromatography using a 100% hexane to 5% EtOAc/hexane mobile phase gradient. The desired product 21b was collected as a white solid (1.801 g, 9.051 mmol, 84.5%). TLC (25% EtOAc/hexane)=0.70. Mp 120-122° C. $^1$H NMR (CDCl$_3$, 600 MHz): δ ppm 9.95 (1H, s), 7.72 (1H, s), 7.70 (1H, d, J=8.1 Hz), 7.55 (1H, d, J=8.0 Hz), 2.48 (3H, d). $^{13}$C NMR (CDCl$_3$, 600 MHz): δ ppm 191.55, 139.27, 135.53, 133.36, 132.36, 131.58, 128.40, 23.03. Anal. Calcd. for C$_8$H$_7$OBr: C, 48.27; H, 3.54; N, 0.00. Found: C, 48.01; H, 3.56; N, 0.13.

3-Methyl-4-[N-(tert-butoxycarbonyl)methyl]benzaldehyde (22b)

Aldehyde 21b (1.423 g, 7.149 mmol), tert-Butyl-N-methylcarbamate (1.123 g, 8.561 mmol), and Cs$_2$CO$_3$ (3.323 g, 10.15 mmol) were dissolved in anhydrous dioxane (40 mL) and under nitrogen. Xantphos (0.195 g, 0.337 mmol) and Pd$_2$(dba)$_3$ (0.149 g, 0.163 mmol) were measured out in nitrogen bag and added to the reaction flask. The reaction mixture was refluxed with stirring overnight and was then cooled to room temperature before removal of the solvent under reduced pressure. The resulting residue was taken up into EtOAc and water followed by filtration through celite. The EtOAc phase was collected and washed with water, brine, and dried with Na$_2$SO$_4$. After filtration, the filtrate was concentrated and the residue was purified using column chromatography and a 100% hexane to 5% EtOAc/hexane mobile phase gradient to give the desired product 22b as a light-yellow, almost colorless oil (0.837 g, 3.357 mmol, 47.0%). TLC (25% EtOAc/hexane)=0.41. $^1$H NMR (CDCl$_3$, 600 MHz): δ ppm 9.98 (1H, s), 7.75 (1H, s), 7.71 (1H, d, J=7.7 Hz), 3.17 (3H, s), 2.30 (3H, s), 1.53 (3H, s), 1.34 (7H, s). $^{13}$C NMR (CDCl$_3$, 150 MHz): δ ppm 191.84, 154.49, 148.27, 136.80, 135.07, 132.16, 128.46, 128.18, 80.54, 36.69, 28.36, 17.79. Anal. Calcd for C$_{14}$H$_{19}$O$_3$N: C, 67.45; H, 7.68; N, 5.62. Found: C, 67.26; H, 7.73; N, 5.67.

Methyl 3-Methyl-4-[N-(tert-butoxycarbonyl)methyl] aminocinnamate (23b)

Aldehyde 22b (0.736 g, 2.953 mmol) and methyl(triphenylphosphoranylidene)acetate (1.087 g, 3.251 mmol) were dissolved in anhydrous THF (10 mL) and was refluxed for 2 days. The reaction mixture was concentrated with reduced pressure and the residue was taken up into EtOAc and washed in water, brine, and dried with Na$_2$SO$_4$. After filtration, the filtrate was concentrated and the residue was purified using column chromatography and a 100% hexane to 7% EtOAc/hexane mobile phase gradient to give the desired product 23b as a light yellow oil (0.561 g, 1.837 mmol, 62.2%). TLC (25% EtOAc/hexane)=0.43. $^1$H NMR (CDCl$_3$, 600 MHz): δ ppm 7.66 (1H, d, J=16 Hz), 7.37 (1H, s), 7.35 (1H, d, J=7.9 Hz), 7.09 (1H, d, J=7.9 Hz), 6.42 (1H, d, J=15.8 Hz), 3.80 (3H, s), 3.14 (3H, s), 2.23 (3H, s), 1.51 (3H, s), 1.33 (7H, s). $^{13}$C NMR (CDCl$_3$, 150 MHz): δ ppm 167.57, 154.86, 144.47, 144.37, 136.17, 133.16, 130.57, 127.91, 126.50, 117.91, 80.17, 51.87, 36.79, 28.38, 17.75. Anal. Calcd for C$_{17}$H$_{23}$O$_4$N: C, 66.86; H, 7.59; N, 4.59. Found: C, 66.57; H, 7.57; N, 4.55.

Methyl 3-Methyl-4-(N-methyl)aminocinnamate (24b)

Methyl ester 23b (1.359 g, 4.450 mmol) was dissolved in anhydrous DCM (25 mL) under nitrogen gas and cooled in ice bath. Trifluoroacetic acid (7 mL, 91.48 mmol) was carefully added and the reaction mixture was stirred for 2 hours at room temperature. The reaction mixture was then quenched with an aqueous saturated solution of NaHCO$_3$. The organic phase was collected and washed with water, brine, and dried with Na$_2$SO$_4$. After filtration, the solution was concentrated and column chromatography was attempted to purify the crude material along with recrystallization. Purification methods were unsuccessful, so the crude yellow solid 24b (0.758 g, 3.693 mmol, 83.0%) was moved to the next step. TLC (25% EtOAc/hexane)=0.36. $^1$H NMR (CDCl$_3$, 400 MHz): δ ppm 7.63 (1H, d, J=16.0 Hz), 7.35 (1H, dd, J$_1$=8.4 Hz, J$_2$=2.0 Hz), 6.57 (1H, d, J=8.4 Hz), 6.24 (1H, d, J=15.6 Hz), 3.77 (3H, s), 2.93 (3H, s), 2.13 (3H, s).

Methyl 2-Methyl-4-[N-methyl-N-[5-methylene-4-methyl-2-[4-(trifluoromethyl)phenyl]-thiazole]] aminocinnamate (25b)

Methyl ester 24b (0.200 g, 0.974 mmol), thiazole 4b (0.340 g, 1.166 mmol), and NaI (0.215 g, 1.434 mmol) were dried in vacuum desiccator overnight to ensure dry starting reagents. These starting reagents were combined in a two-neck flask under nitrogen and anhydrous acetonitrile (25 mL) was added. The reaction mixture was cooled in ice bath and N,N-Diisopropylethylamine (0.255 g, 1.464 mmol) was added. The mixture was warmed to room temperature and stirred overnight. TLC showed an incomplete reaction and the mixture was heated to 80° C. for 6 hours. The reaction mixture was concentrated under reduced pressure and the solid residue was taken up into DCM and water. The organic phase was collected and the aqueous phase was extracted with a separate portion of DCM. The two organic phases were combined and dried with Na$_2$SO$_4$. After filtration, the filtrate was concentrated and the residue was purified by column chromatography with a 5% to 13% EtOAc/hexane mobile phase gradient to give the product 25b as a yellow solid (0.341 g, 0.740 mmol, 76.0%). TLC (25% EtOAc/hexane)=0.50. Mp 92-94° C. $^1$H NMR (CDCl$_3$, 600 MHz): δ ppm 8.00 (2H, d, J=8.1 Hz), 7.65 (3H, m), 7.39 (1H, d, J=1.6 Hz), 7.35 (1H, dd, J$_1$=8.2 Hz, J$_2$=2.0 Hz), 7.04 (1H, d, J=8.2 Hz), 6.37 (1H, d, J=16.0 Hz), 4.23 (2H, s), 3.80 (3H, s), 2.72 (3H, s), 2.43 (6H, s). $^{13}$C NMR (CDCl$_3$, 150 MHz): δ ppm 167.86, 164.05, 153.14, 151.00, 144.71, 136.94, 133.26, 131.56, 131.31, 131.13 (m), 129.73, 126.92, 126.57, 126.02 (q, $^3$J$_{FC}$=3.5 Hz), 124.98, 124.08 (q, $^2$J$_{FC}$=270 Hz), 120.39, 116.31, 51.98, 51.79, 41.06, 18.78, 15.50. Anal. Calcd for C$_{24}$H$_{23}$F$_3$N$_2$O$_2$S: C, 62.60; H, 5.03; N, 6.08. Found: C, 62.08; H, 5.06; N, 5.93.

2-Methyl-4-[N-methyl-N-[5-methylene-4-methyl-2-[4-(trifluoromethyl)phenyl]thiazole]]aminocinnamic Acid (BK-5-99)

Methyl ester 25b (0.220 g, 0.478 mmol) was dissolved in 95% ethanol (6 mL) and THF (6 mL). 3N NaOH (2 mL) was added and the mixture was stirred for 3 days at room temperature. 3N HCl was added until the mixture reached a pH of 3. The mixture was concentrated under reduced pressure and the residue was taken up into EtOAc. The solution was washed with chilled a saturated NaHCO$_3$ aqueous solution, brine, and dried with Na$_2$SO$_4$. After filtration, the filtrate was concentrated and the crude product purified using column chromatography and a 25% EtOAc/hexane mobile phase that was supplemented with dropwise amounts of acetic acid. The column product was recrystallized using 95% ethanol to give BK-5-99 as a pale yellow solid (0.170 g, 0.382 mmol, 79.8%). $^1$H NMR (Acetone-d$_6$, 600 MHz): δ ppm 10.66 (1H, bs), 8.14 (2H, d, J=8.1 Hz), 7.81 (2H, d, J=8.2 Hz), 7.62 (1H, d, J=16.0 Hz), 7.55 (1H, s), 7.48 (1H, dd, $J_1$=8.2 Hz, $J_2$=1.7 Hz), 7.19 (1H, d, J=8.3 Hz), 6.44 (1H, d, J=16.0 Hz), 4.37 (2H, s), 2.75 (3H, s), 2.45 (3H, s), 2.42 (3H, s). $^{13}$C NMR (Acetone-$d_6$, 150 MHz): δ ppm 168.01, 163.73, 154.14, 151.99, 145.41, 138.29, 134.14, 132.76, 131.93, 131.45 (q, $^2J_{FC}$=31.9 Hz), 130.58, 127.81, 127.35, 126.92 (q, $^3J_{FC}$=3.8 Hz), 125.24 (q, $^1J_{FC}$=270 Hz), 121.48, 117.46, 52.15, 41.54, 18.75, 15.54. $^{19}$F NMR (Acetone-d6, 376 MHz): δ ppm −63.62 (3F, s). Anal. Calcd for $C_{23}H_{21}F_3N_2O_2S$: C, 61.87; H, 4.74; N, 6.27. Found: C, 61.69; H, 4.58; N, 6.14.

3-Ethyl-N-(tert-butoxycarbonyl)aniline (27a)

3-Ethylaniline (3.0 mL, 0.024 mol) and di-tert-butyldicarbonate (5.840 g, 0.026 mol) were dissolved in anhydrous THF (40 mL) under inert gas. The mixture was refluxed at 65° C. overnight. The reaction mixture was then concentrated under reduced pressure and the resulting residue was taken up into EtOAc and washed with saturated $NaHCO_3$ solution, water, brine, and dried with $Na_2SO_4$. After filtration and evaporation of the solvent, the crude product was purified with column chromatography using 10% EtOAc/hexane. The purified product 27a was collected as an orange oil containing EtOAc (5.837 g, 0.026 mol, 110%). TLC $R_f$ (25% EtOAc/Hexane)=0.64. $^1$H NMR (CDCl$_3$, 600 MHz): δ ppm 7.20 (1H, m), 7.12 (1H, d, J=7.7 Hz), 6.88 (1H, d, J=7.5 Hz), 6.43 (1H, bs), 2.62 (2H, q, J=7.6 Hz), 1.52 (9H, s), 1.22 (3H, t, J=7.6 Hz). $^{13}$C NMR (CDCl$_3$, 150 MHz): δ ppm 152.91, 145.47, 138.42, 129.00, 122.77, 118.15, 115.97, 80.52, 29.06, 28.50, 15.70. Anal. Calcd for $C_{13}H_{19}NO_2$: C, 70.56; H, 8.65; N, 6.33. Found: C, 70.27; H, 8.52; N, 6.10.

3-Ethyl-[N-(tert-butoxycarbonyl)methyl]aniline (28a)

3-Ethyl-(N-tert-butoxycarbonyl)aniline 27a (4.547 g, 20.55 mmol) was dissolved in anhydrous DMF (50 mL) and cooled in an icebath. NaH (60% dispersion in mineral oil, 1.234 g, 30.85 mmol) was added and the mixture was stirred for 45 minutes followed by addition of iodomethane (3.8 mL, 61.04 mmol). The reaction mixture was stirred overnight at room temperature and quenched with 50% saturated $NaHCO_3$ and extracted with two portions of ether. The ether extracts were combined and washed with brine, dried with $Na_2SO_4$, and concentrated. The crude material was purified by column chromatography using 5% EtOAc/hexane to give the desired product 28a as a yellow-orange oil (4.318 g, 18.35 mmol, 89.3%). TLC $R_f$ (25% EtOAc/Hexane)=0.62. $^1$H NMR (CDCl$_3$, 600 MHz): δ ppm 7.24 (1H, m), 7.07 (1H, s), 7.03 (1H, d, J=7.9 Hz), 7.00 (1H, d, J=7.6 Hz), 3.25 (3H, s), 2.66 (2H, q, J=7.6 Hz), 1.45 (9H, s), 1.23 (3H, t, J=7.6 Hz). $^{13}$C NMR (CDCl$_3$, 150 MHz): δ ppm 155.00, 144.84, 143.94, 128.53, 125.26, 125.07, 122.80, 80.26, 37.53, 28.90, 28.50, 15.65. Anal. Calcd for $C_{14}H_{21}NO_2$: C, 71.46; H, 9.00; N, 5.95. Found: C, 71.17; H, 8.89; N, 5.85.

3-Ethyl-(N-methyl)aniline (29a)

3-Ethyl-[N-(tert-butoxycarbonyl)methyl]aniline 27a (3.582 g, 15.22 mmol) was dissolved in anhydrous DCM (40 mL) under inert gas and cooled in an icebath. Trifluoroacetic acid (10 mL, 0.13 mol) was slowly added and the mixture was stirred at r.t. for 1.5 hours. The reaction mixture was diluted with DCM and neutralized with chilled saturated $NaHCO_3$. The organic phase was collected and washed with water, brine, dried with $Na_2SO_4$, and concentrated. The crude material was purified by column chromatography using a gradient of 5% EtOAc/hexane to 50% EtOAc/hexane and appeared to oxidize upon collection to give the desired product 29a as a crude black oil with trace EtOAc (2.845 g). This material was used in the next step without further purification. TLC $R_f$(25% EtOAc/Hexane)=0.61. $^1$H NMR (CDCl$_3$, 600 MHz): δ ppm 7.36 (1H, m), 7.28 (2H, m), 7.24 (1H, d, J=7.6 Hz), 2.99 (3H, s), 2.66 (2H, q, J=7.6 Hz), 1.22 (3H, t, J=7.6 Hz). $^{13}$C NMR (CDCl$_3$, 150 MHz): δ ppm 147.25, 137.64, 130.31, 129.07, 121.51, 119.34, 38.08, 28.73, 15.24.

3-Ethyl-[N-methyl-N-[(5-methylene-4-methyl-2-(4-(trifluoromethyl)phenyl)]thiazole]aniline (30a)

3-Ethyl-(N-methyl)aniline 29a (0.693 g, 5.125 mmol), thiazole 4b (1.478 g, 5.069 mmol), and NaI (0.790 g, 5.271 mmol) were dissolved in anhydrous DMF (20 mL) under inert gas and cooled in an icebath. NaH (60% dispersion in mineral oil, 0.314 g, 7.85 mmol) was carefully added to the reaction by briefly exposing the system to air. The reaction mixture was stirred for 3 hours at room temperature and quenched with a 50% dilution of sat. $NaHCO_3$. The mixture was extracted with three portions of ether which were combined, washed with brine, dried with $Na_2SO_4$, and concentrated. The crude material was purified by column chromatography using a gradient of 5% EtOAc/hexane to 30% EtOAc/hexane to give the desired product 30a as an orange oil (0.650 g, 1.66 mmol, 32.8%). TLC $R_f$ (25% EtOAc/Hexane)=0.56. $^1$H NMR (CDCl$_3$, 600 MHz): δ ppm 7.96 (2H, d, J=8.1 Hz), 7.63 (2H, d, J=8.3 Hz), 7.19 (1H, m), 6.68 (3H, m), 4.61 (2H, s), 2.97 (3H, s), 2.62 (2H, q, J=7.6 Hz), 2.50 (3H, s), 1.24 (3H, t, J=7.6 Hz). $^{13}$C NMR (CDCl$_3$, 150 MHz): δ ppm 163.34, 150.07, 149.04, 145.54, 136.87, 131.18 (q, $^2J_{FC}$=32.5 Hz), 129.27, 126.37, 125.82 (m), 123.96 (q, $^1J_{FC}$=270 Hz), 118.00, 113.45, 111.24, 49.89, 38.41, 29.32, 15.69, 15.44. Anal. Calcd. for $C_{21}H_{21}F_3N_2S$: C, 64.60; H, 5.42; N, 7.17. Found: C, 64.31; H, 5.48; N, 7.01.

2-Ethyl-4-[N-methyl-N-[5-methylene-4-methyl-2-[4-(trifluoromethyl)phenyl]thiazole]]aminobenzaldehyde (31a)

Anhydrous DMF (1.0 mL, 12.92 mmol) was added to reaction flask and cooled in an icebath. $POCl_3$ (0.5 mL, 5.364 mmol) was slowly added and the mixture was stirred for 15 minutes. Aniline product 30a (0.612 g, 1.567 mmol) from the previous reaction was dissolved with anhydrous DMF (1 mL) in a separate flask. The aniline product solution was carefully transferred to the reaction flask containing the Vilsmeier reagent. The reaction mixture was stirred for 2.5 hours at 70° C. and then allowed to cool before being poured onto crushed ice. This mixture was neutralized with 3N NaOH until a pH of 10 was reached. This mixture produced no precipitate and was extracted with two portions of ether. The ether extracts were combined, washed with brine, dried with $Na_2SO_4$, and concentrated. The crude material was purified by column chromatography using a gradient of 5% EtOAc/hexane to 20% EtOAc/hexane to give the desired product 31a as a yellow-orange solid (0.432 g, 1.032 mmol, 65.9%). TLC $R_f$(25% EtOAc/Hexane)=0.28. Mp 97-98° C. $^1$H NMR (CDCl$_3$, 600 MHz): δ ppm 10.02 (1H, s), 7.95 (2H, d, J=8.2 Hz), 7.73 (1H, d, J=8.7 Hz), 7.63 (2H, d, J=8.3 Hz), 6.69 (1H, dd, $J_1$=8.7 Hz $J_2$=2.6 Hz), 6.57 (1H, d, J=2.5 Hz), 4.74 (2H, s), 3.12 (3H, s), 3.02 (2H, q, J=7.5 Hz), 2.53 (3H, s), 1.26 (3H, t, J=7.5 Hz). $^{13}$C NMR (CDCl$_3$, 150 MHz): δ ppm 190.26, 163.76, 152.40, 150.51, 149.64, 136.59, 134.89, 131.60 (q, $^2J_{FC}$=32.5 Hz), 130.33, 126.58, 126.02 (m), 123.99 (q, $^1J_{FC}$=271 Hz), 123.95, 112.80, 109.78, 48.65, 38.30, 26.68, 16.42, 15.56. Anal. Calcd. for C$_{22}$H$_{21}$F$_3$N$_2$OS: C, 63.14; H, 5.06; N, 6.69. Found: C, 62.85; H, 5.19; N, 6.58.

Ethyl 2-Ethyl-4-[N-methyl-N-[5-methylene-4-methyl-2-[4-(trifluoromethyl)phenyl]thiazole]]aminocinnamate (32a)

Triethylphosphonoacetate (0.24 mL, 1.21 mmol) was taken up into anhydrous THF (5 mL) in an ice bath and under inert gas. NaH (60% dispersion in mineral oil, 0.055 g, 1.38 mmol) was added by briefly exposing the system to air. In a separate flask, aldehyde 31a (0.385 g, 0.920 mmol) was dissolved in anhydrous THF (5 mL) under inert gas. After the triethylphosphonoacetate mixture had stirred for 30 minutes, the aldehyde solution was added slowly. The reaction mixture was stirred for 3 hours at room temperature and upon completion was quenched with sat. NH$_4$Cl and was extracted with three portions of EtOAc. The combined organic layers were washed with brine, dried with Na$_2$SO$_4$, and concentrated. The crude material was purified by column chromatography using a gradient of 10% EtOAc/hexane to 20% EtOAc/hexane to give the desired product 32a as a light yellow solid (0.300 g, 0.614 mmol, 66.7%). TLC R$_f$ (25% EtOAc/Hexane)=0.38. Mp 127-128° C. $^1$H NMR (CDCl$_3$, 600 MHz): δ ppm 7.95 (3H, m), 7.63 (2H, d, J=8.3 Hz), 7.55 (1H, d, J=8.8 Hz), 6.65 (1H, dd, J$_1$=8.8 Hz J$_2$=2.7 Hz), 6.60 (1H, d, J=2.7 Hz), 6.24 (1H, d, J=15.7 Hz), 4.67 (2H, s), 4.25 (2H, q, J=7.1 Hz), 3.04 (3H, s), 2.77 (2H, q, J=7.6 Hz), 2.52 (3H, s), 1.33 (3H, t, J=7.1 Hz), 1.23 (3H, t, J=7.6 Hz). $^{13}$C NMR (CDCl$_3$, 150 MHz): δ ppm 167.96, 163.57, 150.34, 150.20, 146.00, 141.78, 136.84, 131.45 (q, $^2J_{FC}$=32.6 Hz), 131.15, 128.23, 126.53, 125.98 (m), 124.05 (q, $^1J_{FC}$=270 Hz), 122.02, 114.81, 112.97, 111.11, 60.31, 49.03, 38.26, 27.10, 16.28, 15.59, 14.55. Anal. Calcd. for C$_{26}$H$_{27}$F$_3$N$_2$O$_2$S: C, 63.92; H, 5.57; N, 5.73. Found: C, 63.66; H, 5.61; N, 5.58.

2-Ethyl-4-[N-methyl-N-[5-methylene-4-methyl-2-[4-(trifluoromethyl)phenyl]thiazole]]aminocinnamic Acid (BK-5-67)

Ethyl ester 32a (0.279 g, 0.571 mmol) was dissolved in 95% ethanol (8 mL) and THF (8 mL). 3N NaOH (2 mL) was added and the mixture was stirred overnight at room temperature. The reaction was determined incomplete and additional 3N NaOH (2 mL) was added. The mixture was stirred for an additional 24 hours and was neutralized with 1N HCl to a pH of 3. The solvent was removed under reduced pressure and the residue was taken up into EtOAc, washed with sat. NaHCO$_3$, brine, dried with Na$_2$SO$_4$, and concentrated. The crude material was purified by column chromatography using a 25% EtOAc/hexane to 50% EtOAc/hexane gradient supplemented with dropwise amounts of acetic acid to give the desired product BK-5-67 as a yellow solid (0.181 g, 0.393 mmol, 68.8%). TLC R$_f$ (50% EtOAc/Hexane)=0.45. Mp 216-218° C. $^1$H NMR (Acetone-d6, 600 MHz): δ ppm 8.10 (2H, d, J=8.1 Hz), 7.93 (1H, d, J=15.7 Hz), 7.78 (2H, d, J=8.3 Hz), 7.66 (1H, d, J=8.8 Hz), 6.78 (2H, m), 6.26 (1H, d, J=15.7 Hz), 4.86 (2H, s), 3.10 (3H, s), 2.77 (2H, q, J=7.6 Hz), 2.52 (3H, s), 1.20 (3H, t, J=7.6 Hz). $^{13}$C NMR (Acetone-d6, 150 MHz): δ ppm 168.47, 163.20, 151.53, 151.40, 146.50, 142.60, 138.17, 132.74, 131.48 (q, $^2J_{FC}$=32.1 Hz), 129.00, 127.38, 126.95 (m), 125.25 (q, $^1J_{FC}$=271 Hz), 122.06, 114.91, 113.90, 112.14, 49.10, 38.49, 27.54, 16.73, 15.61. $^{19}$F NMR (Acetone-d6, 376 MHz): δ ppm −63.66. Anal. Calcd. for C$_{24}$H$_{23}$F$_3$N$_2$O$_2$S: C, 62.60; H, 5.03; N, 6.08. Found: C, 62.45; H, 5.07; N, 6.24.

3-Isopropyl-N-(tert-butoxycarbonyl)aniline (27b)

3-Isopropylaniline (1.087 g, 8.039 mmol) and di-tert-butyl dicarbonate (1.988 g, 9.109 mmol) were dissolved in THF (50 mL) under inert gas and heated to reflux at 65° C. for 3 days. The mixture was cooled to room temperature and concentrated under reduced pressure. The resulting residue was taken up into EtOAc and washed with sat. NaHCO$_3$, water, brine, dried with Na$_2$SO$_4$, and concentrated. The crude sample was purified using column chromatography with a 5% EtOAc/hexane mobile phase to give the product 27b as a light orange solid (1.660 g, 7.054 mmol, 87.7%). TLC R$_f$(25% EtOAc/Hexane)=0.70. Mp 44-45° C. $^1$H NMR (CDCl$_3$, 600 MHz): δ ppm 7.25 (1H, br-s), 7.21 (1H, m), 7.15 (1H, d, J=7.4 Hz), 6.91 (1H, d, J=7.5 Hz), 6.47 (1H, br-s), 2.87 (1H, sept., J=7.0 Hz), 1.52 (9H, s), 1.24 (6H, d, J=7.0 Hz). $^{13}$C NMR (CDCl$_3$, 150 MHz): δ ppm 152.92, 150.08, 138.40, 128.99, 121.28, 116.86, 116.17, 80.48, 34.31, 28.50, 24.07. Anal. Calcd for C$_{14}$H$_{21}$NO$_2$: C, 71.46; H, 9.00; N, 5.95. Found: C, 71.72; H, 9.03; N, 5.86.

3-Isopropyl-[N-methyl-N-(tert-butoxycarbonyl)]aniline (28b)

3-Isopropyl-N-(tert-butoxycarbonyl)aniline 27b (3.148 g, 13.38 mmol) was dissolved in anhydrous DMF (50 mL) and cooled in an icebath. NaH (60% dispersion in oil, 0.805 g, 20.13 mmol) was added and the mixture was stirred for 30 minutes followed by addition of iodomethane (2.5 mL, 40.16 mmol). The reaction mixture was stirred overnight at room temperature and quenched with a 50% NaHCO$_3$ solution and extracted twice with ether. The ether extracts were combined and washed with brine, dried with Na$_2$SO$_4$, and concentrated. The crude material was purified by column chromatography using a 100% Hexane to 5% EtOAc/Hexane gradient giving the desired compound 28b as an orange oil (2.769 g, 11.10 mmol, 83.0%). TLC R$_f$(25% EtOAc/Hexane)=0.73. $^1$H NMR (CDCl$_3$, 600 MHz): δ ppm 7.24 (1H, t, J=7.8 Hz), 7.09 (1H, bs), 7.03 (2H, dd, J$_1$=7.7 Hz, J$_2$=1.6 Hz), 3.26 (3H, s), 2.89 (1H, J=6.9 Hz), 1.45 (9H, s), 1.25 (6H, d, J=6.9 Hz). $^{13}$C NMR (CDCl$_3$, 150 MHz): δ ppm 155.00, 149.45, 143.91, 128.50, 124.03, 123.61, 122.77, 80.23, 37.55, 34.19, 28.51, 24.10. Anal. Calcd for C$_{15}$H$_{23}$NO$_2$: C, 72.25; H, 9.30; N, 5.62. Found: C, 72.53; H, 9.27; N, 5.71.

3-Isopropyl-(N-methyl)aniline (29b)

3-Isopropyl-[N-methyl-N-(tert-butoxycarbonyl)]aniline 28b (2.409 g, 9.661 mmol) was dissolved in anhydrous DCM (40 mL) under inert gas and cooled in an icebath. Trifluoroacetic acid (7.4 mL, 96.70 mmol) was slowly added and the mixture was stirred at r.t. for 2 hours. The reaction mixture was diluted with DCM and neutralized with chilled saturated NaHCO$_3$. The organic phase was collected and washed with water, brine, dried with Na$_2$SO$_4$, and concentrated. The crude material was purified by column chromatography using a gradient of 5% EtOAc/hexane to 50% EtOAc/hexane and appeared to oxidize upon collection to give the desired product 29b as a crude black oil with trace EtOAc (1.733 g). This material was used in the next step without further purification. TLC $R_f$ (25% EtOAc/Hexane) =0.51. $^1$H NMR (CDCl$_3$, 600 MHz): δ ppm 7.36 (1H, m), 7.26 (1H, m), 2.99 (3H, s), 2.92 (1H, sept., J=6.9 Hz), 1.24 (6H, t, J=6.9 Hz). $^{13}$C NMR (CDCl$_3$, 150 MHz): δ ppm 151.94, 137.92, 130.31, 127.44, 120.05, 119.33, 37.97, 34.15, 23.79.

3-Isopropyl-[N-methyl-N-[(5-methylene-4-methyl-2-(4-(trifluoromethyl)phenyl)]thiazole]aniline (30b)

3-Isopropyl-(N-methyl)aniline 29b (1.352 g, 9.059 mmol), thiazole 4b (1.755 g, 6.016 mmol), and NaI (0.990 g, 6.604 mmol) were dissolved in anhydrous DMF (30 mL) under inert gas and cooled in an icebath. NaH (60% dispersion in mineral oil, 0.363 g, 9.075 mmol) was carefully added to the reaction by briefly exposing the system to air. The reaction mixture was stirred for 3 hours at room temperature and quenched with a 50% dilution of sat. NaHCO$_3$. The mixture was extracted with three portions of ether which were combined, washed with brine, dried with Na$_2$SO$_4$, and concentrated. The crude material was purified by column chromatography using a gradient of 100% hexane to 5% EtOAc/hexane to give the desired product 30b as an orange oil (1.657 g, 4.096 mmol, 68.1%). TLC $R_f$ (25% EtOAc/Hexane)=0.58. $^1$H NMR (CDCl$_3$, 600 MHz): δ ppm 7.99 (2H, d, J=8.2 Hz), 7.66 (2H, d, J=8.3 Hz), 7.23 (1H, t, J=8.1 Hz), 6.75 (2H, m), 6.70 (1H, m), 4.63 (2H, s), 3.00 (3H, s), 2.88 (1H, sept., J=6.9 Hz), 2.52 (3H, s), 1.27 (6H, d, J=6.9 Hz). $^{13}$C NMR (CDCl$_3$, 150 MHz): δ ppm 163.55, 162.66, 150.33, 136.97, 133.67, 131.31 (q, $^2J_{FC}$=32.4 Hz), 129.40, 127.58, 126.51, 125.97 (m), 124.08 (q, $^1J_{FC}$=271 Hz), 116.74, 112.41, 111.69, 50.17, 38.62, 34.65, 24.18, 15.57. Anal. Calcd. for C$_{22}$H$_{23}$F$_3$N$_2$S: C, 65.33; H, 5.73; N, 6.93. Found: C, 65.06; H, 5.67; N, 6.83.

2-Isopropyl-4-[N-methyl-N-[5-methylene-4-methyl-2-[4-(trifluoromethyl)phenyl]thiazole]]aminobenzaldehyde (31b)

Anhydrous DMF (1.0 mL, 12.92 mmol) was added to reaction flask and cooled in an icebath. POCl$_3$ (0.95 mL, 10.19 mmol) was slowly added and the mixture was stirred for 15 minutes. Aniline product 30b (1.156 g, 2.858 mmol) from the previous reaction was dissolved with anhydrous DMF (2.4 mL) in a separate flask. The aniline product solution was carefully transferred to the reaction flask containing the Vilsmeier reagent. The reaction mixture was stirred for 2.5 hours at 70° C. and was then allowed to cool to room temperature before being poured into ice-cold 1N NaOH forming an orange precipitate. The precipitate was filtered off but gave a sticky solid that could not be easily collected. The solid was dissolved in ether and combined with two ether extracts collected from the filtrate. The ether extracts were washed with brine, dried with Na$_2$SO$_4$, and concentrated. The crude material was purified by column chromatography using a gradient of 5% EtOAc/hexane to 10% EtOAc/hexane to give the desired product 31b as a yellow oil with some impurities (0.414 g, 0.957 mmol, 33.5%). TLC $R_f$ (25% EtOAc/Hexane)=0.28. $^1$H NMR (CDCl$_3$, 600 MHz): δ ppm 10.08 (1H, s), 7.96 (2H, d, J=8.2 Hz), 7.74 (1H, d, J=8.8 Hz), 7.64 (2H, d, J=8.3 Hz), 6.72 (1H, d, J=2.5 Hz), 6.68 (1H, dd, J$_1$=8.7 Hz J$_2$=2.6 Hz), 4.74 (2H, s), 4.01 (1H, sept. J=6.8 Hz), 3.13 (3H, s), 2.54 (3H, s), 1.28 (6H, d, J=6.8 Hz). $^{13}$C NMR (CDCl$_3$, 150 MHz): δ ppm 190.30, 163.81, 154.01, 152.53, 150.52, 136.59, 135.09, 131.62 (q, $^2J_{FC}$=32.5 Hz), 130.39, 126.60, 126.04 (m), 124.00 (q, $^1J_{FC}$=270 Hz), 123.49, 109.64, 108.85, 48.74, 38.37, 28.07, 23.91, 15.58. Anal. Calcd. for C$_{23}$H$_{23}$F$_3$N$_2$OS: C, 63.87; H, 5.36; N, 6.48. Found: C, 61.72; H, 5.10; N, 6.22.

Ethyl 2-Isopropyl-4-[N-methyl-N-[5-methylene-4-methyl-2-[4-(trifluoromethyl)phenyl]thiazole]] aminocinnamate (32b)

Triethylphosphonoacetate (0.28 mL, 1.41 mmol) was taken up into anhydrous THF (5 mL) in an ice bath and under inert gas. NaH (60% dispersion in mineral oil, 0.065 g, 1.63 mmol) was added by briefly exposing the system to air. In a separate flask, aldehyde 31b (0.470 g, 1.086 mmol) was dissolved in anhydrous THF (5 mL) under inert gas. After the triethylphosphonoacetate mixture had stirred for 30 minutes, the aldehyde solution was added slowly. The reaction mixture was stirred for 3 hours at room temperature and upon completion was quenched with sat. NH$_4$Cl and was extracted with three portions of EtOAc. The combined organic layers were washed with brine, dried with Na$_2$SO$_4$, and concentrated. The crude material was purified by column chromatography using a gradient of 10% EtOAc/hexane to 15% EtOAc/hexane to give the desired product 32b as a yellow solid (0.371 g, 0.739 mmol, 68.0%). TLC $R_f$ (25% EtOAc/Hexane)=0.35. Mp 99-100° C. $^1$H NMR (CDCl$_3$, 600 MHz): δ ppm 8.05 (1H, d, J=15.7 Hz), 7.95 (2H, d, J=8.2 Hz), 7.63 (2H, d, J=8.3 Hz), 7.53 (1H, d, J=8.8 Hz), 6.69 (1H, d, J=2.6 Hz), 6.65 (1H, dd, J$_1$=8.7 Hz J$_2$=2.6 Hz), 6.23 (1H, d, J=15.6 Hz), 4.67 (2H, s), 4.25 (2H, q, J=7.1 Hz), 3.38 (1H, sept., J=6.8 Hz), 3.05 (3H, s), 2.52 (3H, s), 1.33 (3H, t, J=7.1 Hz), 1.25 (6H, d, J=6.8 Hz). $^{13}$C NMR (CDCl$_3$, 150 MHz): δ ppm 167.92, 163.62, 150.36, 150.22, 149.93, 141.78, 136.80, 131.45 (q, $^2J_{FC}$=32.7 Hz), 128.31, 126.54, 126.00 (m), 124.04 (q, $^1J_{FC}$=271 Hz), 121.88, 115.40, 111.03, 109.44, 60.33, 49.18, 38.37, 29.22, 23.87, 15.60, 14.55. Anal. Calcd. for C$_{27}$H$_{29}$F$_3$N$_2$O$_2$S: C, 64.52; H, 5.82; N, 5.57. Found: C, 64.45; H, 5.83; N, 5.63.

2-Isopropyl-4-[N-methyl-N-[5-methylene-4-methyl-2-[4-(trifluoromethyl)phenyl]thiazole]]aminocinnamic Acid (BK-5-82)

Ethyl ester 32b (0.327 g, 0.651 mmol) was dissolved in 95% ethanol (8 mL) and THF (8 mL). 3N NaOH (3 mL) was added and the mixture was stirred overnight at room temperature. The reaction was determined incomplete and additional 3N NaOH (3 mL) was added. The mixture was stirred for an additional 24 hours and was neutralized with 3N HCl to a pH of 3. The organic solvent was removed under reduced pressure and the residue was taken up into EtOAc, washed with sat. NaHCO$_3$, brine, dried with Na$_2$SO$_4$, and concentrated. The crude material was purified by column chromatography using a 15% EtOAc/hexane to 50% EtOAc/hexane gradient supplemented with dropwise amounts of acetic acid to give the desired product BK-5-82 as a yellow solid (0.179 g, 0.377 mmol, 57.9%). TLC $R_f$ (50% EtOAc/hexane)=0.46. Mp 218-220° C. $^1$H NMR (Acetone-d6, 600 MHz): δ ppm 10.49 (1H, bs), 8.10 (2H, d, J=8.2 Hz), 8.04 (1H, d, J=15.8 Hz), 7.78 (2H, d, J=8.3 Hz), 7.64 (1H, d, J=8.8 Hz), 6.81 (1H, d, J=2.6 Hz), 6.77 (1H, dd, J$_1$=8.8 Hz, J$_2$=2.6 Hz), 6.25 (1H, d, J=15.6 Hz), 4.88 (2H, s), 3.37 (1H, sept., J=6.8 Hz), 3.12 (3H, s), 2.53 (3H, s), 1.25 (6H, d, J=6.8 Hz). $^{13}$C NMR (Acetone-d6, 150 MHz): δ ppm 168.36, 163.12, 151.38, 150.21, 142.45, 138.07, 132.73, 131.39 (q, $^2J_{FC}$=32.3 Hz), 128.97, 127.27, 126.84 (m), 125.14 (q, $^1J_{FC}$=270 Hz), 121.73, 115.37, 111.89, 110.09, 49.13, 38.51, 23.94, 15.54. $^{19}$F NMR (Acetone-d6, 376 MHz): δ ppm −63.66. Anal. Calcd. for $C_{25}H_{25}F_3N_2O_2S$: C, 63.28; H, 5.31; N, 5.90. Found: C, 63.18; H, 5.33; N, 5.98.

Ethyl 5-Methyl-2-[4-(trifluoromethyl)phenyl]-1,3-thiazole-4-carboxylate (33)

2-Ketobutyric acid (3.245 g, 0.032 mol) was dissolved in anhydrous DCM (30 mL) under nitrogen gas. Bromine (1.7 mL, 0.033 mol) was slowly added and the reaction mixture was stirred at room temperature for 15 minutes followed by evaporation of the solvent under reduced pressure. Toluene was added and immediately removed under reduced pressure. 4-(Trifluoromethyl)thiobenzamide (6.224 g, 0.303 mol) was added to the residue, dissolved in 95% ethanol, and refluxed overnight. The solvent was then removed and the residue was purified by column chromatography using a DCM mobile phase to give 33 as a white solid (4.140 g, 13.130 mmol, 43.3%). TLC (25% EtOAc/hexane)=0.52. Mp 91° C. $^1$H NMR (CDCl$_3$, 600 MHz): δ ppm 8.02 (2H, d, J=8.1 Hz), 7.67 (2H, d, J=8.16 Hz), 4.45 (2H, q, J=7.14 Hz), 2.80 (3H, s), 1.43 (3H, s). $^{13}$C NMR (CDCl$_3$, 150 MHz): δ ppm 162.51, 161.91, 145.57, 142.91, 136.08, 131.93 (q, $^2J_{FC}$=32.5 Hz), 130.61, 126.98, 125.98 (q, $^3J_{FC}$=4.1 Hz), 123.92 (q, $^1J_{FC}$=270 Hz), 61.44, 14.48, 13.54. Anal. Calcd. for $C_{14}H_{12}F_3NO_2S$: C, 53.33; H, 3.84; N, 4.44. Found: C, 53.19; H, 3.93; N, 4.35.

4-Hydroxymethyl-5-methyl-2-[4-(trifluoromethyl)phenyl]thiazole (34)

Ethyl ester 33 (3.284 g, 10.416 mmol) was dissolved in anhydrous THF (30 mL) under nitrogen gas. The mixture was cooled in icebath and a chilled 2.0 M solution of LAH in THF (5.2 mL, 10.4 mmol) was added slowly. The reaction mixture was stirred in ice bath for 15 minutes before removing the ice bath to allow warming to room temperature. The reaction mixture stirred for 90 minutes and was quenched with water and dried with Na$_2$SO$_4$. After filtration, the filtrate was concentrated and the residue was purified by column chromatography using a 10% EtOAc/hexane to 50% EtOAc/hexane mobile phase gradient to give 34 as a yellow solid (1.663 g, 6.086 mmol, 58.5%). TLC (25% EtOAc/hexane)=0.16. Mp 112° C. Anal. Calcd. for $C_{12}H_{10}F_3NOS$: C, 52.74; H, 3.69; N, 5.13. Found: C, 52.67; H, 3.77; N, 5.11.

4-Chloromethyl-5-methyl-2-[4-(trifluoromethyl)phenyl]thiazole (35)

Alcohol 34 (1.606 g, 5.877 mmol) was dissolved in anhydrous DCM (40 mL) under nitrogen gas and triethylamine (1.65 mL, 11.838 mmol) was added at room temperature. The mixture was cooled in an ice bath and methanesulfonyl chloride (0.69 mL, 8.915 mmol) was added and the reaction mixture was stirred at 4° C. overnight. The reaction mixture was diluted with DCM and washed with sat. NaHCO$_3$ solution, water, brine, and dried with Na$_2$SO$_4$. After filtration, the filtrate was concentrated and the residue was purified by column chromatography using a 5% EtOAc/hexane to 10% EtOAc/hexane gradient to give 35 as a white solid (1.063 g, 3.643 mmol, 62.0%). TLC (25% EtOAc/hexane)=0.69. Mp 128-129° C. $^1$H NMR (CDCl$_3$, 600 MHz): δ ppm 8.01 (2H, d, J=8.1 Hz), 7.68 (2H, d, J=8.2 Hz), 4.73 (2H, s), 2.55 (3H, s). $^{13}$C NMR (CDCl$_3$, 150 MHz): δ ppm 162.90, 149.33, 136.56, 133.99, 131.63 (q, $^2J_{FC}$=32.6), 126.64, 126.06 (q, $^3J_{FC}$=4 Hz), 124.03 (q, $^1J_{FC}$=270 Hz), 38.82, 11.66. Anal. Calcd. for $C_{12}H_9F_3NSCl$: C, 49.41; H, 3.11; N, 4.80. Found: C, 49.40; H, 3.06; N, 4.80.

Ethyl 4-[N-Methyl-N-[4-methylene-5-methyl-2-[4-(trifluoromethyl)phenyl]thiazole]]aminocinnamate (36)

Ethyl ester 35 (0.419 g, 2.041 mmol), thiazole 4b (0.614 g, 2.105 mmol), and NaI (0.463 g, 3.085 mmol) were all dissolved in DMF (20 mL) and cooled in ice bath. NaH (60% dispersion in oil, 0.112 g, 4.654 mmol) was added and the reaction mixture was stirred at room temperature for 2.5 hours. The reaction mixture was quenched with 50% NaHCO$_3$ and extracted with ether three times. The ether extracts were combined and washed with brine and dried with Na$_2$SO$_4$. After filtration, the filtrate was concentrated and the residue was purified by column chromatography using a 10% EtOAc/hexane to 25% EtOAc/hexane to give 36 as a yellow solid (0.725 g, 1.574 mmol, 77.1%). TLC (25% EtOAc/hexane)=0.41. Mp 157-158° C. Anal. Calcd. for $C_{24}H_{23}F_3N_2O_2S$: C, 62.60; H, 5.03; N, 6.08. Found: C, 62.32; H, 5.16; N, 6.05.

4-[N-Methyl-N-[4-methylene-5-methyl-2-[4-(trifluoromethyl)phenyl]thiazole]]aminocinnamic Acid (JM-1-39)

Ethyl ester 36 (0.666 g, 1.446 mmol) was dissolved in 95% ethanol (10 mL) and THF (10 mL) and cooled in ice bath. 3N NaOH (3 mL) was slowly added and the reaction mixture was stirred for 2 days at room temperature. The reaction mixture was neutralized with acidic water (HCl, pH=3) and diluted with EtOAc. The organic phase was collected and washed with water, brine, and dried with Na$_2$SO$_4$. After filtration, the filtrate was concentrated and the residue was purified by column chromatography using a 15% EtOAc/hexane to 50% EtOAc gradient supplemented with dropwise amounts of acetic acid to give the desired product JM-1-39 as orange solid (0.089 g, 0.205 mmol, 14.2%). TLC (50% EtOAc/hexane)=0.47. Mp 232-234° C. $^1$H NMR (Acetone-d6, 600 MHz): δ ppm 8.09 (2H, d, J=8.1 Hz), 7.79 (2H, d, J=8.1 Hz), 7.57 (1H, d, J=15.8 Hz), 7.50 (2H, d, J=8.9 Hz), 6.93 (2H, d, J=8.9 Hz), 6.24 (1H, d, J=15.8 Hz), 4.74 (2H, s), 3.20 (3H, s), 2.58 (3H, s). $^{13}$C NMR (Acetone-d6, 150 MHz): δ ppm 168.37, 162.34, 152.11, 151.78, 146.03, 138.02, 132.16, 131.36 (q, $^2J_{FC}$=33 Hz), 130.05, 127.22, 126.88 (q, $^3J_{FC}$=3.9 Hz), 125.14 (q, $^1J_{FC}$=270 Hz), 123.38, 113.31, 50.68, 39.20, 11.37. Anal. Calcd. for $C_{22}H_{19}F_3N_2O_2S$ (with 0.1 mol H$_2$O per target): C, 60.60; H, 4.48; N, 6.42. Found: C, 60.56; H, 4.57; N, 6.27.

Ethyl 5-Methyl-2-[4-(trifluoromethyl)phenyl]-1,2,3-triazole-4-carboxylate (37)

4-(Trifluoromethyl)aniline (0.217 g, 1.347 mmol) was diluted in EtOAc and precipitated using concentrated HCl. The precipitate was collected and dissolved in water, then added acetic acid (1 mL) and concentrated HCl (0.5 mL) while in ice bath. NaNO$_2$ (0.103 g, 1.493 mmol) was dissolved in water and slowly added to the mixture already in the ice bath. NaOAc (0.107 g, 1.304 mmol) was dissolved in 1N Na$_2$CO$_3$ (1 mL) and added to a chilled 0° C. solution of ethyl acetoacetate (0.18 mL, 1.42 mmol) in EtOH. The resulting solution was slowly added to the first mixture containing 4-(trifluoromethyl)aniline and the combined mixture was stirred for two hours at 0° C. The reaction mixture was diluted with EtOAc and washed with water, brine, dried with Na$_2$SO$_4$, and filtered. The filtrate was concentrated and the residue was dissolved in 95% ethanol (20 mL). Copper chloride dihydrate (0.523 g, 3.068 mmol) and NH$_4$OAc (1.054 g, 13.674 mmol) were added and the mixture was stirred at reflux temperature overnight. The reaction mixture was diluted with 2N HCl and extracted with EtOAc. The organic extract was washed with brine, dried with Na$_2$SO$_4$, and filtered. The filtrate was concentrated and purified by column chromatography using a 5% to 10% EtOAc/hexane gradient to give the desired product 37 as a yellow solid (0.026 g, 0.088 mmol, 6.5%).

5-Methyl-2-[4-(trifluoromethyl)phenyl]-1,2,3-triazole-4-methanol (38)

The method used for synthesis of 38 is analogous to the previously described method used in the synthesis of 3a-d with the starting reactant being 37.

4-Chloromethyl-5-methyl-2-[4-(trifluoromethyl)phenyl]-1,2,3-triazole (39)

The method used for synthesis of 39 is analogous to the previously described method used in the synthesis of 4a-d with the starting reactant being 38.

Ethyl 4-[N-Methyl-N-[5-methyl-4-methylene-2-[4-(trifluoromethyl)phenyl]-1,2,3-triazole]]aminocinnamate (40)

The method used for synthesis of 40 is analogous to the previously described method used in the synthesis of 16a-d with the starting reactants being 39 and 15.

4-[N-Methyl-N-[5-methyl-4-methylene-2-[4-(trifluoromethyl)phenyl]-1,2,3-triazole]]aminocinnamic Acid (41)

The method used for synthesis of 41 is analogous to the previously described method used in the synthesis of BK-4-15 with the starting reactant being 40.

4-[N-Methyl-N-[5-methylene-4-methyl-2-[4-(trifluoromethyl)phenyl]thiazole]]aminocinnamyl Alcohol (42)

The method used for synthesis of 42 is analogous to the previously described method used in the synthesis of 3a-d with the starting reactant being 16b.

4-[N-Methyl-N-[5-methylene-4-methyl-2-[4-(trifluoromethyl)phenyl]thiazole]]aminocinnamonitrile (43)

The method used for synthesis of 43 is analogous to the methods used in the reference from Zhu, C et. al. that uses the reagents TEMPO, HTIB, NH$_4$OAc with the starting reactant being 42.

4-[2-(1H-Tetrazol-5-yl)vinyl]-N-methyl-N-[(4-methyl-2-(4-(trifluoromethyl)phenyl)thiazol-5-yl)methyl]aniline (44)

The method used for synthesis of 44 is analogous to the methods used in the reference from Demko, Z. P.; Sharpless, K. B. *J. Org. Chem.* 2001, 66, 7945-7950, with the starting reactant being 43.

4-Bromo-N-(tert-butoxycarbonyl)aniline (45)

The method used for synthesis of 45 is analogous to the previously described method used in the synthesis of 10 with the starting reactant being 4-Bromoaniline.

4-Bromo-[N-(tert-butoxycarbonyl)-N-methyl]aniline (46)

The method used for synthesis of 46 is analogous to the previously described method used in the synthesis of 14 with the starting reactant being 45.

4-Bromo-N-(methyl)aniline (47)

The method used for synthesis of 47 is analogous to the previously described method used in the synthesis of 15 with the starting reactant being 46.

4-Bromo-[N-Methyl-N-[5-methylene-4-methyl-2-[4-(trifluoromethyl)phenyl]thiazole]]aniline (48)

The method used for synthesis of 48 is analogous to the previously described method used in the synthesis of 16b with the starting reactants being 47 and 4b.

2-[4-[N-Methyl-N-[5-methylene-4-methyl-2-[4-(trifluoromethyl)phenyl]thiazole]amino]phenyl]ethene-1-sulfonic Acid, sodium salt (49)

The method used for synthesis of 49 is analogous to the methods used in the reference from Prakash, G. K. S.; Jog, P. V.; Krishnan, H. S.; Olah, G. A. *J. Am. Chem. Soc.* 2011, 133(7), 2140-2143, with the starting material being 48.

1,1,1-Trifluoro-3-buten-2-ol (50)

The method used for synthesis of 50 is analogous to the methods used in the reference from Gajewski, J. J.; Gee, K. R.; Jurayj, J. *J. Org. Chem.* 1990, 55, 1813-1822, with trifluoroacetaldehyde as starting material.

1,1,1-Trifluoro-4-[4-[N-[5-methylene-4-methyl-2-[4-(trifluoromethyl)phenyl]thiazole]methylamino]phenyl]but-3-en-2-ol (51)

The method used for synthesis of 51 is analogous to the methods used in the reference from Prakash, G. K. S.; Jog, P. V.; Krishnan, H. S.; Olah, G. A. *J. Am. Chem. Soc.* 2011, 133(7), 2140-2143, with the starting materials being 48 and 50.

4-[N-[5-Methylene-4-methyl-2[(4-(trifluoromethyl)phenyl]thiazole]methylamino]styrylphosphonic Acid (53a)

The method used for synthesis of 53a (and 53b, 53c) is analogous to the methods used in the reference from Saha, U.; Helvig, C. F.; Petkovich, P. M. PCT Int. Appl. 2010, WO2010083613, with 52a (and 52b, 52c respectively) and bis-diethylphosphonate as the starting reagents.

4-(Methylamino)benzonitrile (54)

The method used for the synthesis of 54 is analogous to the methods used in the previously described multistep synthesis of 15 with 4-Aminobenzonitrile.

4-[N-[5-Methylene-4-methyl-2-[4-(trifluoromethyl) phenyl]thiazole]]methylamino]benzonitrile (55)

The method used for synthesis of 55 is analogous to the method used in the previously described synthesis of 16 with 54 and 4b as starting materials.

4-[N-[5-Methylene-4-methyl-2-[4-(trifluoromethyl) phenyl]thiazole]methylamino]styrylboronic Acid (56)

The method used for the synthesis of 56 is analogous to the method used in the reference from Gopula, Balraj et. al. Org Lett. 2014, 16(2), 632-635, with 55 as the starting reagent.

Alkyl 2-[4-[N-[5-methylene-4-methyl-2-[4-(trifluoromethyl)phenyl]thiazole]methylamino]phenyl] ethene-1-sulfonamide (57)

The method used for the synthesis of various analogs of 57 is analogous to the method used in the reference from Rad, M. N. S. et. al. Synthesis. 2009, 23, 3983-3988, with 49 and primary or secondary amines as the starting materials.

6-(N-tert-Butoxycarbonyl)amino-2-naphthalenesulfonic Acid (58)

The method used for the synthesis of 58 is analogous to the method used in the previously described synthesis of 10 with commercially available 6-Amino-2-naphthalenesulfonic acid as starting material.

6-[N-(tert-Butoxycarbonyl)methylamino]-2-naphthalenesulfonic Acid (59)

The method used for the synthesis of 59 is analogous to the method used in the previously described synthesis of 14 with 58 being the starting material.

6-(N-Methylamino)-2-naphthalenesulfonic Acid (60)

The method used for the synthesis of 60 is analogous to the method used in the previously described synthesis of 15 with 59 being the starting material.

6-[N-[5-Methylene-4-methyl-2-[4-(trifluoromethyl) phenyl]thiazole]methylamino]-2-naphthalenesulfonic Acid (61)

The method used for the synthesis of 61 is analogous to the method used in the previously described synthesis of 16 with 60 and 4b being the starting materials.

Alkyl 6-[N-[5-methylene-4-methyl-2-[4-(trifluoromethyl)phenyl]thiazole]methylamino]-2-naphthalenesulfonamide (61)

The method used for the synthesis of various analogs of 61 is analogous to the method used in the reference from Rad, M. N. S. et al. Synthesis. 2009, 23, 3983-3988, with 60 and primary or secondary amines as the starting materials.

Certain embodiments of the compounds, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method of inducing osteogenesis, comprising:
administering an effective amount of a pharmaceutical composition to a mammalian patient in need thereof, the pharmaceutical composition comprising a peroxisome proliferator activated receptor (PPAR) compound in an amount sufficient to prompt stem cells in the patient to contribute toward bone formation, and a pharmaceutically acceptable carrier, excipient, diluent or adjuvant; wherein the PPAR compound has a chemical structure of Formula I:

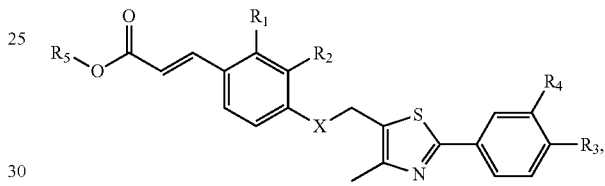

wherein:
X is $NCH_3$;
$R_1$ is H;
$R_2$ is H;
$R_3$ is $CF_3$;
$R_4$ is H; and
$R_5$ is H;
and salts, isomers, solvates, hydrates, polymorphs, and prodrugs thereof.

2. The method of claim 1, wherein the mammalian patient is a human.

3. The method of claim 1, wherein the administration is by surgical implantation including allograft bone, bone substitutes or bone scaffold matrices, or by localized injection of liquid or gel formulations or delivery systems to or near the bone.

4. The method of claim 1, wherein the administration is by an intravenous, intramuscular or subcutaneous injection of liquid or gel formulations or delivery systems.

5. The method of claim 1, wherein the stem cells are present in a human patient in need of therapy for osteoarthritis, cartilage disorder, bone fracture, osteoporosis, metabolic bone disease, avascular necrosis, or concurrent with skeletal surgery.

6. The method of claim 5, wherein the administration is by surgical implantation including allograft bone, bone substitutes or bone scaffold matrices, or by localized injection of liquid or gel formulations or delivery systems to or near the fracture or site of skeletal surgery.

7. The method of claim 5, wherein the administration is by an intravenous, intramuscular or subcutaneous injection of liquid or gel formulations or delivery systems.

8. The method of claim 5, wherein the administration is by the oral route.

* * * * *